(12) United States Patent
Minnelli et al.

(10) Patent No.: US 11,235,111 B2
(45) Date of Patent: Feb. 1, 2022

(54) SURGICAL ACCESS DEVICE

(71) Applicant: Ethicon LLC, Guaynabo, PR (US)

(72) Inventors: Patrick J. Minnelli, Harrison, OH (US); Kevin M. Montgomery, Camden, OH (US)

(73) Assignee: Ethicon LLC, Guaynabo, PR (US)

( * ) Notice: Subject to any disclaimer, the term of this patent is extended or adjusted under 35 U.S.C. 154(b) by 742 days.

(21) Appl. No.: 15/823,345

(22) Filed: Nov. 27, 2017

(65) Prior Publication Data

US 2018/0104423 A1    Apr. 19, 2018

Related U.S. Application Data

(63) Continuation of application No. 14/150,256, filed on Jan. 8, 2014, which is a continuation of application
(Continued)

(51) Int. Cl.
*A61M 13/00* (2006.01)
*A61B 17/34* (2006.01)
(Continued)

(52) U.S. Cl.
CPC ....... *A61M 13/003* (2013.01); *A61B 1/00128* (2013.01); *A61B 1/00137* (2013.01);
(Continued)

(58) Field of Classification Search
CPC ............. A61M 13/003; A61B 1/00128; A61B 1/00137; A61B 1/122; A61B 17/0218;
(Continued)

(56) References Cited

U.S. PATENT DOCUMENTS

| 477,639 A | 6/1892 | Brinkerhoff |
| 1,641,856 A | 9/1927 | Lloyd et al. |
| (Continued) | | |

FOREIGN PATENT DOCUMENTS

| CA | 2060930 A1 | 10/1992 |
| CA | 2661238 A1 | 10/2009 |
| (Continued) | | |

OTHER PUBLICATIONS

Extended European Search Report issued in European Application No. 12173272.1 dated Jul. 19, 2012.
(Continued)

*Primary Examiner* — Bhisma Mehta
*Assistant Examiner* — Larry R. Wilson
(74) *Attorney, Agent, or Firm* — Mintz Levin Cohn Ferris Glovsky and Popeo, P.C.

(57) ABSTRACT

The present invention generally provides methods and devices for removing fluid from a surgical instrument. Surgical access devices and seal systems are generally provided having one or more valves or seal assemblies to create a closed system between the outside environment and the environment in which the surgical access device is being inserted. The devices of systems can also include a fluid remover in the form of a sorbent element, a scraper element, a wicking element, or any combination thereof that is configured to remove fluid from a working channel of the device or system and/or from a surgical instrument inserted therethrough.

17 Claims, 48 Drawing Sheets

Related U.S. Application Data

No. 12/902,265, filed on Oct. 12, 2010, now Pat. No. 8,636,686, which is a continuation-in-part of application No. 12/533,590, filed on Jul. 31, 2009, now Pat. No. 8,568,362, which is a continuation-in-part of application No. 12/110,724, filed on Apr. 28, 2008, now Pat. No. 8,579,807, and a continuation-in-part of application No. 12/110,727, filed on Apr. 28, 2008, now Pat. No. 8,870,747, and a continuation-in-part of application No. 12/110,742, filed on Apr. 28, 2008, now Pat. No. 9,358,041, and a continuation-in-part of application No. 12/110,755, filed on Apr. 28, 2008, now Pat. No. 8,273,060.

(51) Int. Cl.
*A61B 1/12* (2006.01)
*A61B 90/70* (2016.01)
*A61B 1/00* (2006.01)
*A61B 17/02* (2006.01)
*A61B 17/00* (2006.01)

(52) U.S. Cl.
CPC ...... *A61B 17/0218* (2013.01); *A61B 17/3423* (2013.01); *A61B 17/3462* (2013.01); *A61B 17/3474* (2013.01); *A61B 17/3498* (2013.01); *A61B 1/122* (2013.01); *A61B 90/70* (2016.02); *A61B 2017/003* (2013.01); *A61B 2017/3437* (2013.01); *A61B 2017/3464* (2013.01)

(58) Field of Classification Search
CPC ............ A61B 17/3423; A61B 17/3474; A61B 17/3498; A61B 2017/3437; A61B 2017/3464; A61B 90/70
USPC ............ 600/101, 205, 210; 604/23–26, 158, 604/164.01, 164.03, 164.04, 604/167.01–167.05, 264; 606/191, 195
See application file for complete search history.

(56) References Cited

U.S. PATENT DOCUMENTS

| | | |
|---|---|---|
| 1,775,403 A | 9/1930 | Maclean |
| 2,628,404 A | 2/1953 | Myers |
| 3,229,691 A | 1/1966 | Crowe, Jr. |
| 3,566,871 A | 3/1971 | Richter et al. |
| 3,900,022 A | 8/1975 | Widran |
| 3,903,877 A | 9/1975 | Terada |
| 3,924,608 A | 12/1975 | Mitsui |
| 3,980,078 A | 9/1976 | Tominaga |
| 3,981,276 A | 9/1976 | Ernest |
| 4,204,563 A | 5/1980 | Pyle |
| 4,279,246 A | 7/1981 | Chikama |
| 4,281,646 A | 8/1981 | Kinoshita |
| 4,335,721 A | 6/1982 | Matthews |
| 4,352,527 A | 10/1982 | Sandstrom |
| 4,363,357 A | 12/1982 | Hunter |
| 4,453,838 A | 6/1984 | Loizeau |
| 4,651,517 A | 3/1987 | Benhamou et al. |
| 4,687,033 A | 8/1987 | Furrow et al. |
| 4,690,140 A | 9/1987 | Mecca |
| 4,722,000 A | 1/1988 | Chatenever |
| 4,836,187 A | 6/1989 | Iwakoshi et al. |
| 4,844,052 A | 7/1989 | Iwakoshi et al. |
| 4,847,364 A | 7/1989 | Mockli |
| 4,877,016 A | 10/1989 | Kantor et al. |
| 4,919,305 A | 4/1990 | Podgers |
| 4,929,235 A | 5/1990 | Merry et al. |
| 4,934,135 A | 6/1990 | Rozenwasser |
| 4,942,867 A | 7/1990 | Takahashi et al. |
| 4,943,280 A | 7/1990 | Lander |
| 4,958,970 A | 9/1990 | Rose et al. |
| 4,960,412 A | 10/1990 | Fink |
| 5,000,745 A | 3/1991 | Guest et al. |
| 5,013,199 A | 5/1991 | Downes |
| 5,084,057 A | 1/1992 | Green et al. |
| 5,104,383 A | 4/1992 | Shichman |
| 5,112,308 A | 5/1992 | Olsen et al. |
| 5,127,909 A | 7/1992 | Shichman |
| 5,167,220 A | 12/1992 | Brown |
| 5,180,373 A | 1/1993 | Green et al. |
| 5,191,878 A | 3/1993 | Iida et al. |
| 5,197,955 A | 3/1993 | Stephens et al. |
| 5,201,714 A | 4/1993 | Gentelia et al. |
| 5,207,213 A | 5/1993 | Auhll et al. |
| 5,209,737 A | 5/1993 | Ritchart et al. |
| 5,226,891 A | 7/1993 | Bushatz et al. |
| 5,237,984 A | 8/1993 | Williams, III et al. |
| 5,242,412 A | 9/1993 | Blake, III |
| 5,256,149 A | 10/1993 | Banik et al. |
| 5,274,874 A | 1/1994 | Cercone et al. |
| 5,279,542 A | 1/1994 | Wilk |
| 5,308,336 A | 5/1994 | Hart et al. |
| 5,312,351 A | 5/1994 | Gerrone |
| 5,312,363 A | 5/1994 | Ryan et al. |
| 5,312,397 A | 5/1994 | Cosmescu |
| 5,313,934 A | 5/1994 | Wiita et al. |
| 5,320,608 A | 6/1994 | Gerrone |
| 5,320,610 A | 6/1994 | Yoon |
| 5,326,013 A | 7/1994 | Green et al. |
| 5,330,437 A | 7/1994 | Durman |
| 5,334,164 A | 8/1994 | Guy et al. |
| 5,337,730 A | 8/1994 | Maguire |
| 5,339,800 A | 8/1994 | Wiita et al. |
| 5,342,315 A | 8/1994 | Rowe et al. |
| 5,347,988 A | 9/1994 | Hori |
| 5,354,302 A | 10/1994 | Ko |
| 5,364,002 A | 11/1994 | Green et al. |
| 5,369,525 A | 11/1994 | Bala et al. |
| 5,370,656 A | 12/1994 | Shevel |
| 5,377,669 A | 1/1995 | Schulz |
| 5,382,297 A | 1/1995 | Valentine et al. |
| 5,386,817 A | 2/1995 | Jones |
| 5,387,197 A | 2/1995 | Smith et al. |
| 5,389,081 A | 2/1995 | Castro |
| 5,391,154 A | 2/1995 | Young |
| 5,392,766 A | 2/1995 | Masterson et al. |
| 5,395,342 A | 3/1995 | Yoon |
| 5,400,767 A | 3/1995 | Murdoch |
| 5,407,433 A | 4/1995 | Loomas |
| 5,419,309 A | 5/1995 | Biehl |
| 5,419,311 A | 5/1995 | Yabe et al. |
| 5,441,513 A | 8/1995 | Roth |
| 5,443,452 A | 8/1995 | Hart et al. |
| 5,448,990 A | 9/1995 | De Faria-Correa |
| 5,449,370 A | 9/1995 | Vaitekunas |
| 5,458,633 A | 10/1995 | Bailey |
| 5,458,640 A | 10/1995 | Gerrone |
| 5,462,100 A | 10/1995 | Covert et al. |
| 5,464,008 A | 11/1995 | Kim |
| 5,476,475 A | 12/1995 | Gadberry |
| 5,486,154 A | 1/1996 | Kelleher |
| 5,492,304 A | 2/1996 | Smith et al. |
| 5,496,142 A | 3/1996 | Fodor et al. |
| 5,496,280 A * | 3/1996 | Vandenbroek ..... A61B 17/3498 604/167.03 |
| 5,496,345 A | 3/1996 | Kieturakis et al. |
| 5,496,411 A | 3/1996 | Candy |
| 5,514,084 A | 5/1996 | Fisher |
| 5,514,153 A | 5/1996 | Bonutti |
| 5,518,026 A | 5/1996 | Benjey |
| 5,518,502 A | 5/1996 | Kaplan et al. |
| 5,522,833 A | 6/1996 | Stephens et al. |
| 5,533,496 A | 7/1996 | De Faria-Correa et al. |
| 5,535,759 A | 7/1996 | Wilk |
| 5,536,234 A | 7/1996 | Newman |
| 5,542,931 A | 8/1996 | Gravener et al. |
| 5,545,142 A | 8/1996 | Stephens et al. |
| 5,545,179 A | 8/1996 | Williamson, IV |
| 5,549,543 A | 8/1996 | Kim |
| 5,551,448 A | 9/1996 | Matula et al. |
| 5,554,151 A | 9/1996 | Hinchliffe |

(56) References Cited

U.S. PATENT DOCUMENTS

| | | |
|---|---|---|
| 5,568,828 A | 10/1996 | Harris |
| 5,569,183 A | 10/1996 | Kieturakis |
| 5,569,205 A | 10/1996 | Hart et al. |
| 5,575,756 A | 11/1996 | Karasawa et al. |
| 5,584,850 A | 12/1996 | Hart et al. |
| 5,590,697 A | 1/1997 | Benjey et al. |
| 5,591,192 A | 1/1997 | Privitera et al. |
| 5,603,702 A | 2/1997 | Smith et al. |
| 5,605,175 A | 2/1997 | Bergsma et al. |
| 5,628,732 A | 5/1997 | Antoon, Jr. et al. |
| 5,630,795 A | 5/1997 | Kuramoto et al. |
| 5,630,813 A | 5/1997 | Kieturakis |
| 5,634,911 A | 6/1997 | Hermann et al. |
| 5,643,227 A | 7/1997 | Stevens |
| 5,643,301 A | 7/1997 | Mollenauer |
| 5,647,372 A | 7/1997 | Tovey et al. |
| 5,647,840 A | 7/1997 | D'Amelio et al. |
| 5,651,757 A | 7/1997 | Meckstroth |
| 5,658,273 A | 8/1997 | Long |
| 5,662,614 A | 9/1997 | Edoga |
| 5,685,823 A | 11/1997 | Ito et al. |
| 5,688,222 A | 11/1997 | Hluchy et al. |
| 5,709,664 A | 1/1998 | Vandenbroek et al. |
| 5,720,756 A | 2/1998 | Green et al. |
| 5,720,759 A | 2/1998 | Green et al. |
| 5,725,477 A | 3/1998 | Yasui et al. |
| 5,725,478 A | 3/1998 | Saad |
| 5,743,884 A | 4/1998 | Hasson et al. |
| 5,752,938 A | 5/1998 | Flatland et al. |
| 5,755,252 A | 5/1998 | Bergsma et al. |
| 5,755,732 A | 5/1998 | Green et al. |
| 5,776,112 A | 7/1998 | Stephens et al. |
| 5,782,751 A | 7/1998 | Matsuno |
| 5,782,859 A | 7/1998 | Nicholas et al. |
| 5,788,676 A | 8/1998 | Yoon |
| 5,792,044 A | 8/1998 | Foley et al. |
| 5,792,113 A | 8/1998 | Kramer et al. |
| 5,797,434 A | 8/1998 | Benjey et al. |
| 5,807,338 A | 9/1998 | Smith et al. |
| 5,814,026 A | 9/1998 | Yoon |
| D399,316 S | 10/1998 | Molina |
| 5,817,061 A | 10/1998 | Goodwin et al. |
| 5,820,600 A | 10/1998 | Carlson et al. |
| 5,842,971 A | 12/1998 | Yoon |
| 5,848,992 A | 12/1998 | Hart et al. |
| 5,860,458 A | 1/1999 | Benjey et al. |
| 5,871,440 A | 2/1999 | Okada |
| 5,882,345 A | 3/1999 | Yoon |
| 5,895,377 A | 4/1999 | Smith et al. |
| 5,902,231 A | 5/1999 | Foley et al. |
| 5,902,264 A | 5/1999 | Toso et al. |
| 5,906,595 A | 5/1999 | Powell et al. |
| 5,906,598 A | 5/1999 | Giesler et al. |
| 5,944,654 A | 8/1999 | Crawford |
| 5,954,635 A | 9/1999 | Foley et al. |
| 5,957,888 A | 9/1999 | Hinchliffe |
| 5,961,505 A | 10/1999 | Coe et al. |
| 5,964,781 A | 10/1999 | Mollenauer et al. |
| 5,983,958 A | 11/1999 | Bergsma et al. |
| 5,989,183 A | 11/1999 | Reisdorf et al. |
| 5,989,224 A | 11/1999 | Exline et al. |
| 5,993,380 A | 11/1999 | Yabe et al. |
| 6,004,326 A | 12/1999 | Castro et al. |
| 6,007,487 A | 12/1999 | Foley et al. |
| 6,017,333 A | 1/2000 | Bailey |
| D425,619 S | 5/2000 | Bierman |
| 6,062,276 A | 5/2000 | Benjey et al. |
| 6,063,050 A | 5/2000 | Manna et al. |
| 6,110,103 A | 8/2000 | Donofrio |
| 6,126,592 A | 10/2000 | Proch et al. |
| 6,152,871 A | 11/2000 | Foley et al. |
| 6,159,182 A | 12/2000 | Davis et al. |
| 6,162,170 A | 12/2000 | Foley et al. |
| 6,167,920 B1 | 1/2001 | Enge |
| 6,176,823 B1 | 1/2001 | Foley et al. |
| 6,176,825 B1 | 1/2001 | Chin et al. |
| 6,206,057 B1 | 3/2001 | Benjey et al. |
| 6,206,822 B1 | 3/2001 | Foley et al. |
| 6,209,306 B1 | 4/2001 | Chia et al. |
| 6,216,661 B1 | 4/2001 | Pickens et al. |
| 6,217,509 B1 | 4/2001 | Foley et al. |
| 6,253,802 B1 | 7/2001 | Enge |
| 6,258,025 B1 | 7/2001 | Swallert |
| 6,258,065 B1 | 7/2001 | Dennis et al. |
| 6,264,604 B1 | 7/2001 | Kieturakis et al. |
| 6,287,313 B1 | 9/2001 | Sasso |
| 6,354,992 B1 | 3/2002 | Kato |
| 6,371,909 B1 | 4/2002 | Hoeg et al. |
| 6,409,657 B1 | 6/2002 | Kawano |
| 6,423,266 B1 | 7/2002 | Choperena et al. |
| 6,425,535 B1 | 7/2002 | Akiba |
| 6,425,859 B1 | 7/2002 | Foley et al. |
| 6,443,190 B1 | 9/2002 | Enge |
| 6,447,446 B1 | 9/2002 | Smith et al. |
| 6,482,181 B1 | 11/2002 | Racenet et al. |
| 6,494,893 B2 | 12/2002 | Dubrul et al. |
| 6,497,687 B1 | 12/2002 | Blanco |
| 6,516,835 B2 | 2/2003 | Enge |
| 6,517,246 B2 | 2/2003 | Blakley |
| 6,520,907 B1 | 2/2003 | Foley et al. |
| 6,534,002 B1 | 3/2003 | Lin et al. |
| 6,551,282 B1 | 4/2003 | Exline et al. |
| 6,562,046 B2 | 5/2003 | Sasso |
| 6,569,120 B1 | 5/2003 | Green et al. |
| 6,595,915 B2 | 7/2003 | Akiba |
| 6,595,946 B1 | 7/2003 | Pasqualucci |
| 6,601,617 B2 | 8/2003 | Enge |
| 6,605,098 B2 | 8/2003 | Nobis et al. |
| 6,638,214 B2 | 10/2003 | Akiba |
| 6,648,906 B2 | 11/2003 | Lasheras et al. |
| 6,668,418 B2 | 12/2003 | Bastien |
| 6,679,833 B2 | 1/2004 | Smith et al. |
| 6,679,834 B2 | 1/2004 | Stahl et al. |
| 6,679,837 B2 | 1/2004 | Daikuzono |
| 6,685,665 B2 | 2/2004 | Booth et al. |
| 6,699,185 B2 | 3/2004 | Gminder et al. |
| 6,702,787 B2 | 3/2004 | Racenet et al. |
| 6,712,757 B2 | 3/2004 | Becker et al. |
| 6,726,663 B1 | 4/2004 | Dennis |
| 6,755,782 B2 | 6/2004 | Ogawa |
| 6,860,869 B2 | 3/2005 | Dennis |
| 6,860,892 B1 | 3/2005 | Tanaka et al. |
| 6,873,409 B1 | 3/2005 | Slater |
| 6,916,286 B2 | 7/2005 | Kazakevich |
| 6,918,924 B2 | 7/2005 | Lasheras et al. |
| 6,923,759 B2 | 8/2005 | Kasahara et al. |
| 6,942,671 B1 | 9/2005 | Smith |
| 6,976,957 B1 | 12/2005 | Chin et al. |
| 6,981,966 B2 | 1/2006 | Green et al. |
| 6,989,003 B2 | 1/2006 | Wing et al. |
| 7,008,416 B2 | 3/2006 | Sakaguchi et al. |
| 7,025,747 B2 | 4/2006 | Smith |
| 7,052,454 B2 | 5/2006 | Taylor |
| 7,056,303 B2 | 6/2006 | Dennis et al. |
| 7,056,321 B2 | 6/2006 | Pagliuca et al. |
| 7,060,025 B2 | 6/2006 | Long et al. |
| 7,077,803 B2 | 7/2006 | Kasahara et al. |
| 7,083,626 B2 | 8/2006 | Hart et al. |
| 7,104,657 B2 | 9/2006 | Sherwin |
| 7,105,009 B2 | 9/2006 | Johnson et al. |
| 7,112,185 B2 | 9/2006 | Hart et al. |
| 7,163,525 B2 | 1/2007 | Franer |
| 7,169,130 B2 | 1/2007 | Exline et al. |
| D541,417 S | 4/2007 | Albrecht et al. |
| 7,198,598 B2 | 4/2007 | Smith et al. |
| 7,207,347 B2 | 4/2007 | Olshanetsky et al. |
| 7,244,244 B2 | 7/2007 | Racenet et al. |
| D555,788 S | 11/2007 | Southwell et al. |
| 7,309,469 B2 | 12/2007 | Anderson et al. |
| D559,080 S | 1/2008 | Boote |
| 7,322,964 B2 * | 1/2008 | Pajunk ............... A61B 17/3498 604/246 |
| 7,344,519 B2 | 3/2008 | Wing et al. |
| D567,372 S | 4/2008 | Chesnin |

(56) References Cited

U.S. PATENT DOCUMENTS

| | | |
|---|---|---|
| 7,371,227 B2 | 5/2008 | Zeiner |
| D573,255 S | 7/2008 | Stephens |
| 7,444,801 B2 | 11/2008 | Rosenwasser et al. |
| 7,473,243 B2 | 1/2009 | Dennis et al. |
| D589,617 S | 3/2009 | Carter |
| 7,507,210 B2 | 3/2009 | Hibner et al. |
| 7,591,802 B2 | 9/2009 | Johnson et al. |
| 7,717,412 B2 | 5/2010 | Anzai |
| 7,785,294 B2 | 8/2010 | Hueil et al. |
| 7,981,092 B2 | 7/2011 | Duke |
| 8,075,528 B2 | 12/2011 | Widenhouse et al. |
| 8,079,986 B2 | 12/2011 | Taylor et al. |
| D652,509 S | 1/2012 | Kyvik et al. |
| 8,147,481 B2 | 4/2012 | Whittaker et al. |
| 8,206,357 B2 | 6/2012 | Bettuchi |
| 8,206,376 B2 | 6/2012 | Barron et al. |
| 8,273,060 B2 | 9/2012 | Moreno, Jr. et al. |
| 8,328,768 B2 | 12/2012 | Quigley et al. |
| 8,551,058 B2 | 10/2013 | Measamer et al. |
| 8,568,362 B2 | 10/2013 | Moreno, Jr. et al. |
| 8,579,807 B2 | 11/2013 | Moreno, Jr. et al. |
| 8,636,686 B2 * | 1/2014 | Minnelli ............ A61B 1/00128 604/26 |
| 2002/0022762 A1 | 2/2002 | Beane et al. |
| 2002/0035828 A1 | 3/2002 | Chia et al. |
| 2002/0065450 A1 | 5/2002 | Ogawa |
| 2002/0068923 A1 | 6/2002 | Caldwell et al. |
| 2002/0103420 A1 | 8/2002 | Coleman et al. |
| 2002/0107484 A1 | 8/2002 | Dennis et al. |
| 2002/0161387 A1 | 10/2002 | Blanco |
| 2003/0004529 A1 | 1/2003 | Tsonton et al. |
| 2003/0060770 A1 | 3/2003 | Wing et al. |
| 2003/0130674 A1 | 7/2003 | Kasahara et al. |
| 2003/0135942 A1 | 7/2003 | Bastien |
| 2003/0139756 A1 | 7/2003 | Brustad |
| 2003/0195472 A1 | 10/2003 | Green et al. |
| 2003/0208104 A1 | 11/2003 | Carrillo et al. |
| 2004/0034339 A1 | 2/2004 | Stoller et al. |
| 2004/0106942 A1 | 6/2004 | Taylor et al. |
| 2004/0167559 A1 | 8/2004 | Taylor et al. |
| 2004/0171990 A1 | 9/2004 | Dennis et al. |
| 2004/0220452 A1 | 11/2004 | Shalman |
| 2004/0230161 A1 | 11/2004 | Zeiner |
| 2004/0256004 A1 | 12/2004 | Kessell et al. |
| 2004/0260244 A1 | 12/2004 | Piechowicz et al. |
| 2005/0033342 A1 | 2/2005 | Hart et al. |
| 2005/0043683 A1 | 2/2005 | Ravo |
| 2005/0059865 A1 | 3/2005 | Kahle et al. |
| 2005/0059934 A1 * | 3/2005 | Wenchell ............ A61B 17/3439 604/167.01 |
| 2005/0070850 A1 | 3/2005 | Albrecht |
| 2005/0070946 A1 | 3/2005 | Franer et al. |
| 2005/0070947 A1 | 3/2005 | Franer et al. |
| 2005/0077688 A1 | 4/2005 | Voegele et al. |
| 2005/0077689 A1 | 4/2005 | Hueil |
| 2005/0096605 A1 | 5/2005 | Green et al. |
| 2005/0131349 A1 | 6/2005 | Albrecht et al. |
| 2005/0165277 A1 | 7/2005 | Carrillo et al. |
| 2005/0203543 A1 | 9/2005 | Hilal et al. |
| 2005/0216028 A1 | 9/2005 | Hart et al. |
| 2005/0222582 A1 | 10/2005 | Wenchell |
| 2005/0241647 A1 | 11/2005 | Nguyen et al. |
| 2005/0267419 A1 | 12/2005 | Smith |
| 2005/0288622 A1 | 12/2005 | Albrecht et al. |
| 2006/0020165 A1 | 1/2006 | Adams |
| 2006/0047240 A1 | 3/2006 | Kumar et al. |
| 2006/0052666 A1 | 3/2006 | Kumar et al. |
| 2006/0068360 A1 | 3/2006 | Boulais |
| 2006/0069306 A1 | 3/2006 | Banik et al. |
| 2006/0069312 A1 | 3/2006 | O'Connor |
| 2006/0100485 A1 | 5/2006 | Arai et al. |
| 2006/0122556 A1 | 6/2006 | Kumar et al. |
| 2006/0122557 A1 | 6/2006 | Kumar et al. |
| 2006/0129098 A1 | 6/2006 | Hart et al. |
| 2006/0135972 A1 | 6/2006 | Zeiner |
| 2006/0135977 A1 | 6/2006 | Thompson et al. |
| 2006/0135978 A1 | 6/2006 | Franer |
| 2006/0149137 A1 | 7/2006 | Pingleton et al. |
| 2006/0199998 A1 | 9/2006 | Akui et al. |
| 2006/0211916 A1 | 9/2006 | Kasahara et al. |
| 2006/0224121 A1 | 10/2006 | Hart et al. |
| 2006/0224164 A1 | 10/2006 | Hart et al. |
| 2006/0229565 A1 | 10/2006 | Dennis et al. |
| 2006/0235455 A1 | 10/2006 | Oshida |
| 2006/0264991 A1 | 11/2006 | Johnson et al. |
| 2006/0276688 A1 | 12/2006 | Surti |
| 2006/0293559 A1 | 12/2006 | Grice et al. |
| 2007/0005087 A1 | 1/2007 | Smith et al. |
| 2007/0021713 A1 | 1/2007 | Kumar et al. |
| 2007/0027453 A1 | 2/2007 | Hart et al. |
| 2007/0088275 A1 | 4/2007 | Stearns et al. |
| 2007/0088277 A1 | 4/2007 | McGinley et al. |
| 2007/0129719 A1 | 6/2007 | Kendale et al. |
| 2007/0142709 A1 | 6/2007 | Martone et al. |
| 2007/0149931 A1 | 6/2007 | Cannon et al. |
| 2007/0149993 A1 | 6/2007 | Kasahara et al. |
| 2007/0183867 A1 | 8/2007 | Hesselmann et al. |
| 2007/0185453 A1 | 8/2007 | Michael et al. |
| 2007/0191759 A1 | 8/2007 | Stoller et al. |
| 2007/0204890 A1 | 9/2007 | Torii |
| 2007/0225556 A1 | 9/2007 | Ortiz et al. |
| 2007/0225566 A1 | 9/2007 | Kawanishi |
| 2007/0244361 A1 | 10/2007 | Ikeda et al. |
| 2008/0009797 A1 | 1/2008 | Stellon et al. |
| 2008/0009832 A1 | 1/2008 | Barron et al. |
| 2008/0091143 A1 | 4/2008 | Taylor et al. |
| 2008/0249475 A1 | 10/2008 | Albrecht et al. |
| 2008/0269696 A1 | 10/2008 | Exline et al. |
| 2008/0275428 A1 | 11/2008 | Tegg et al. |
| 2008/0294113 A1 | 11/2008 | Brockmeier et al. |
| 2009/0005799 A1 | 1/2009 | Franer et al. |
| 2009/0030375 A1 | 1/2009 | Franer et al. |
| 2009/0093682 A1 | 4/2009 | Izzo et al. |
| 2009/0118586 A1 | 5/2009 | Griffin |
| 2009/0137943 A1 | 5/2009 | Stearns et al. |
| 2009/0192444 A1 | 7/2009 | Albrecht et al. |
| 2009/0221960 A1 | 9/2009 | Albrecht et al. |
| 2009/0234293 A1 | 9/2009 | Albrecht et al. |
| 2009/0240204 A1 | 9/2009 | Taylor et al. |
| 2009/0264703 A1 | 10/2009 | Pribanic |
| 2009/0270681 A1 | 10/2009 | Moreno et al. |
| 2009/0270685 A1 | 10/2009 | Moreno et al. |
| 2009/0270813 A1 | 10/2009 | Moreno, Jr. et al. |
| 2009/0270817 A1 | 10/2009 | Moreno et al. |
| 2009/0281478 A1 | 11/2009 | Duke |
| 2009/0314422 A1 | 12/2009 | Racenet et al. |
| 2010/0022958 A1 | 1/2010 | Moreno, Jr. et al. |
| 2010/0185139 A1 | 7/2010 | Stearns et al. |
| 2010/0211049 A1 | 8/2010 | Schertiger et al. |
| 2010/0331822 A1 | 12/2010 | Willemstyn |
| 2011/0046449 A1 | 2/2011 | Minnelli et al. |
| 2011/0087159 A1 * | 4/2011 | Parihar ............... A61B 17/34 604/26 |
| 2011/0152775 A1 | 6/2011 | Lopez et al. |
| 2012/0140494 A1 | 6/2012 | Gu et al. |
| 2012/0330099 A1 | 12/2012 | Moreno et al. |

FOREIGN PATENT DOCUMENTS

| | | |
|---|---|---|
| DE | 19619065 A1 | 11/1997 |
| DE | 10330518 A1 | 2/2005 |
| EP | 0517248 A1 | 12/1992 |
| EP | 0567142 A2 | 10/1993 |
| EP | 0568383 A1 | 11/1993 |
| EP | 0570802 A1 | 11/1993 |
| EP | 0664101 A1 | 7/1995 |
| EP | 0696459 A1 | 2/1996 |
| EP | 0875256 A1 | 11/1998 |
| EP | 0890342 A1 | 1/1999 |
| EP | 0898 71 A2 | 3/1999 |
| EP | 0972493 A2 | 1/2000 |
| EP | 1210904 A2 | 6/2002 |
| EP | 0731718 B1 | 8/2002 |
| EP | 1312318 A1 | 5/2003 |

(56) References Cited

FOREIGN PATENT DOCUMENTS

| | | |
|---|---|---|
| EP | 1323373 A2 | 7/2003 |
| EP | 1348386 A1 | 10/2003 |
| EP | 0845960 B1 | 4/2004 |
| EP | 1459688 A1 | 9/2004 |
| EP | 1629787 A2 | 3/2006 |
| EP | 1679043 A1 | 7/2006 |
| EP | 1284664 B1 | 8/2006 |
| EP | 1698291 A1 | 9/2006 |
| EP | 1707133 A1 | 10/2006 |
| EP | 1707135 A1 | 10/2006 |
| EP | 1709918 A1 | 10/2006 |
| EP | 1834571 A1 | 9/2007 |
| EP | 1834573 A1 | 9/2007 |
| EP | 1994895 A1 | 11/2008 |
| GB | 2298906 A | 9/1996 |
| JP | 61-036718 A | 2/1986 |
| JP | 03-106329 A | 5/1991 |
| JP | 04-20324 | 1/1992 |
| JP | 06-133927 A | 5/1994 |
| JP | 06-169879 A | 6/1994 |
| JP | 06-304121 A | 11/1994 |
| JP | 07-178039 | 7/1995 |
| JP | 07-246187 | 9/1995 |
| JP | 07-289501 A | 11/1995 |
| JP | 07-313442 | 12/1995 |
| JP | 08-154888 | 6/1996 |
| JP | 08-173372 | 7/1996 |
| JP | 08-285001 | 11/1996 |
| JP | 10-43128 | 2/1998 |
| JP | 11-146882 | 6/1999 |
| JP | 2002-224014 A | 8/2002 |
| JP | 2002-238906 A | 8/2002 |
| JP | 2002282274 A | 10/2002 |
| JP | 2003-284686 A | 10/2003 |
| JP | 2004-016455 A | 1/2004 |
| JP | 2004-267583 A | 9/2004 |
| JP | 2005-253543 A | 9/2005 |
| JP | 2005319101 A | 11/2005 |
| JP | 2007117289 A | 5/2007 |
| JP | 04-158825 B2 | 10/2008 |
| JP | 04-170929 B2 | 10/2008 |
| JP | 3151790 U | 6/2009 |
| JP | 2009-189806 A | 8/2009 |
| JP | 04-329510 B2 | 9/2009 |
| JP | 2009-261953 A | 11/2009 |
| JP | 2009261923 A | 11/2009 |
| JP | 05-192294 B2 | 5/2013 |
| JP | 05-199979 B2 | 5/2013 |
| JP | 05-207962 B2 | 6/2013 |
| RU | 2014032 C1 | 6/1994 |
| WO | WO-94007552 A1 | 4/1994 |
| WO | WO-9532019 A1 | 11/1995 |
| WO | WO-96004946 A1 | 2/1996 |
| WO | WO-97040759 A1 | 11/1997 |
| WO | WO-98009673 A1 | 3/1998 |
| WO | WO-01089371 A1 | 11/2001 |
| WO | WO-02078527 A2 | 10/2002 |
| WO | WO-02096307 A2 | 12/2002 |
| WO | WO-03011154 A2 | 2/2003 |
| WO | WO-04043275 A1 | 5/2004 |
| WO | WO-05016133 A1 | 2/2005 |
| WO | WO-05030293 A2 | 4/2005 |
| WO | WO-05097019 A2 | 10/2005 |
| WO | WO-05097234 A2 | 10/2005 |
| WO | WO-08093313 A1 | 8/2008 |
| WO | WO-09005986 A1 | 1/2009 |

OTHER PUBLICATIONS

Extended European Search Report issued in European Application No. 12173277.0 dated Jul. 18, 2012.
Extended European Search Report issued in European Application No. 12173283.8 dated Jul. 18, 2012.
Extended European Search Report issued in European Application No. 12173290.3 dated Jul. 18, 2012.
International Search Report and Written Opinion issued in International Application No. PCT/US2010/042765 dated Oct. 13, 2010.
International Search Report and Written Opinion issued in International Application No. PCT/US2010/055905 dated Jan. 11, 2012.
Search report issued in European Application No. 09251196.3 dated Aug. 11, 2009.
Search report issued in European Application No. 09251201.1 dated Aug. 13, 2009.
Search report issued in European Application No. 09251208.6 dated Aug. 11, 2009.
Search report issued in European Application No. 09251210.2 dated Aug. 12, 2009.

* cited by examiner

SURGICAL ACCESS DEVICE

CROSS-REFERENCE TO RELATED APPLICATIONS

This application is a continuation of U.S. patent application Ser. No. 14/150,256, filed on Jan. 8, 2014 and entitled "Surgical Access Device," which is a continuation of U.S. patent application Ser. No. 12/902,265 (now U.S. Pat. No. 8,636,686), filed on Oct. 12, 2010 and entitled "Surgical Access Device," which is a continuation-in-part of U.S. patent application Ser. No. 12/533,590 (now U.S. Pat. No. 8,568,362), filed on Jul. 31, 2009 and entitled "Surgical Access Devices with Sorbents," which is a continuation-in-part of: U.S. patent application Ser. No. 12/110,724 (Now U.S. Pat. No. 8,579,807), filed on Apr. 28, 2008 and entitled "Absorbing Fluids in a Surgical Access Device," U.S. patent application Ser. No. 12/110,727 (now U.S. Pat. No. 8,870,747) filed on Apr. 28, 2008 and entitled "Scraping Fluid Removal in a Surgical Access Device," U.S. patent application Ser. No. 12/110,742 (now U.S. Pat. No. 9,358,041), filed on Apr. 28, 2008 and entitled "Wicking Fluid Management in a Surgical Access Device," and U.S. patent application Ser. No. 12/110,755 (Now U.S. Pat. No. 8,273,060), filed on Apr. 28, 2008 and entitled "Fluid Removal in a Surgical Access Device," all of which are hereby incorporated by reference in their entireties.

FIELD OF THE INVENTION

The present invention relates to methods and devices for performing surgical procedures, and in particular to methods and devices for maintaining visibility during surgical procedures.

BACKGROUND OF THE INVENTION

During laparoscopic surgery, one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. During such procedures, a scoping device, such as an endoscope or laparoscope, is inserted through one of the trocars to allow a surgeon to view the operative field on an external monitor coupled to the scoping device.

Scoping devices are often inserted and removed through a trocar multiple times during a single surgical procedure, and during each insertion and each removal they can encounter fluid that can adhere to the scopes lens and fully or partially impede visibility through the lens. Furthermore, a scope can draw fluid from inside or outside a patients body into the trocar, where the fluid can be deposited within the trocar until the scope or other instrument is reinserted through the trocar. Upon reinsertion, fluid can adhere to the scopes lens. The scopes lens thus needs to be cleaned to restore visibility, often multiple times during a single surgical procedure. With limited access to a scope in a body, each lens cleaning can require removing the scope from the body, cleaning the scope lens of fluid, and reintroducing the scope into the body. Such lens cleaning is a time-consuming procedure that also increases the chances of complications and contamination through repeated scope insertion and removal.

Accordingly, there is a need for methods and devices for maintaining clear visibility through a lens of a scoping device during a surgical procedure.

SUMMARY OF THE INVENTION

The present invention generally provides methods and devices for preventing fluid deposit onto and/or for removing fluid from a surgical instrument. In one embodiment, a surgical access device is provided and can include a housing defining a working channel sized and configured to receive a surgical instrument. An insufflation port can be formed in the housing and it can be configured to deliver an insufflation gas to the working channel. Further, a seal can be disposed within the housing and it can be positioned proximal to the insufflation port. In some embodiments, the seal can be configured to receive a surgical instrument passed through the working channel.

A fluid remover can be disposed within the housing and it can be positioned distal to the insufflation port. The fluid remover can have many configurations, for example, the fluid remover can have an outer perimeter mounted within the housing and a central opening configured to receive surgical instruments therethrough. In some embodiments, the outer perimeter can be in sealing engagement with the housing. The fluid remover can be configured to allow insufflation gas to pass therethrough when an instrument occludes the central opening. The fluid remover can be, for example, a scraper configured to scrape fluid away from surgical instruments inserted through the central opening.

In some embodiments, the scraper can include a wicking element formed thereon and configured to wick fluid away from the central opening in the scraper. The wicking element can have many different configurations, for example, the wicking element can be in the form of a plurality of channels formed in a distal surface of the scraper and extending radially outward from the central opening such that fluid scraped off of a surgical instrument can flow into the channels. The fluid remover can also include a sorbent disposed distal to the scraper and configured to receive fluid scraped by the scraper. In one embodiment, the fluid remover can include a hole formed therein and positioned a distance away from the central opening and the outer perimeter. The hole can be configured to allow insufflation gas to pass therethrough.

As will be appreciated by those having ordinary skill in the art, the housing can have many configurations. In one embodiment, the housing can include a proximal housing portion and a distal housing portion having a cannula extending distally therefrom. The proximal and distal housing portions can be disposed around an inner retainer, and the working channel can extend through the inner retainer and the cannula. The outer perimeter of the fluid remover can be in sealing engagement with the inner retainer and the distal housing portion. In some embodiments, the seal can be captured between the inner retainer and the proximal housing portion.

The distal cannula can include an angled distal surface having a distal-most point and a proximal-most point. In some embodiments, the distal-most point can be aligned with the insufflation port, although it can have any angular orientation as desired. The surgical access device can also include at least one opening formed on an outside wall of the housing that can be configured for receiving suture.

In other aspects, a surgical access device is provided and can include a housing and a cannula extending distally from the housing. The housing and the cannula can have a working channel extending therethrough between a proximal opening formed in a proximal end of the housing and a distal end of the cannula. The working channel can be sized and configured to receive a surgical instrument. An insufflation port can be coupled to the housing and configured to receive and deliver an insufflation gas to the working channel. Further, a seal can be disposed within the housing and configured to substantially prevent passage of an insufflation gas from the insufflation port to the proximal opening when no surgical instrument is disposed therethrough.

In some embodiments, a fluid remover can be disposed within the housing and can be positioned distal of the seal. The fluid remover can have an outer perimeter in sealing engagement with the housing. The fluid remover can also have a central opening formed therethrough positioned to receive a surgical instrument passed through the working channel. Further, the fluid remover can include a hole formed therein between the central opening and the outer perimeter that is configured to allow insufflation gas to pass from the insufflation port to the cannula when an instrument is disposed through and occludes the central opening in the fluid remover.

While the fluid remover can have many configurations, in one embodiment, the fluid remover can be a scraper configured to scrape fluid off of a surgical instrument passed through the opening. The surgical access device can also include a sorbent disposed within the housing at a location distal to the scraper. The sorbent can be configured to sorb fluid removed by the scraper. In some embodiments, the surgical access device can further include a wicking element formed on the scraper and configured to wick fluid away from the central opening in the scraper. The sorbent can have, for example, a central opening formed therethrough and can be axially aligned with the central opening in the scraper. In one embodiment, the central opening in the sorbent can have a diameter greater than a diameter of the central opening in the scraper. The insufflation port can be positioned anywhere within the housing, for example, the insufflation port can be positioned proximal to the fluid remover.

While the housing can have many configurations, in one embodiment, the housing can include a proximal housing portion and a distal housing portion disposed around an inner retainer. The working channel can extend through the inner retainer, and the outer perimeter of the fluid remover can be in sealing engagement with the inner retainer. The proximal opening can be formed in the proximal housing. In some embodiments, the inner retainer can be captured between the proximal and distal housing portions.

In further aspects, methods are also provided. For example, a method for removing fluid from a surgical access device is provided and can include inserting a surgical access device through tissue such that the surgical access device provides a working channel extending through the tissue and into a body cavity. Further, a surgical instrument can be inserted through the working channel of the surgical access device such that a central opening formed in a scraper disposed within the working channel engages a circumference of the surgical instrument. The method can further include delivering an insufflation gas through an insufflation port in the surgical access device to insufflate the body cavity. The insufflation gas can pass through a hole formed in the scraper.

In some embodiments, inserting a surgical instrument through the working channel of a surgical access device can include inserting a surgical instrument through a seal in a working channel of a surgical access device extending into a body cavity. The seal can move from a closed position in which the working channel is sealed to an open position as the surgical instrument is passed therethrough. Further, a fluid remover disposed distal of the seal can scrape fluid from the surgical instrument and invert proximally to transfer the fluid away from the surgical instrument. Fluid scraped by the scraper can be transferred to a sorbent.

In other aspects, a method for reprocessing a surgical access device is provided and includes removing a scraper from a surgical access device, cleaning the scraper, treating a surface of the scraper with a surfactant, and replacing the scraper in the surgical access device. In some embodiments, the surfactant can be dodecylbenzene sodium sulfonate or sodium dodecyl sulfate. In other embodiments, the scraper can be formed from a hydrophobic material such as a polyisoprene.

In still further aspects, a method for reprocessing a surgical access device is provided and includes removing a first sorbent from a surgical access device, treating a second sorbent with a surfactant, and replacing the first sorbent with the second sorbent in the surgical access device. In some embodiments, the surfactant can be dodecylbenzene sodium sulfonate or sodium dodecyl sulfate.

In another aspect, a fluid remover for use in a surgical access device is provided and can include a housing defining a working channel sized to receive a surgical instrument, an insufflation port disposed in the housing, and a seal disposed proximal to the insufflation port. In some embodiments, the fluid remover can include a fluid removing member having an outer perimeter and a central opening formed therein for receiving and sealing around a surgical access device. The fluid removing member can also have a hole disposed radially outward from the central opening and radially inward from the outer perimeter and can be configured to allow insufflation gas to pass therethrough.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
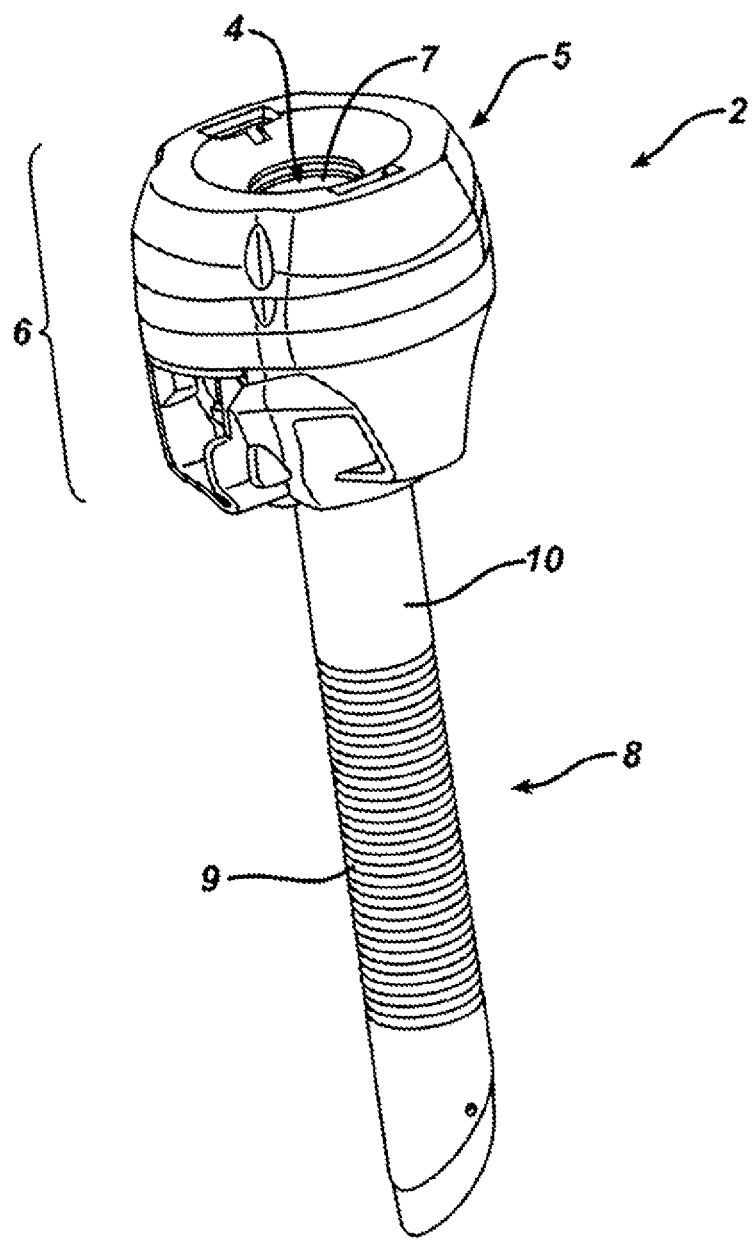
FIG. 1A is a perspective view of one embodiment of a trocar.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for maintaining clear visibility through a scoping device during surgical procedures, and in particular methods and devices are provided for removing fluid from an access device and/or surgical instrument passed, e.g., inserted and/or withdrawn, through an access device, and/or for preventing fluid from being transferred onto a scoping device passed through an access device. In certain exemplary embodiments, the methods and devices are effective to remove fluid from an access device and/or surgical instrument as the instrument is being withdrawn from the access device, thus preventing the fluid from being deposited onto an instrument being inserted through the access device. However, the methods and devices can be configured to remove fluid prior to and/or during insertion and/or removal.

A person skilled in the art will appreciate that the term fluid as used herein is intended to include any substance that, when on a surgical instrument, can adversely affect the functioning of the instrument or a surgeon's ability to use it. Fluids include any kind of bodily fluid, such as blood, and any kind of fluid introduced during a surgical procedure, such as saline. Fluids also include fluid/solid mixtures or fluids with particles (such as pieces of tissue) suspended or located therein, as well as viscous materials and gases. A person skilled in the art will also appreciate that the various concepts disclosed herein can be used with various surgical instruments during various procedures, but in certain exemplary embodiments the present invention is particularly useful during laparoscope procedures, and more particularly during procedures in which a scoping device, such as an laparoscope or endoscope, is passed through a surgical access device, such as a trocar, that provides a pathway from a skin incision to a body cavity. As previously explained, during such procedures repeated insertion and withdrawal of the scoping device can deposit fluid within the access device, thus allowing the fluid to be transferred back onto the distal viewing end of the scoping device upon reinsertion therethrough. Various exemplary methods and devices are provided herein to prevent such an occurrence.

In certain exemplary embodiments, the methods and devices disclosed herein utilize a fluid remover that is effective to remove fluid from an access device and/or surgical instrument passed therethrough. While the fluid remover can have various configurations and it can function in various manners to remove fluid, exemplary fluid removers include scrapers for scraping fluids, sorbents for sorbing fluid, and wicking elements for redirecting or wicking fluid away, e.g., by capillary action. Any combination of fluid removers can be provided, and the fluid removers can be disposed at various locations within an access device to remove fluid from portions of the access device and/or from surgical instruments, such as scoping devices, passed through the access device. The particular location of the fluid remover(s) can depend on the particular configuration of the access device and/or surgical instrument.

In certain exemplary embodiments, the fluid remover can include one or more sorbents. The sorbent can be any insoluble (or at least partially insoluble) material or mixture of materials that are capable of sorbing fluids or taking up fluids through a process of one or both of absorption and adsorption. A sorbent material or element can thus include any one of or combination of absorbent materials and/or elements and adsorbent materials and/or elements. In certain exemplary embodiments, the sorbent is formed from a hydrophilic material and/or includes a hydrophilic material to facilitate fluid receipt. For example, the sorbent can be coated using known coating techniques during manufacturing to render one or more portions of the sorbent hydrophilic. In one embodiment, the sorbent can be formed by an extrusion process in which, for example, the fibers can all extend longitudinally in a direction generally parallel to a longitudinal axis of the cylindrical tube, as shown in FIG. 30F. The fibers will thus form a generally cylindrical, hollow tubular member, which can subsequently be cut to form a plurality of sorbents. A sidewall gap or cut-out can also be made to form a C-shaped sorbent, or the sorbent can be formed to have a C-shaped configuration without the need to make any additional cuts. Exemplary shapes and configurations for the sorbent will be discussed in more detail below. A hydrophilic surfactant can be applied to the sorbent, either prior to or after the sorbent is cut. A person skill in the art will appreciate that a variety of techniques can be used to coat the sorbent or portions thereof with a hydrophilic material and/or to form the sorbent or portions thereof from a hydrophilic material. The particular hydrophilic material used can also vary, and exemplary materials will be discussed in more detail below with respect to the scraper. The same hydrophilic materials used with the scraper can also or alternatively be used with the sorbent.

In general, sorbents that are absorbents remove fluid through a process of absorption, similar to a sponge, in which a liquid diffuses into the volume and/or structure of the absorbent and becomes a part of that volume and/or structure. For example, the sorbent can pick up and retain a liquid distributed throughout its molecular structure causing the absorbent to swell. The liquid can cause the solid structure to swell 50% of more. Typical absorbents are at least 70% insoluble in excess fluid. Absorbents can have any shape, size, and form known in the art as needed to stand alone and/or fit within, around, or throughout any component of a fluid remover and/or trocar. Certain exemplary embodiments of absorbents include, but are not limited to, comminuted wood pulp fluff, cellulose fibers, polymeric gelling agents, hydrophilic non-wovens, cellulose, sodium polycrylate, cotton, polyethylene terephthalate, polyethylene, polypropylene, polyvinyl chloride, ABS, polyamide, polystyrene, polyvinyl alcohol, polycarbonate, ethylenemethacrylate copolymer, and polyacetal.

Sorbents that are adsorbents, on the other hand, remove fluid through a process of adsorption by retaining a liquid on their surface including pores and capillaries. Liquid accumulates on the surface of an adsorbent by forming a film of molecules or atoms that are retained thereon as a consequence of surface energy. In some embodiments, an adsorbent material can include one or more insoluble materials (or at least partially insoluble) that can be coated by a liquid on their surface. For example, the adsorbent can be a structure formed from insoluble fibers. The structure can be porous, as voids or spaces can be located between the individual fibers. Thus, liquid can accumulate on the surface of the fibers, thereby filling the voids between the fibers. Typical adsorbents will adsorb fluid without swelling more than 50% in excess liquid. Adsorbents can have any shape, size, and form known in the art as needed to stand alone and/or fit within, around, or throughout any component of a fluid remover and/or trocar. In an exemplary embodiment, the adsorbent is molded to have a predetermined shape and size. Certain exemplary adsorbent materials include, but are not limited to, oxygen-containing compounds, carbon-based compounds, and/or polymer based compounds, among others. For example, adsorbent materials can include silica gels, alumina, zeolites, activated carbon, graphite, cellulose, porous polymer matrices, perlite, metal hydroxides, metal oxidesellulose acetate, -butyrate and -nitrate, polyamide, polysulfone, vinyl polymers, polyesters, polyolefines and PTFE, as well as porous glass or glass ceramics, graphite oxide, polyelectrolyte complexes, alginate gel, etc.

Figure 1B:
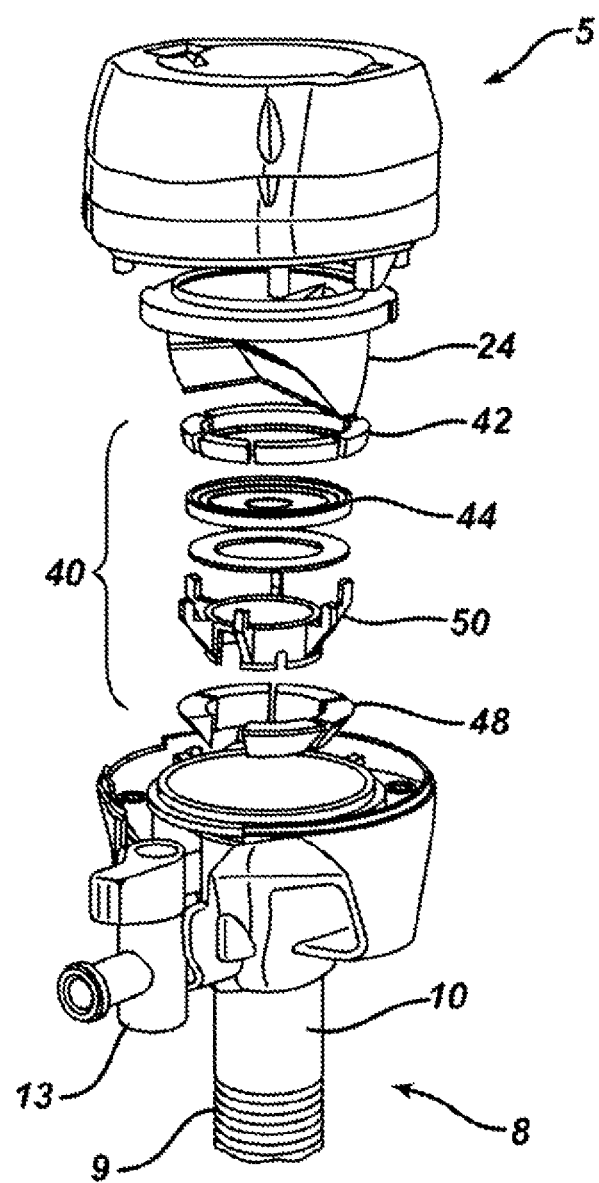
FIG. 1B is an exploded view of the trocar of FIG. 1A.
Figure 1C:
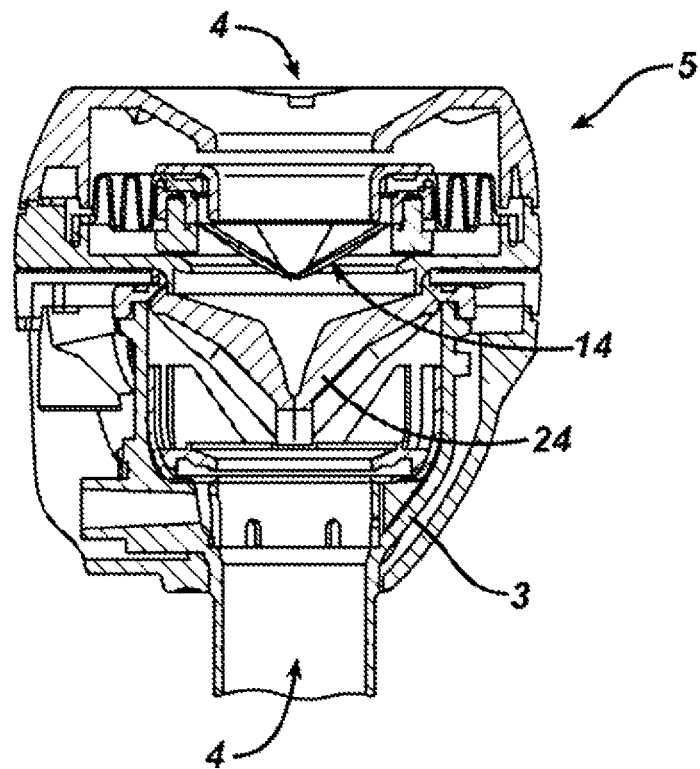
FIG. 1C is a cross-sectional view of a portion of the trocar of FIG. 1A.

While the fluid removers disclosed herein can be used with various surgical access devices known in the art, in certain exemplary embodiments a trocar is provided having one or more fluid removers disposed therein for removing fluid from portions of the trocar and/or from an instrument, such as a scoping device, passed therethrough. A person skilled in the art will appreciate that a trocar is shown for illustration purposes only, and that virtually any type of access device, including cannulas, ports, etc., can be used. FIGS. 1A-1C illustrate one exemplary embodiment of a trocar 2. As shown, the trocar 2 is generally in the form of a housing 6 having a proximal portion (also referred to herein as a proximal housing) that can house one or more sealing elements and a distal cannula 8 extending distally from the proximal housing 6. The trocar 2 defines a working channel 4 extending therethrough for introducing various instruments into a body cavity. A number of configurations are available for the proximal housing 6. In the illustrated embodiment, the proximal housing 6 has a generally cylindrical shape with a removable cap portion 5 and an inner sidewall 3. An opening 7 can be formed in the proximal end of the housing 6, such that the opening 7 extends through the removable cap 5 and through the remainder of the housing 6 and is coaxial with the working channel 4 extending through the cannula 8. The cannula 8 can also have various configurations, and can include various features known in the art. In the illustrated embodiment, the cannula 8 has a generally elongate cylindrical shape and includes a series of annular ridges 9 formed on an external surface 10 thereof. The opening 7 extending through the proximal housing 6 and the cannula 8 define the working channel 4 that is sized and configured to receive a surgical instrument. One skilled in the art will appreciate that the housing 6 and the cannula 8 can be formed as a unitary structure or as two separate components that are mated to one another. The housing 6 can also include other features, such as a stop-cock valve 13 for allowing and preventing the passage of an insufflation fluid, e.g. carbon dioxide, through the trocar 2 and into a body cavity.

In use, the distal cannula 8 can be inserted through a skin incision and through tissue to position a distal-most end within a body cavity. The proximal housing 6 can remain external to the body cavity, and various instruments can be inserted through the working channel 4 and into the body cavity. Typically, during surgical procedures in a body cavity, such as the abdomen, insufflation is provided through the trocar 2 to expand the body cavity to facilitate the surgical procedure. Thus, in order to maintain insufflation within the body cavity, most trocars include at least one seal disposed therein to prevent air from escaping. Various seal configurations are known in the art, but typically the trocar 2 includes an instrument seal that forms a seal around an instrument disposed therethrough, but otherwise does not form a seal when no instrument is disposed therethrough; a channel seal (also referred to herein as a zero-closure seal) that seals the working channel 4 when no instrument is disposed therethrough; or a combination instrument seal and channel seal that is effective to both form a seal around an instrument disposed therethrough and to form a seal in the working channel 4 when no instrument is disposed therethrough. In the embodiment shown in FIGS. 1A-1C the trocar 2 includes an instrument seal 14 and a separate channel or zero-closure seal 24. However, a person skilled in the art will appreciate that various other seals known in the art can be used including, for example, flapper valves, gel seals, diaphragm seals, etc.

Figure 1D:
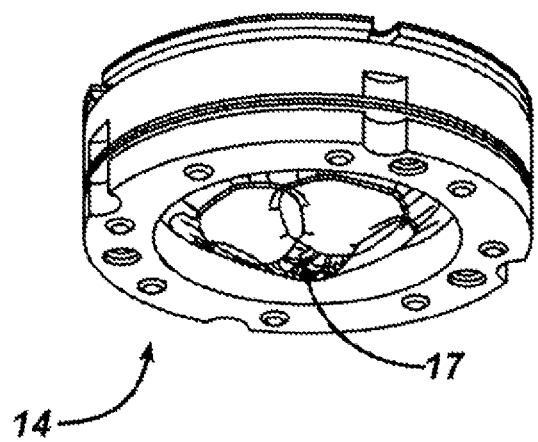
FIG. 1D is a bottom perspective view of an instrument seal assembly for use with the trocar of FIG. 1A.
Figure 1E:
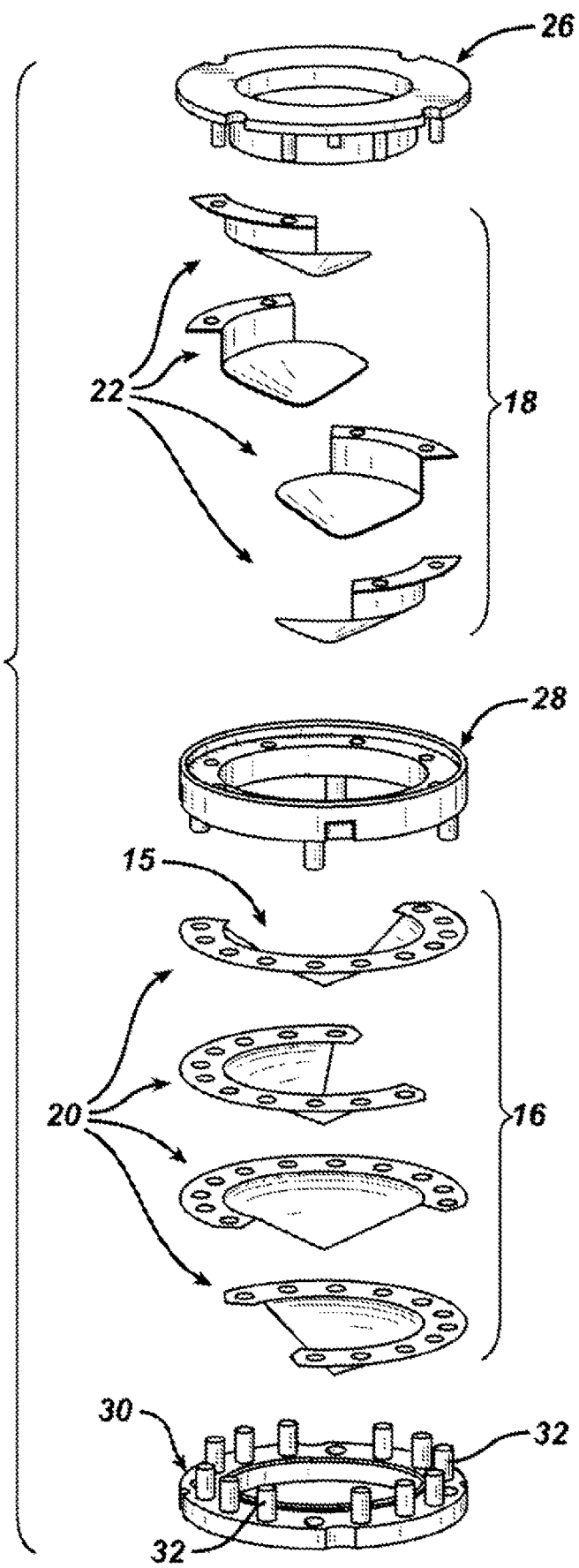
FIG. 1E is an exploded view of the instrument seal assembly of FIG. 1D.

In an exemplary embodiment, as shown in FIGS. 1C-1E, the instrument seal 14 is generally in the form of a multi-layer conical seal 16 and a multi-layer protective member 18 disposed on a proximal surface 15 of the seal 16. As best shown in FIG. 1E, the multi-layer conical seal 16 can include a series of overlapping seal segments 20 that are assembled in a woven arrangement to provide a complete seal body. The seal segments 20 can be stacked on top of one another or woven together in an overlapping fashion to form the multi-layer seal 16 having a central opening 17 therein. The seal segments 20 can be made from any number of materials known to those skilled in the art, but in an exemplary embodiment the seal segments 20 are formed from an elastomeric material. The seal segments 20 can also be molded such that they have a varying thickness across the profile of the seal 16. Varying the thickness across to the profile of the seal 16 can be effective to minimize leakage and reduce drag forces on the instrument. The multi-layer protective member 18 can similarly be formed from a series of overlapping segments 22 that are disposed proximal to the overlapping seal segments 20 and that are configured to protect the seal segments 20 from damage caused by surgical instruments passed through the opening 17 in the seal 16. The protective member 18 can also be formed from various materials, but in certain exemplary embodiments the protective member 18 is formed from a molded thermoplastic polyurethane elastomer, such as Pellethane™. The segments 20, 22 that form the seal 16 and the protective member 18 can be held together using various techniques known in the art. As shown in FIGS. 1D and 1E, the segments 20, 22 are held together by several ring members that mate to engage the segments 20, 22 therebetween. In particular, the protective member 18 is engaged between a crown 26 and a gasket ring 28, and the seal 16 is engaged between the gasket ring 28 and a retainer ring 30. Pins 32 are used to mate the ring members 26, 28 and to extend through and engage the segments of the seal 16 and protective member 18.

When fully assembled, the instrument seal 14 can be disposed at various locations within the trocar 2. In the illustrated embodiment, the instrument seal 14 is disposed in the cap 5 of the trocar 2 at a location just distal of the proximal opening 7 and proximal of a channel seal, as discussed in more detail below. In use, an instrument can be passed through the center of the seal assembly and the seal segments 20, 22 can engage and form a seal around an outer surface of the instrument to thereby prevent the passage of fluids through the seal 14. When no instrument is disposed therethrough, the opening will not form a seal in the working channel 4, however other configurations in which a seal is formed when no instrument is disposed therethrough are also conceivable. Exemplary instrument seal configurations are described in more detail in U.S. Publication No. 2004/0230161 entitled "Trocar Seal Assembly," filed on Mar. 31, 2004, and U.S. application Ser. No. 10/687,502 entitled "Conical Trocar Seal," filed on Oct. 15, 2003, which are hereby incorporated by reference in their entireties.

Figure 1F:
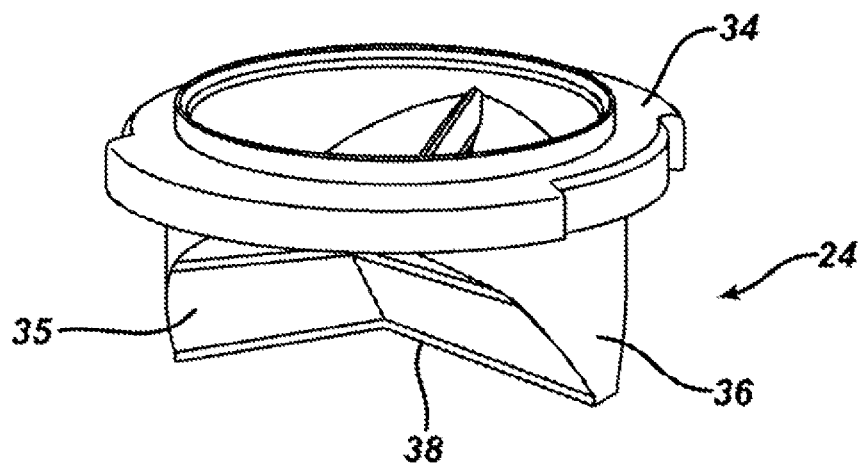
FIG. 1F is a perspective view of a channel seal of the trocar of FIG. 1A.

The zero-closure seal in the illustrated embodiment is shown in more detail in FIG. 1F, and as shown the illustrated zero-closure seal is in the form of a duckbill seal 24. The seal 24 is configured to form a seal in the working channel 4 when no instrument is disposed therethrough to thus prevent the leakage of insufflation gases delivered through the trocar 2 to the body cavity. As shown, the duckbill seal 24 has a generally circular flange 34 with a sidewall 36 extending distally therefrom. The shape of the sidewall 36 can vary, but in the illustrated embodiment, the sidewall 36 includes opposed flaps 35 that extend at an angle toward one another in a distal direction and that come together at a distal end to form a seal face 38. The opposed flaps 35 are movable relative to one another to allow the seal face 38 to move between a closed position, in which no instrument is disposed therethrough and the seal face 38 seals the working channel 4 of the trocar 2, and an open position in which an instrument is disposed therethrough. The seal can include various other features, as described in more detail in U.S. application Ser. No. 11/771,263, entitled "Duckbill Seal with Fluid Drainage Feature," filed on Jun. 29, 2007, which is hereby incorporated by reference in its entirety.

In accordance with the present disclosure the general structure of the seals as well as the trocar do not generally form part of the present invention. As such, a person skilled in the art will certainly appreciate that various seal configurations, as well as various trocars, can be used without departing from the spirit of the invention disclosed herein.

As indicated above, a fluid remover can be disposed within the trocar 2 to remove fluid from a seal and/or from a surgical instrument extending through the seal. As best shown in FIGS. 1B-1C, the illustrated trocar 2 includes a fluid remover assembly 40 that is disposed within the proximal housing 6 of the trocar 2 at a location distal of the duckbill seal 24. The fluid removal assembly 40 includes a scraper for scraping fluid off of a surgical instrument passed through the working channel 4 in the trocar 2, and a sorbent for sorbing removed fluid. The scraper can also include a wicking feature for wicking fluid away from the opening in the scraper, and/or the sorbent can include a wicking feature for wicking fluid away from the scraper.

Figure 1G:
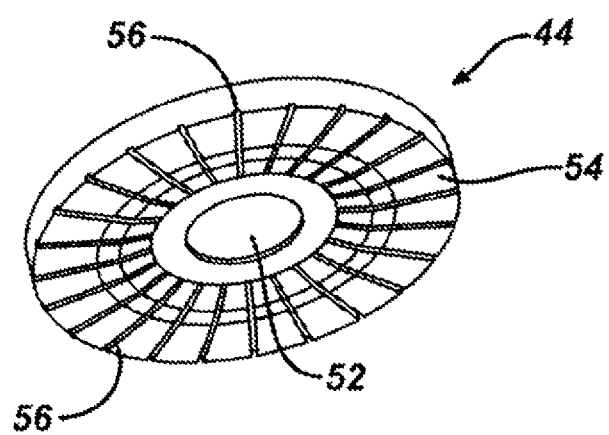
FIG. 1G is a bottom perspective view of one embodiment of a scraper of a fluid remover assembly for use with the trocar of FIG. 1A.
Figure 1H:
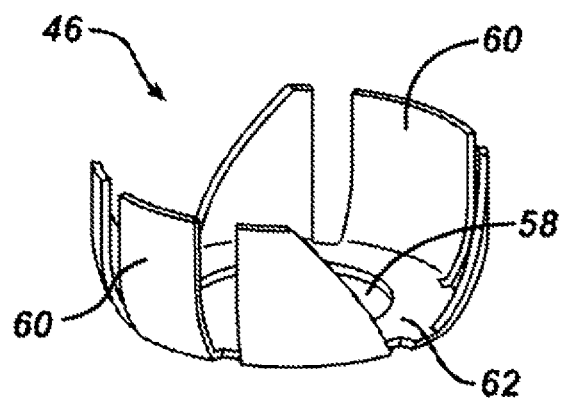
FIG. 1H is a perspective view of one embodiment of a sorbent wick of a fluid remover assembly for use with the trocar of FIG. 1A.
Figure 1I:
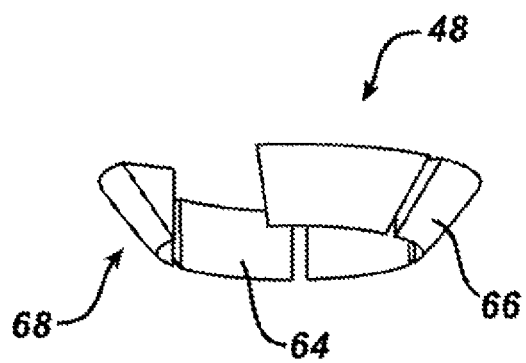
FIG. 1I is a perspective view of a sorbent element of a fluid remover assembly for use with the trocar of FIG. 1A.
Figure 1J:
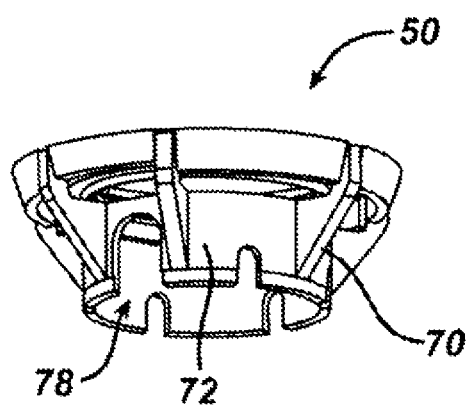
FIG. 1J is a perspective view of a frame for housing the sorbent element of FIG. 1I.
Figure 1K:
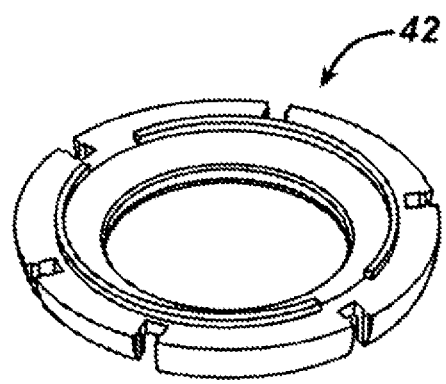
FIG. 1K is a perspective view of a lid portion of a fluid remover assembly for use with the trocar of FIG. 1A.

The components of the fluid remover assembly 40 are shown in more detail in FIGS. 1G-1K, and as shown the assembly generally includes a lid 42 (FIG. 1K), a scraper 44 (FIG. 1G), a sorbent wick 46 (FIG. 1H), sorbent cartridges 48 (FIG. 1I), and a housing or frame 50 (FIG. 1J). When fully assembled, the fluid remover assembly 40 is configured to scrape fluid off of surgical instruments passing through the working channel 4 of the trocar 2, to wick the scraped fluids away, and to sorb them, thereby preventing the fluids from being redeposited on the instrument upon reinsertion through the working channel.

Referring first to FIG. 1G, the scraper 44 can have a variety of configurations, but in an exemplary embodiment, as shown, the scraper has a generally planar configuration with a circular shape. A central opening 52 is formed through a central portion thereof and is sized and configured to receive a surgical instrument therethrough. In use, the central opening 52 can be coaxial with openings in the instrument and channel seals. The scraper 44 can be formed from various materials, but in an exemplary embodiment the scraper is formed from polyisoprene to allow the scraper 44 to engage and scrape fluid off of any instrument passed therethrough. As further shown in FIG. 1G, a distal-facing surface 54 of the scraper 44 can include a plurality of channels 56 formed therein and extending radially outward from the central opening 52, or from a location just radially outward but adjacent to the central opening 52. The channels 56 can be configured such that fluid scraped off of an instrument by the central opening 52 will flow into the channels 56 and thereby be wicked away from the opening 52.

As indicated above, the fluid remover assembly 40 can also include a sorbent wick 46. As shown in FIG. 1H, in an exemplary embodiment the sorbent wick 46 has a generally planar circular portion 62 with a central opening 58 formed therethough. The central opening 58 can have a diameter slightly larger than a diameter of the central opening 52 in the scraper 44, and it can be configured to be positioned coaxial with the opening 52 in the scraper 44. As further shown in FIG. 1H, the sorbent wick 46 can also include one or more sidewalls 60 extending from the planar circular portion 62. The illustrated sidewalls 60 extend proximally, however they can extend distally depending on the particular configuration of the wick 46. The sidewalls 60 can be configured to sit within the inner sidewall 3 of the trocar housing 6. In use, the sorbent wick 46 can wick and sorb fluid away from the central opening 52 in the scraper 44, and it can deliver the fluid to the sorbent cartridges 48, as discussed in more detail below. The sorbent wick 46, as well as various other sorbent members disclosed herein, can be formed from a variety of sorbent materials as described above.

The sorbent cartridges 48 are shown in more detail in FIG. 1I, and as shown the cartridges 48 each have a generally semi-circular shape with a width, as measured from an internal surface 64 to an external surface 66, that decreases in a proximal to distal direction to form wedge-shaped members 68. Together, the cartridges 48 can have an annular configuration. In use, the cartridges 48 can sorb fluid from the sorbent wick 46, thereby storing the fluid at a location away from any instrument passed through the working channel 4. The cartridges 48 can be contained within the trocar 2 by a housing or frame 50, as shown in FIG. 1J. The frame 50 can have a generally cylindrical configuration with an opening 68 extending therethrough, and a plurality of ridges 70 protruding radially outward and extending axially along an outer surface 72 thereof. Each sorbent cartridge 48 can be seated between two ridges. In use, the frame 50 can be particularly advantageous as it can protect the sorbent from being contacted by instruments passing through the working channel.

When fully assembly, the scraper 44 can be seated within the sorbent wick 46, which can rest on top of the frame 50 that holds the sorbent cartridges 48. The lid 42, shown in FIG. 1K, can be seated on top of the scraper 44 and within the sorbent wick 46, and the lid 42 can lock onto the frame 50, thereby holding the fluid remover assembly 40 together. Referring to FIG. 1C, the entire assembly 40 can be seated within the proximal housing 6 of the trocar 2 just distal of the duckbill seal 24. As a result, when an instrument, such as a scoping device, is passed through the working channel 4 of the trocar 2, any fluid on the instrument will be scraped off of the sidewalls of the instrument by the scraper 44. The fluid will flow through the channels 56 and/or be wicked away from the opening 52 by the sorbent wick 46, which delivers the fluid to the sorbent cartridges 48. As a result, when the instrument is withdrawn, for example, the fluid will be prevented from being deposited onto the instrument seal 14, thereby preventing the fluid from being transferred from the instrument seal 14 back onto the instrument upon reinsertion.

Figure 2A:
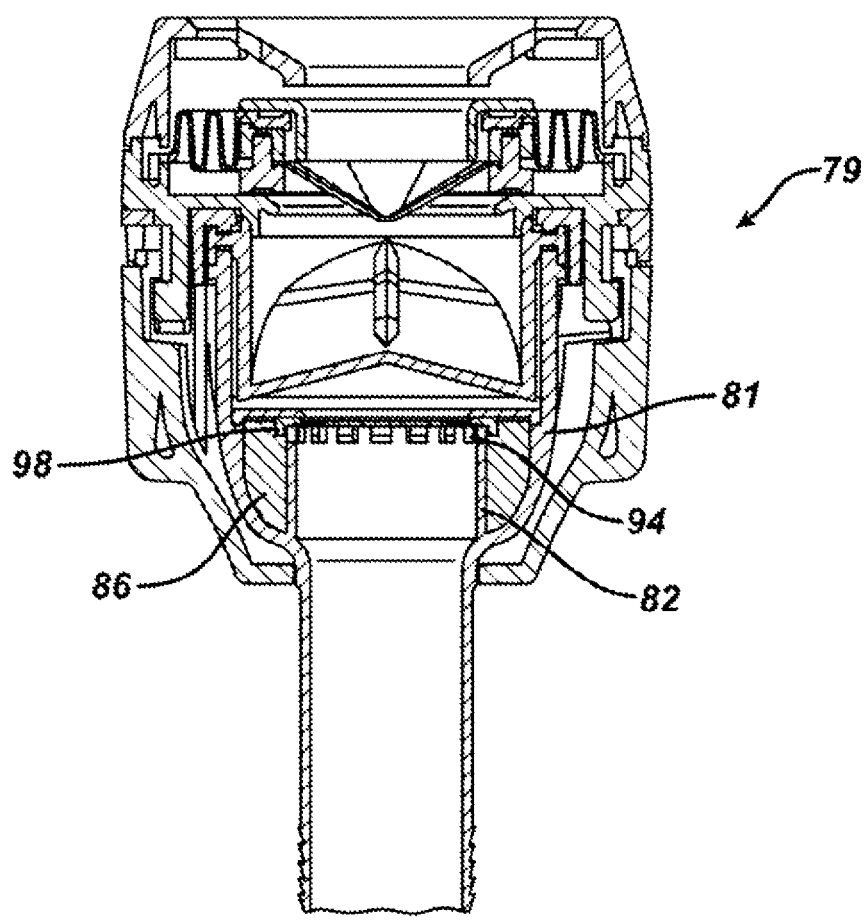
FIG. 2A is a cross-sectional view of a proximal portion of another embodiment of a trocar.
Figure 2B:
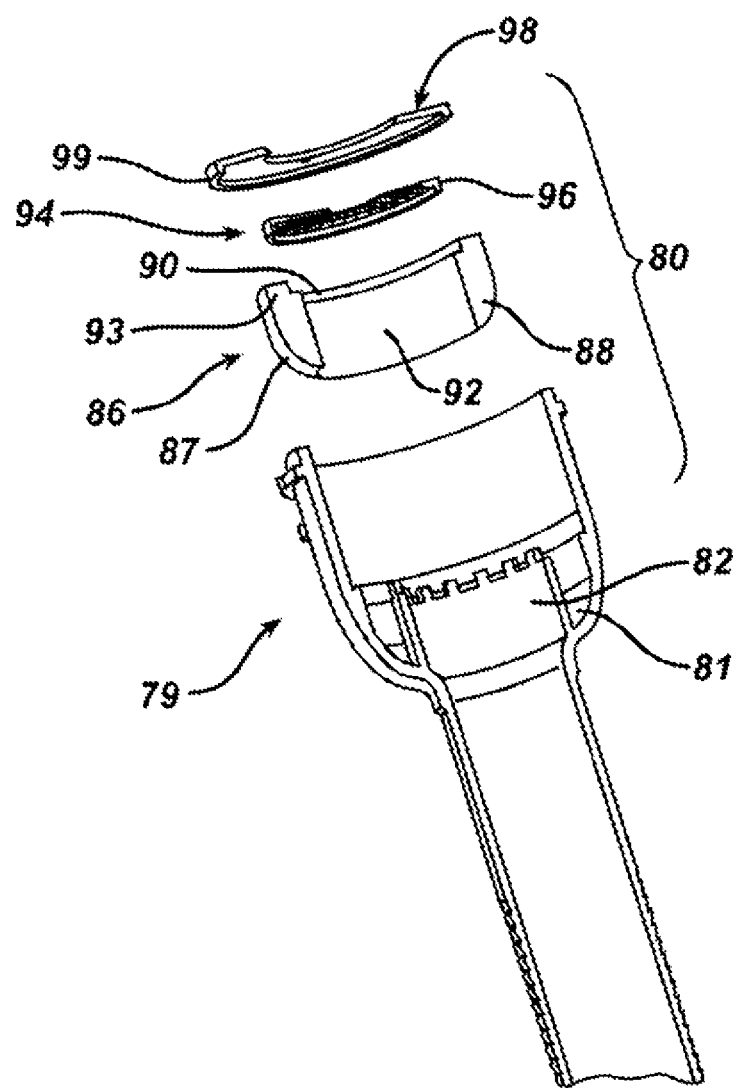
FIG. 2B is an exploded view of the trocar of FIG. 2A.

FIGS. 2A-2B illustrate yet another embodiment of a fluid remover assembly 80 that is similar to the embodiment shown in FIG. 1A. In this embodiment, the proximal housing 79 of the trocar has a frame 82 that is molded into the inner sidewall 81 of the housing 79 for directly seating a sorbent, a scraper, and a lid, thereby eliminating the need for the frame 50 of FIG. 1J. A single sorbent element 86 is also provided, rather than a sorbent wick and separate sorbent cartridges. In particular, the sorbent element 86 in this embodiment has a generally cylindrical configuration with a distal portion 88 that tapers inward on an outer surface 87 thereof to conform to the inner surface 81 of the proximal housing 79 of the trocar. A recess 90 can be formed around an inner surface 92 of a proximal end 93 of the sorbent element 86 to seat a scraper 94, which can have a configuration that is the same as or similar to the scraper 44 described above with respect to FIG. 1G. The recess 90 can engage an outer perimeter 96 of the scraper 94 such that the channels 56 on the scraper 94 can deliver fluid away from the opening 52 in the scraper 94 to the sorbent element 86 surrounding the scraper 94. A cap 98 can sit on top of the scraper 94 and can include a flange 99 that extends around the proximal end 93 of the sorbent element 86. The cap 98 can engage the inner sidewall 81 of the proximal housing 79 of the trocar to retain the scraper 94 and sorbent element 86 therein at a location just distal of the duckbill seal 24. In use, instruments passed through the working channel 4 of the trocar will be engaged by the scraper 94, which scrapes fluid off of the outer surface of the instrument. The fluid is wicked away from the opening 52 in the scraper 94 by the channels 56, which deliver the fluid to the sorbent element 86 surrounding the scraper 94. Thus, similar to the embodiment of FIG. 1A, when the instrument is withdrawn, for example, the fluid will be prevented from being deposited onto the seals, and in particular the instrument seal 14, thereby preventing the fluid from being transferred from the instrument seal 14 back onto the instrument upon reinsertion.

A person skilled in the art will appreciate that the fluid remover assemblies 40, 80 can have a variety of other configurations. FIGS. 3A-10B illustrate additional exemplary embodiments of fluid removers, e.g., scrapers, sorbents, and wicking elements, or combinations thereof. In these embodiments, the fluid removers are all located distal of the channel seal, e.g., duckbill seal or other zero-closure seal, and distal of the instrument seal 14. However a person skilled in the art will appreciate that the particular location of the fluid remover can vary and the fluid removers can be positioned anywhere within the trocar.

Figure 3A:
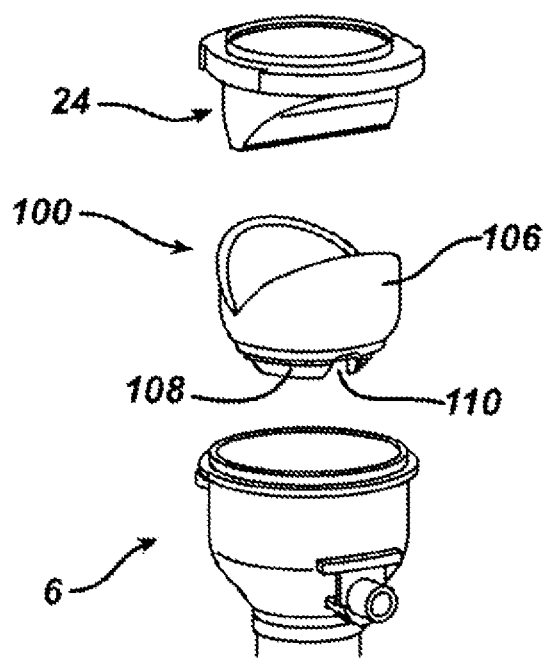
FIG. 3A is an exploded view of a portion of a trocar having a drop-in fluid remover assembly.
Figure 3B:
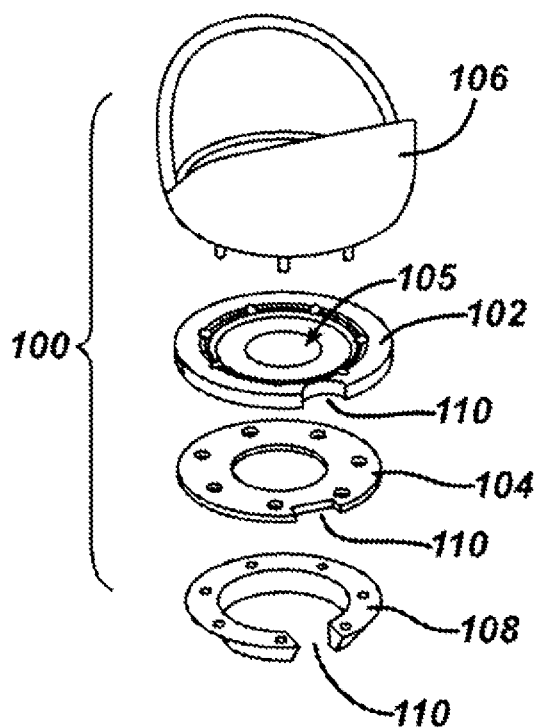
FIG. 3B is an exploded view of the drop-in fluid remover assembly of FIG. 3A.
Figure 3C:
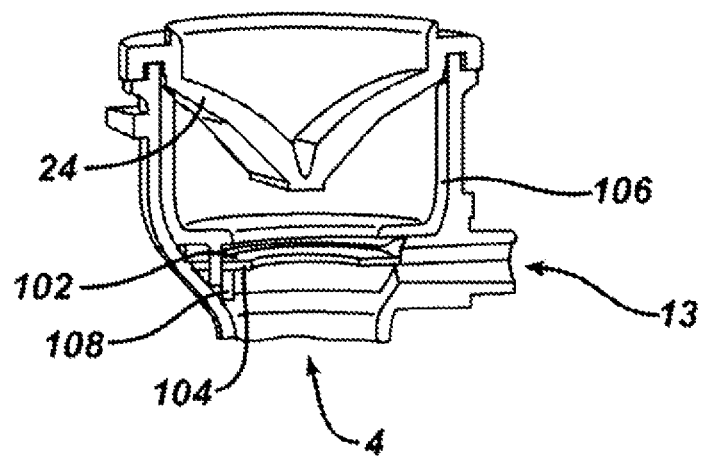
FIG. 3C is a cross-sectional view of a trocar of FIG. 3A.

FIGS. 3A-3C illustrate one embodiment of a fluid remover assembly 100 having a scraper and a sorbent. In particular, as best shown in FIG. 3B, the fluid remover assembly 100 can include a stabilization cup 106 coupled to a flange 108. The stabilization cup 106 can be formed from a sorbent material and the flange 108 can seat the cup 106 within the proximal housing 6 of the trocar 2, as shown in FIG. 3C. A scraper element in the form of a scraper disc 102 can be positioned between the flange 108 and the stabilization cup 106, and a sorbent ring 104 can be coupled to a distal surface 103 of the scraper disc 102. The scraper disc 102 can have a central opening 105 extending therethrough and configured for scraping fluid off of surgical instruments passed through the working channel 4 of the trocar 2. As an instrument is passed through the working channel 4, fluid can be scraped by the scraper disc 102 and sorbed by the sorbent ring, as well as by the stabilization cup. As can be seen in FIG. 3B, the flange 108, scraper disc 102, and sorbent ring 104 can each optionally include cut-outs 110 to fit around the stop-cock 13 associated with the trocar 2. In use, the fluid remover assembly 100 can be formed as a drop-in unit that fits within the proximal housing 6 of the trocar 2. As shown in FIG. 3C, the assembly 100 can be seated in a distal portion of the proximal housing 6 at a location just distal of the duckbill seal 24. The fluid remover assembly 100 will thus remove fluid from instruments passed through the working channel 4 of the trocar, thereby preventing fluid from being deposited onto the seals, and in particular the instrument seal 14, and/or redeposited onto instruments passed through the working channel 4.

Figure 4A:
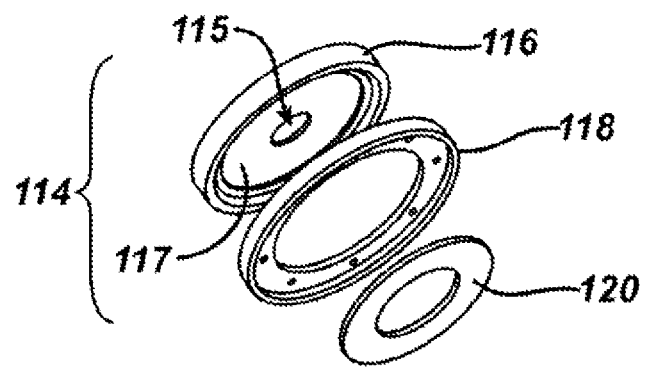
FIG. 4A is an exploded view of one embodiment of a scraper assembly for scraping fluid.
Figure 4B:
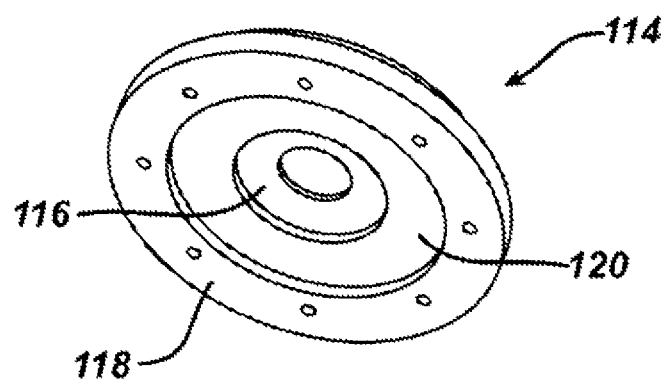
FIG. 4B is a bottom perspective view the scraper assembly of FIG. 4A.
Figure 4C:
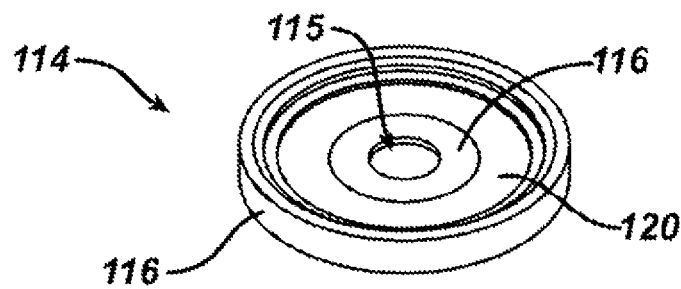
FIG. 4C is a top perspective view of the scraper assembly of FIG. 4A.

FIGS. 4A-4C illustrate another embodiment of a fluid remover assembly 114 that is similar to the assembly shown in FIGS. 3A-3C, however in this embodiment the assembly 114 does not include a stabilization cup. As shown, the fluid remover assembly includes a substantially planar circular scraper disc 116 having a central opening 115 for receiving a surgical instrument. The scraper disc 116 can be seated within a flange or retainer ring 118 configured to be positioned within the proximal housing of a trocar. A sorbent ring 120 can be positioned adjacent to a distal surface 117 of the scraper disc 116 and it can act to sorb any fluid that is scraped off of instruments passed through the scraper disc 116. When disposed within a trocar, the flange 118 can act as a support structure to hold the scraper disc 116 and the sorbent ring 120 in a fixed position within the proximal housing. While the position can be distal to the duckbill seal, as indicated above the assembly can be located at various other portions within the trocar, including between the duckbill seal and the instrument seal, proximal to the instrument seal, or within any portion of the cannula.

Figure 5A:
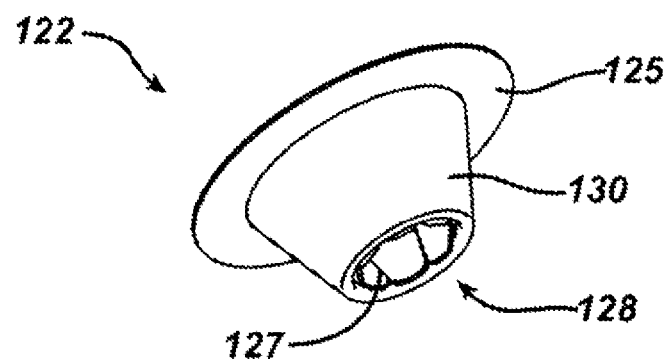
FIG. 5A is a perspective view of another embodiment of fluid remover assembly having a scraper nested within a sorbent element.
Figure 5B:
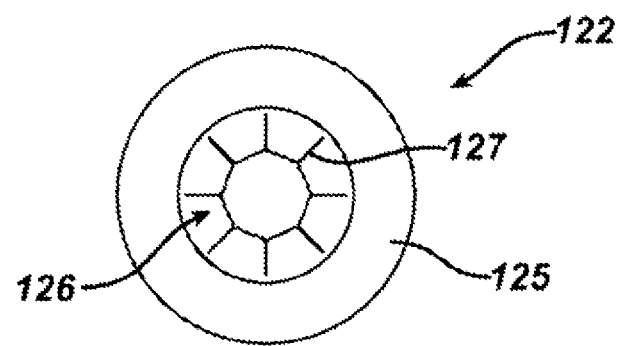
FIG. 5B is top view of the fluid remover assembly of FIG. 5A.
Figure 5C:
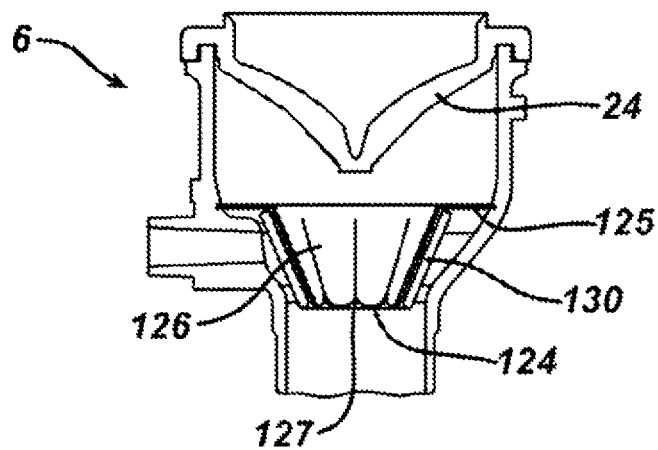
FIG. 5C is a cross-sectional view of the fluid remover assembly of FIG. 5A disposed within a trocar housing.

In another embodiment, shown in FIGS. 5A-5C, a fluid remover assembly 122 is provided and can have a generally conical configuration with a scraper 124 having a proximal generally planar flange 125 and a conical body 126 extending distally therefrom and defining a central opening 128. The conical body 126 can have a plurality of slits 127 extending proximally from a distal end thereof and designed to reduce insertion and withdrawal forces on a surgical instrument passed therethrough. The conical body 126 can be surrounded by a conical sorbent element 130 such that the conical body 126 is nested within the conical sorbent element 130. When assembled and disposed within a trocar, as shown in FIG. 5C, the flange 125 can be seated within the proximal housing 6 just below the duckbill seal 24 and it can mate to or engage the inner sidewall of the housing 6 to retain the fluid remover assembly therein. In use, as an instrument is passed through the working channel, the scraper 124 can engage and scrap fluid off of the instrument and the sorbent element 130 can sorb the fluid. A person skilled in the art will appreciate that any number of geometries can be used in a similar way. Also, a size or diameter of a flange can be adjusted as needed, or the flange can be removed, to seat the fluid remover assembly at other locations within the trocar.

Figure 6C:
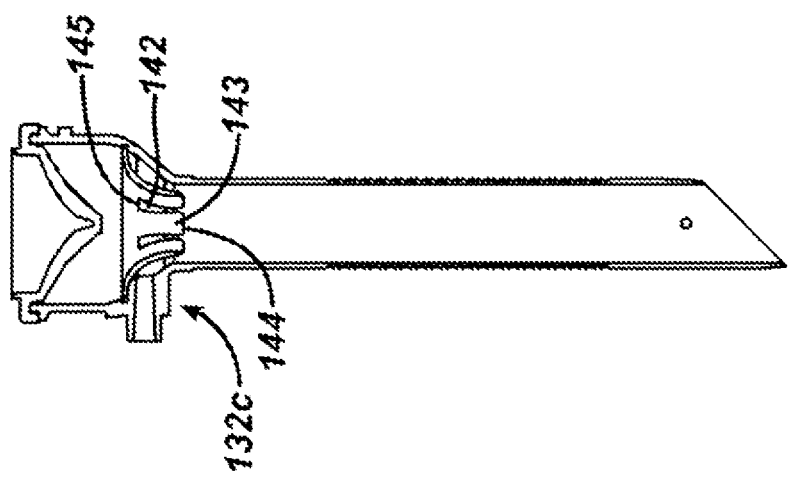
FIG. 6C is a cross-sectional view of a trocar having yet another embodiment of a scraper for scraping fluid away from a surgical instrument passed therethrough.
Figure 6B:
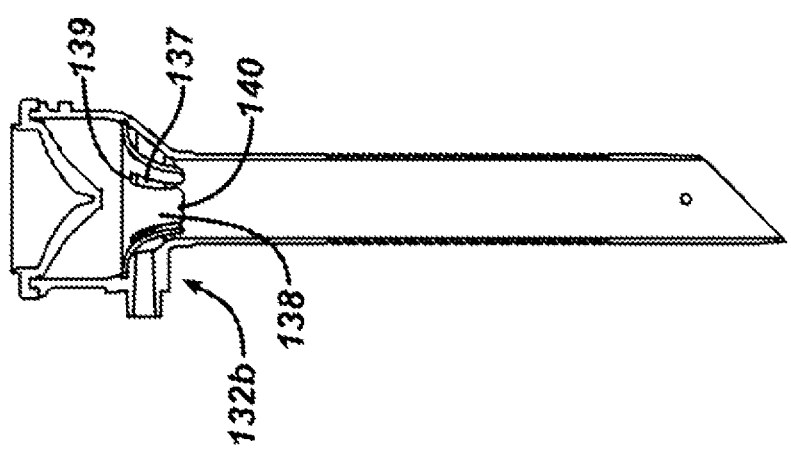
FIG. 6B is a cross-sectional view of a trocar having another embodiment of a scraper for scraping fluid away from a surgical instrument passed therethrough.
Figure 6A:
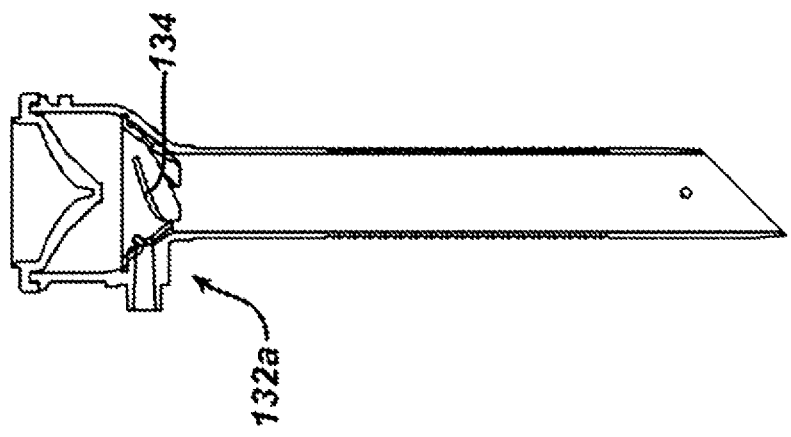
FIG. 6A is a cross-sectional view of a trocar having one embodiment of a scraper for scraping fluid away from a surgical instrument passed therethrough.

FIGS. 6A-6C illustrate additional embodiments of conical scrapers 132a, 132b, 132c that are similar to the scraper 124 described above and shown in FIGS. 5A-5C. As with the previous embodiment, the scrapers 132a, 132b, 132c in FIGS. 6A-6C are positioned distal to the duckbill seal 24. Such a configuration can prevent fluid on instruments being inserted and/or withdrawn from being deposited onto the duckbill seal, as well as the more-proximally located instrument seal 14. In an exemplary embodiment, each scraper 132a, 132b, 132c can be made from a pliable material and can include at least one slit formed therein and configured to allow the scrapers 132a, 132b, 132c to radially expand. A variety of configurations are available for the slit(s). In the embodiment shown in FIG. 6A, a single slit 134 extends diagonally around the scraper 132a such that the slit 134 follows the shape of the cone. In another embodiment shown in FIG. 6B, multiple slits 137 extend proximally from the distal end of the cone and terminate at a location 139 just distal to the proximal end. Such a configuration can yield a scraper having multiple scraping segments 138. As further shown in FIG. 6B, each scraping segment 138 can also include a notch or cut-out 140 formed in an outer surface at the distal end thereof to allow the segment 138 to expand and contact as instruments are passed therethrough. FIG. 6C illustrates another exemplary embodiment of a cone shaped scraper 132c. Similar to the scraper 132b shown in FIG. 6B, the scraper 132c includes several slits 142 that extend proximally from the distal end thereof. In this embodiment, however, the slits 142 increase in width in a distal to proximal direction such that each scraping segment 143 has a distal end 144 with a width that is greater than a width of a proximal end 145 thereof. As indicated above, in use the slit(s) 134, 137, 142 formed in the scrapers 132a, 132b, 132c allow the scrapers to radially expand as a surgical instrument is passed therethrough, thus accommodating instruments of various sizes while still being effective to scrape fluid off of the instruments.

Figure 7:
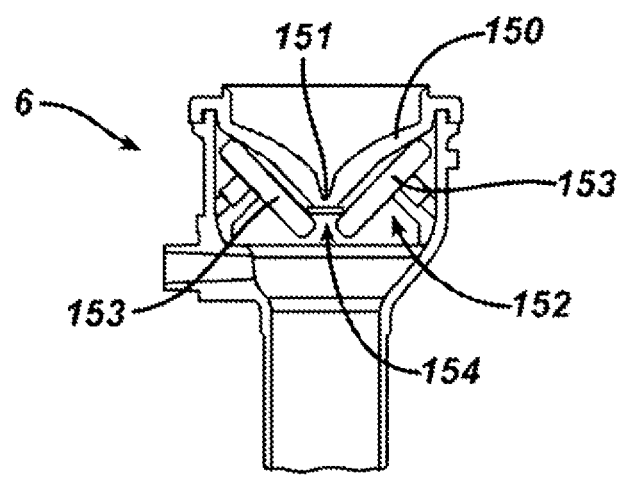
FIG. 7 is a cross-sectional view of another embodiment of a trocar housing having sorbent flapper doors positioned adjacent to a zero-closure seal.

FIG. 7 illustrates another embodiment of a fluid remover positioned just distal of a channel seal, e.g., duckbill seal 150, in a proximal housing of a trocar. In this embodiment, the fluid remover is in the form of sorbent flapper doors 152. The flapper doors 152 can have various shapes and sizes, and they can be formed from any number of components. For example, the flapper doors 152 can be in the form of two sidewalls 153 that are movable relative to one another. The sidewalls 153 can have a profile that is similar to the profile of the duckbill seal 150. In other embodiments, the flapper doors 152 can have a shape that corresponds to the shape of the duckbill seal 150. A person skilled in the art will appreciate that various configurations are possible. The flapper doors 152 can be seated inside the proximal housing 6 and attached to the housing 6 by any attachment means known in the art, including by mechanical means, adhesives, etc. The flapper doors 152 can define an opening 154 therebetween for receiving a surgical instrument, and the opening 154 can be positioned just distal of the seal face 151. In use, the flapper doors 152 can move from a closed or substantially closed position to an open position as an instrument is passed through the duckbill seal 150 and the flappers door 152. The doors 152 can contact and engage the surgical instrument as it is being passed therethrough to sorb fluids off of the instrument. The flapper doors 152 can also sorb any excess fluid that is scraped off of the instrument by the duckbill seal 150 and that falls distally from the duckbill seal 150.

Figure 8:
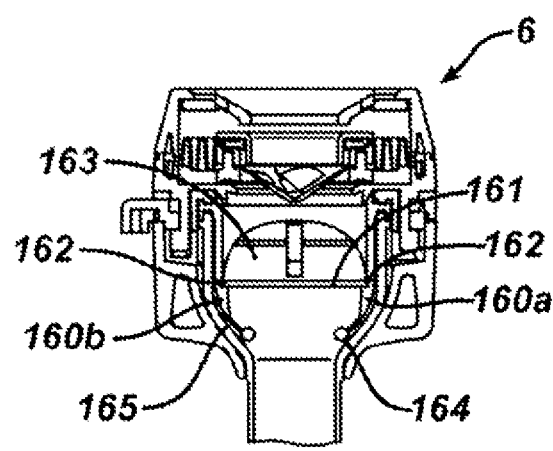
FIG. 8 is a cross-sectional view of yet another embodiment of a trocar housing having wicking fingers coupled to a sorbent reservoir.

In a similar embodiment, shown in FIG. 8, the fluid remover can be in the form of a wicking element rather than a sorbent. In the illustrated embodiment, the wicking element is in the form of first and second wicking fingers 160a, 160b that are coupled to opposed outer edges 162 of the seal face 161 on the duckbill seal 163. The wicking fingers 160a, 160b can be in the form of elongate members that follow the natural shape of the inner sidewall 165 of the proximal housing 6 of the trocar 2 so that fluid will run naturally down the fingers 160a, 160b. The wicking fingers 160a, 160b can also include a sorbent reservoir 164 disposed on a distal end thereof. In the illustrated embodiment, the sorbent reservoir 164 on each finger 160a, 160b is in the shape of ring seated within the proximal housing 6 and effective to sorb the fluids wicked away from the duckbill seal 163 by the wicking fingers 160a, 160b. The sorbent reservoir 164 can, however, have various other configurations such as ring segments. In use, as fluids are deposited on the duckbill seal 163 by instruments passing therethrough, the fluid will naturally flow to outer corners or edges of the seal face 161. The surface difference between the wicking fingers 160a, 160b and the duckbill seal 24 will cause fluid to flow from the seal 163 to the fingers 160a, 160b and down the fingers 160a, 160b into the sorbent reservoir 164. As will be appreciated by those skilled in the art, the wicking fingers 160a, 160b can be formed integrally with the duckbill seal 163 or can simply be in close contact with sealing face 161 of the duckbill seal 163.

Figure 9:
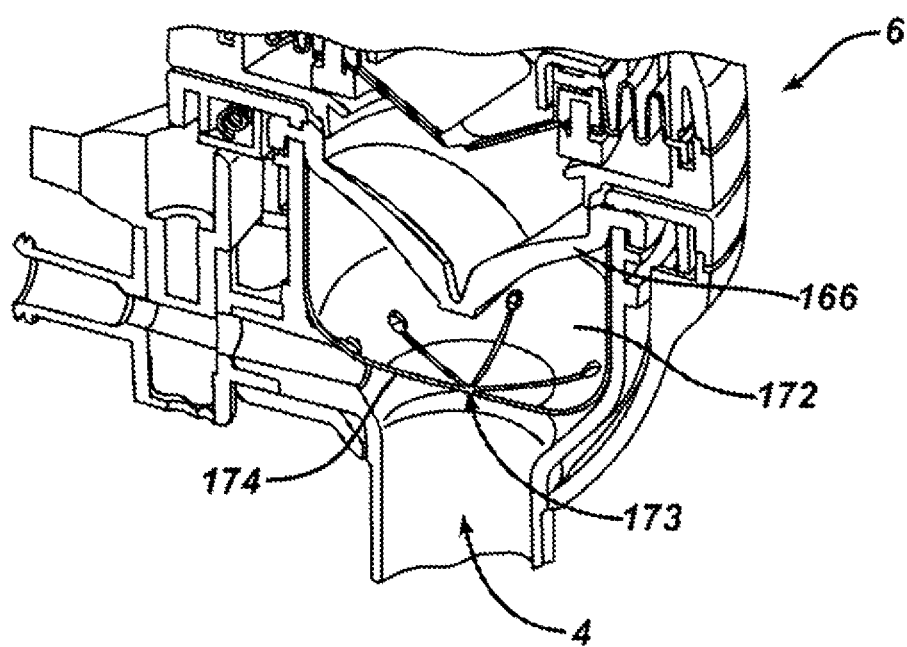
FIG. 9 is a cross-sectional view of one embodiment of a trocar housing having a sorbent element disposed therein.

FIG. 9 illustrates another embodiment of a fluid remover that is positioned distal of a zero-closure seal. Similar to the embodiment shown in FIG. 7, the fluid remover is in the form of a sorbent. However, in this embodiment the sorbent is a sorbent grommet 172. The grommet 172 can have a generally circular or conical configuration with an opening 173 formed therethrough, as shown, but it can have any number of other geometries to facilitate passage of an instrument therethrough. The grommet 172 can also include multiple slits 174 formed therein and extending radially outward from the opening 173 to reduce insertion and withdrawal forces on an instrument being passed therethrough. In use, the grommet 172 can be seated within a distal portion of the proximal housing 6 of the trocar, just distal of the duckbill seal 166, and the opening 173 can be positioned coaxial with the working channel 4. As a surgical instrument is passed therethrough, the grommet 172 will contact the instrument and sorb any fluid on the instrument. The grommet 172 can also sorb any fluid that drips off of the duckbill seal 166 as the seal 166 scrapes the instrument.

Figure 10A:
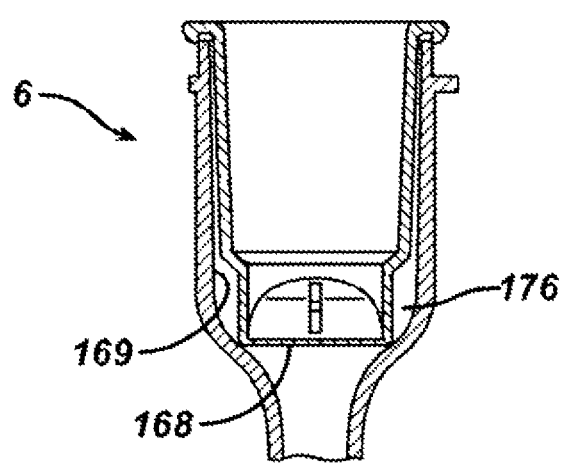
FIG. 10A is a cross-sectional view of one embodiment of a zero-closure seal having extension members for wicking fluid.
Figure 10B:
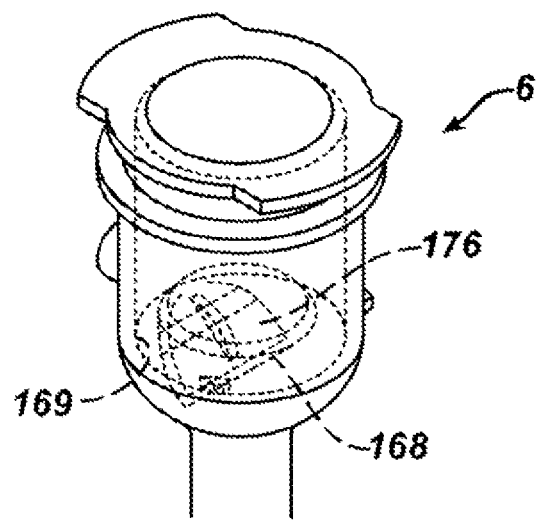
FIG. 10B is a transparent perspective view of the seal of FIG. 10A.
Figure 11:
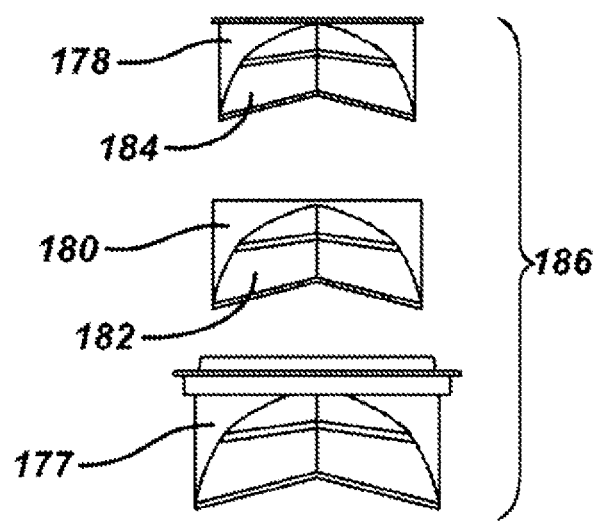
FIG. 11 is an exploded view of another embodiment of fluid remover assembly having a sorbent element nested between first and second zero-closure seals.

In other embodiments, the zero-closure seal itself can be modified to include a fluid remover. For example, FIGS. 10A and 10B illustrate another embodiment of a duckbill seal 176 in which the seal face 168 is extended distally and expanded in width to cause the outer ends of the seal face 168 to contact the inner sidewall 169 of the proximal housing 6 of the trocar, thereby forming a wicking element. In use, when an instrument is passed through the duckbill seal 176, the seal face 168 will scrape fluid off of the instrument. The fluid will naturally run outward toward the outer-most edges of the seal face 168. Since the outer edges are in contact with the inner sidewall 169 of the proximal housing 6, the fluid will be wicked away from the seal face 168 and onto the inner sidewall 169 of the housing 6. While not shown, the housing 6 can optionally include a sorbent disposed therein for sorbing the fluid wicked away from the seal.

FIG. 1I illustrates another embodiment of a modified zero-closure seal 186. In this embodiment, a sorbent element 180 is nested inside of the duckbill seal 177, and a second duckbill seal 178 is nested within the sorbent element 180. The nested sorbent 180 and the nested duckbill seal 178 can have two sealing walls, 182, 184 similar to the duckbill seal 177, that meet at a seal face that is configured to form a seal when no instrument is disposed therein and that are configured to open when a surgical instrument is passed therethrough. The body of the nested sorbent 180 and the nested duckbill 178 can each have a profile similar or identical to the duckbill seal 177, except smaller in size to all fit for a nested configuration. The components 177, 178, 180 can merely be seated within one another, or they can be attached to one another using various attachment mechanisms known in the art, including a press fit, glue, etc. In use, the seal face of all three components will contact a surgical instrument as it is passed through the seal assembly. The sorbent 180 will thus sorb any fluid on the instrument, as well as fluid scraped off of the instrument by the duckbill seal 177 and the nested duckbill seal 178.

Figure 12A:
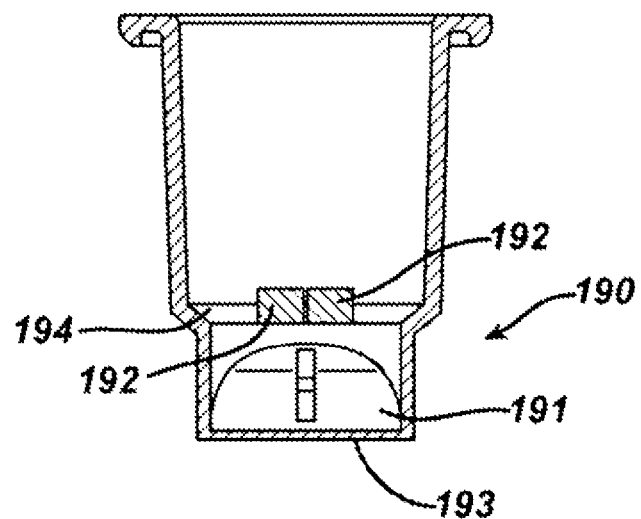
FIG. 12A is a cross-sectional view of yet another embodiment of a sorbent element having two sorbent bars disposed within a zero-closure seal.
Figure 12B:
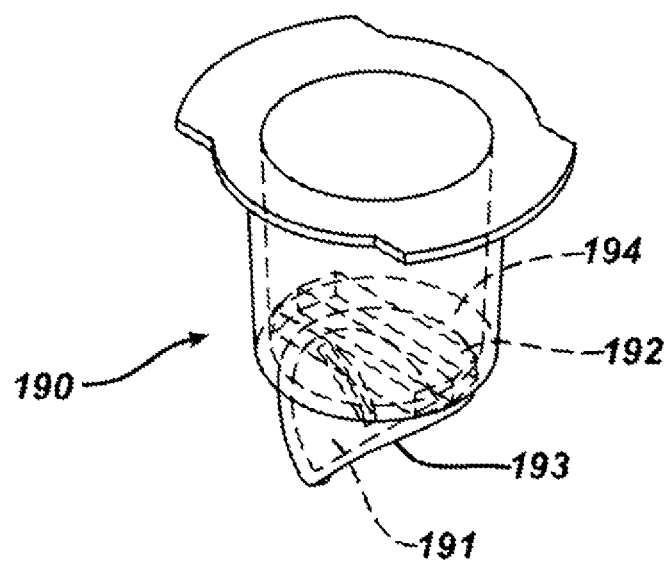
FIG. 12B is a transparent perspective view of the sorbent element and seal of FIG. 12A.

FIGS. 12A-12B illustrate another embodiment of a modified zero-closure seal 190. In this embodiment, the duckbill seal 191 includes two sorbent bars 192 disposed therein and extending thereacross. The sorbent bars 192 can be positioned to extend substantially parallel to the seal face 193, or to extend substantially perpendicular as shown. The seal 190 can also include a sorbent ring 194 positioned around an inner sidewall 193 of the duckbill seal 191 and in contact with the sorbent bars 192. The sorbent ring 194 can provide a reservoir for fluid collected by the sorbent bars 192. In use, the sorbent bars 192 will contact and engage a surgical instrument as it is passed through the duckbill seal 191, and will thus sorb fluid away from the surgical instrument.

As indicated above, the various fluid remover embodiments disclosed herein can be located anywhere within a trocar or other access device, including distal of a channel seal, between a channel seal and an instrument seal, or proximal of an instrument seal. The position of the fluid remover can also vary relative to an insufflation port, as will be discussed in more detail below. The fluid removers can also be formed integrally with the seal(s) and/or portions of the housing, and any combination of fluid removers can be used. FIGS. 13-22B illustrate various exemplary embodiments of fluid removers that are formed integrally or incorporated into an instrument seal, or located adjacent to an instrument seal and thus proximal to a channel seal.

Figure 13:
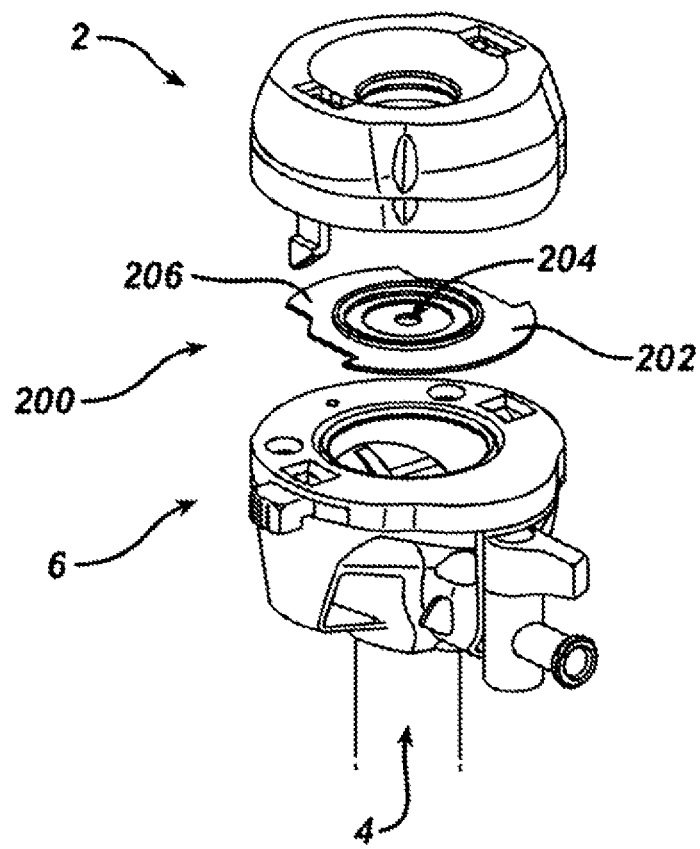
FIG. 13 is an exploded view of one embodiment of a trocar housing having a scraper for scraping fluid away from a surgical instrument passed therethrough.

Turning first to FIG. 13, in this embodiment the fluid remover 200 is in the form of a combination scraper and sorbent. In particular, the fluid remover 200 includes a generally planar circular scraper disc 202 having an opening 204 formed therethrough and configuration to be positioned coaxial with the working channel 4 in the trocar 2. The opening 204 can be sized and configured to form a seal around an instrument passed therethrough. The fluid remover 200 can also include a sorbent disk 206 disposed concentrically around the opening 204 in the scraper 202. In use, the scraper 202 will scrape fluid off of instruments passed therethrough, and the sorbent disk 206 will sorb the scraped fluid. The fluid remover 200 can be disposed within the proximal housing 6 of the trocar 2 using various techniques, but as shown in FIG. 13 the fluid remover 200 is configured to be engaged between the removable cap 5 and the distal portion of the proximal housing 6 of the trocar 2. As a result, the scraper 202 and sorbent 206 will be positioned in alignment with the working channel 4 extending through the housing 6, and will also be positioned between the proximal instrument seal and the distal channel seal.

Figure 14:
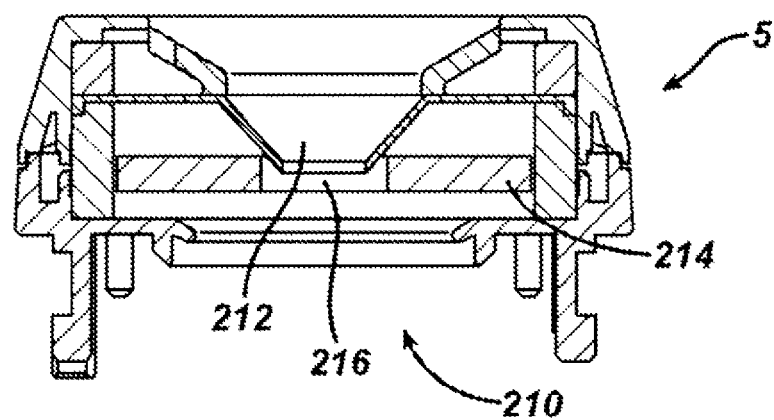
FIG. 14 is a cross-sectional view of one embodiment of a trocar cap having a scraper for scraping fluid away from a surgical instrument passed therethrough.

FIG. 14 illustrates another embodiment of a fluid remover 210 having a combination scraper and sorbent, however in this embodiment the fluid remover 210 is fully disposed within the removable cap 5 containing the instrument seal. As shown, a scraper 212 can be cone shaped and can be positioned just distal of the instrument seal. In other embodiments the scraper 212 can be planar. The scraper 212 can also replace or function as the instrument seal. A sorbent ring 214 can be positioned concentrically around and in contact with an opening 216 in the distal end of the of the conical scraper 212. As a result, the sorbent ring 214 will sorb any fluid scraped away from a surgical instrument extending through the scraper 212.

Figure 15A:
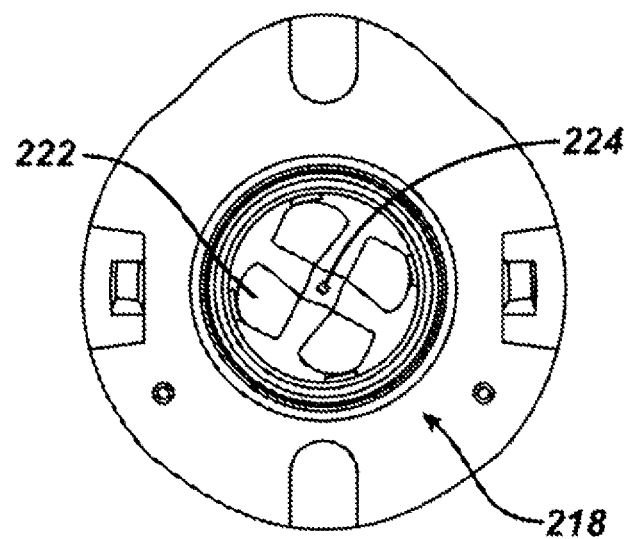
FIG. 15A is a top view of a trocar cap having another embodiment of a scraper for scraping fluid away from a surgical instrument passed therethrough.
Figure 15B:
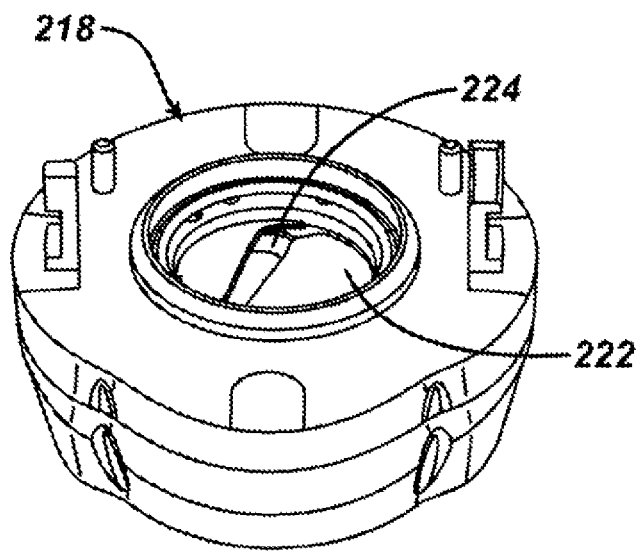
FIG. 15B is a side perspective view of the trocar cap of FIG. 15A.

In yet another embodiment, shown in FIGS. 15A and 15B, the fluid remover can be in the form of a scraper that is part of the instrument seal 218. As shown, the instrument seal 218 is a multi-layer seal having the protector disposed on a proximal surface thereof, as previously described with respect to FIG. 1E. The scraper can be in the form of a second protector 222 that is disposed distal to the multi-layer seal segments. The second protector 222 can have the same configuration as the protector of FIG. 1E, however the second protector 222 can define an opening 224 that is configured to contact and engage a surgical instrument passed through the seal 218. Accordingly, in use, the second protector 222 can engage and scrape fluid away from instruments passed through the seal 218.

Figure 16:
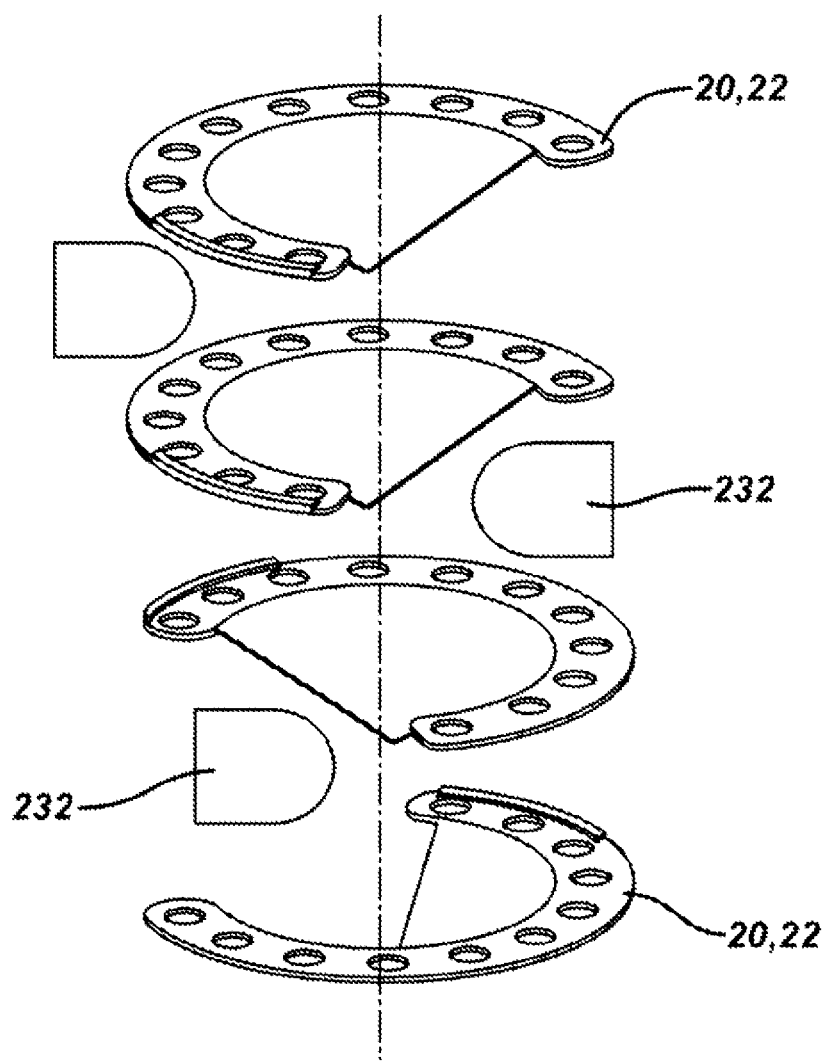
FIG. 16 is an exploded view of one embodiment of a multi-layer seal having a sorbent element disposed between the layers.

In another embodiment, shown in FIG. 16, the fluid remover can be in the form of a multi-layer sorbent that is positioned between the multiple layers 20 of the seal 16, as shown, or that is positioned between the multiple layers 22 of the seal protector 18. The sorbent can be in the form of multiple sorbent sheets 232 that are layered in between the layers of the seal 16 (or seal protector 18). Thus, in use, when an instrument is passed through the instrument seal, the sheets 232 will sorb any fluids scraped off of the instrument by the seal 14, thereby preventing fluid from accumulating around the opening of the seal 14 and being reapplied to a surgical instrument as it is reinserted therethrough. The sorbent sheets 232 can be effective to sorb fluid, as well as to interrupt surface tension and/or capillary action between the seal and the protector. Thus, there should be no fluid in or near the seal opening and/or protector opening that will be able to touch or collect on an instrument being passed therethrough.

Figure 17:
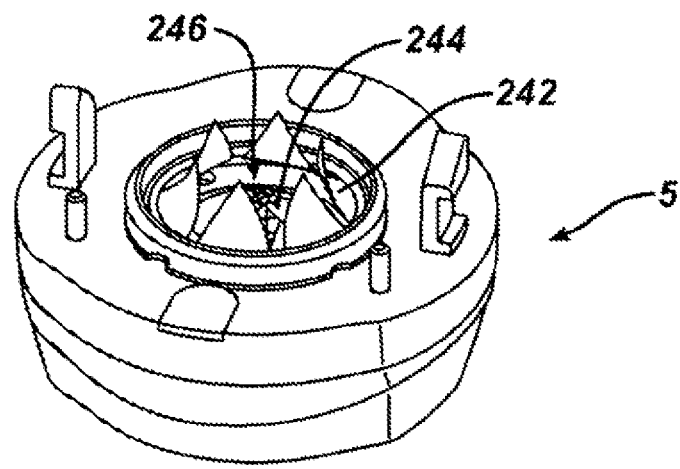
FIG. 17 is a bottom perspective view of one embodiment of a trocar cap having a sorbent element disposed therein.

FIG. 17 illustrates another embodiment of a sorbent fluid remover. In this embodiment, the sorbent is in the form of a grommet 242 having a configuration similar to the grommet 172 previously described with respect to FIG. 9. However, in this embodiment the grommet 242 is positioned adjacent to a distal surface 244 of the instrument seal 14, rather than the zero-closure seal 24. In particular, as shown in FIG. 17, the grommet 242 can be disposed concentrically around a distal opening 246 formed in the removable cap 5 such that instruments passed through the instrument seal 14 will contact the grommet 242, which will sorb fluids off of the instrument. The grommet 242 can also sorb any fluid that is scraped from or drips from the instrument seal 14.

Figure 18A:
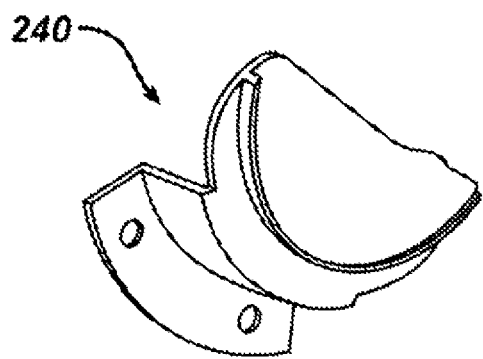
FIG. 18A is a bottom perspective view of one embodiment of a wicking element formed on a portion of a seal protector for creating between the seal protector and a seal.
Figure 18B:
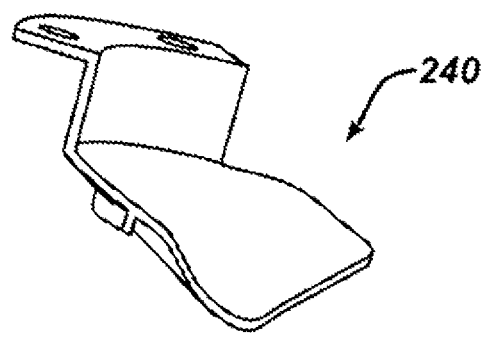
FIG. 18B is a top perspective view of the portion of the seal protector of FIG. 18A.

In another embodiment shown in FIGS. 18A and 18B, a wicking element is formed integrally with the multi-layer seal protector 18 previously described with respect to FIG. 1E. As previously explained, the multi-layer seal 16 can have a natural shape that is slightly conical and it can include an opening sized to receive an instrument therethrough. The protector 18 likewise has an opening, however in the embodiment shown in FIGS. 18A and 18B the length of a protector 240 is decreased to thereby increase the diameter of the opening defined by the protector 18. As a result, the protector 240 will have an opening that is larger than the opening in the seal 16 to create a flattened profile against the conical shape of the seal 16, thereby creating a gap between the protector 240 and seal 16. As surgical instruments are removed from the trocar, the gap will prevent fluids from collecting between the layers 20 of the seal 16 and will allow the protector 240 to wick fluids away from the opening of the seal 16. Thus, if fluid is deposited on the seal 16, there will be no capillary action to hold the fluid between the seal 16 and the protector 240, thereby allowing the fluids to drain. In addition, when an instrument is passed through the protector 240 and seal 16, the gap created between the seal 16 and protector 18 will prevent fluid from being squeezed from between the seal 16 and protector 240 and onto an instrument.

Figure 19A:
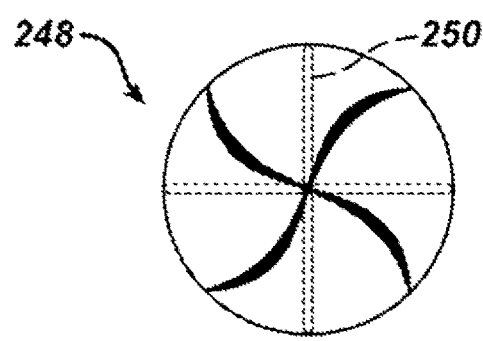
FIG. 19A is a top view of a multi-layer protective member having camming ribs.
Figure 19B:
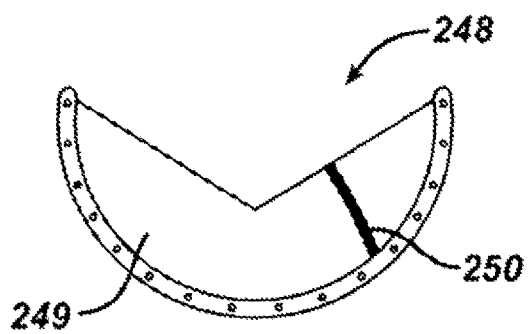
FIG. 19B is a top view of one layer of the protective member of FIG. 19A.

In another embodiment shown in FIGS. 19A and 19B, the multi-layer seal protector 248 has a wicking element in the form of camming ribs 250 disposed on a surface of each individual protector layer 249 so that the ribs 250 create pockets between the layers for wicking away and retaining fluid scraped off of instruments by the instrument seal. In the illustrated embodiment, the ribs 250 are offset by 90 degrees, although other geometries are possible as will be appreciated by those skilled in the art. In one embodiment, the ribs 250 can be disposed on a top or proximal surface of the protector. Thus, as a surgical instrument is passed through the instrument seal 14, the instrument will contact the ribs 250 to thereby cam open the protector 248 and the seal, preventing the surgical instrument from coming into contact with the surface of the protector 248 and/or the seal. In another embodiment, the ribs 250 can be disposed on a bottom or distal surface of the protector, thereby creating a gap between the protector 248 and the seal to prevent capillary action and the trapping of fluid between the seal and protector 248.

Figure 20A:
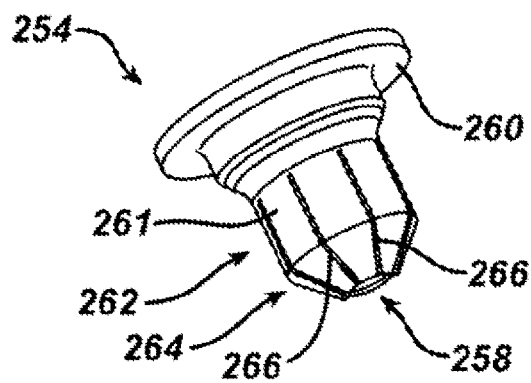
FIG. 20A is a side perspective view of a deep cone instrument seal having wicking ribs formed on an external surface.
Figure 20B:
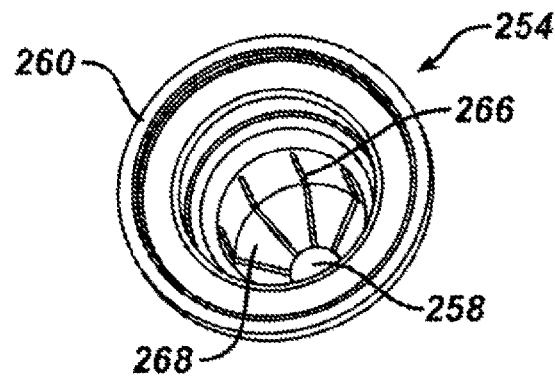
FIG. 20B is a top perspective view of another embodiment of a deep cone instrument seal having wicking ribs formed on an internal surface.

FIGS. 20A and 20B illustrate another embodiment of an instrument seal 254 having ribs for wicking fluid away from an opening in the seal 254. In this embodiment, the instrument seal 254 is in the form of a deep cone seal having a flange 260 with a conical sidewall 262 extending distally therefrom. A distal portion 264 of the conical sidewall 262 tapers inward to define an opening 258 in the distal end 264 of the seal 254. In the embodiment shown in FIG. 20A, the sidewall 262 can include one or more ribs 266 formed on an external surface 261 thereof and extending between proximal and distal ends of the sidewall 262, terminating at the opening 258. The external ribs 266 can be effective to wick fluid away from the opening 258 in the seal 254. In the embodiment shown in FIG. 20B, the ribs 266 are formed on the inner surface 268 of the sidewall 262 and extend between proximal and distal ends of the sidewall 262, terminating at the opening 258. The ribs 266 will thus have a camming effect, causing any instrument inserted through the seal 254 to contact the ribs 266 to cam open the seal 254, rather than contacting an inner surface 268 of the seal 254.

Figure 21:
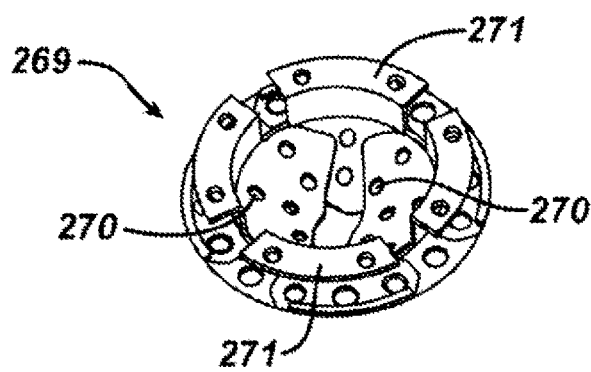
FIG. 21 is a perspective view of a multi-layer protective element having holes formed therein for receiving fluid.

In another embodiment, shown in FIG. 21, the multi-layer seal protector 269 can include a plurality of holes 270 formed in the individual layers 271 of the protector 269 to form a wicking element for wicking fluid away from the seal. As fluid is trapped between the protector 269 and the seal when an instrument is passed through the instrument seal, the holes 270 act to wick away fluid from the seal and from the opening in the seal. The fluid can be retained within the holes 270 by surface tension so that an instrument passed through the seal will not contact the fluid retained in the holes 270.

Figure 22A:
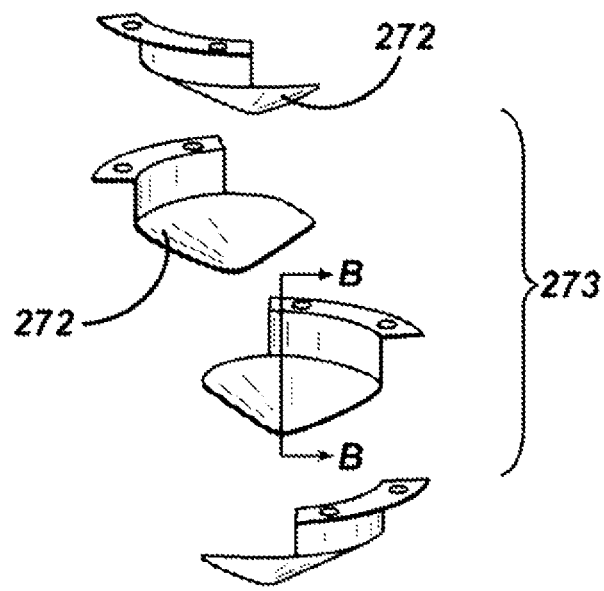
FIG. 22A is an exploded view of a multi-layer protective element.
Figure 22B:
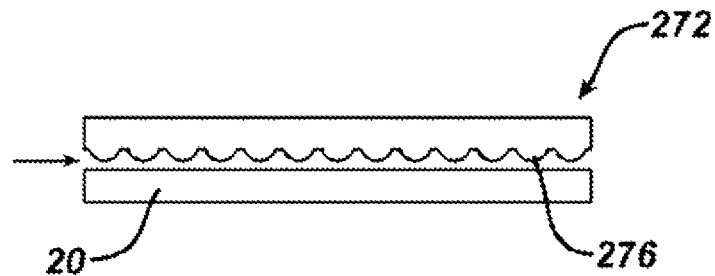
FIG. 22B is a cross-sectional view taken across line B-B of one of the protective elements of FIG. 22A.

Various other modifications can also be made to the multi-layer seal protector previously described in FIG. 1E to remove fluid from the seal or from instruments passed through the seal. In another embodiment, shown in FIGS. 22A and 22B, the protector segments 272 can include surface features, such as a roughened surface 276, formed on the distal surface thereof. As shown in FIG. 22B, when the protector segments 272 are positioned against the seal segments 20, the roughened surface 276 will create a gap that separates the protector 273 from the seal, thus providing a path for fluid to wick away from the opening in the seal and from between the protector 273 and the seal.

Figure 23A:
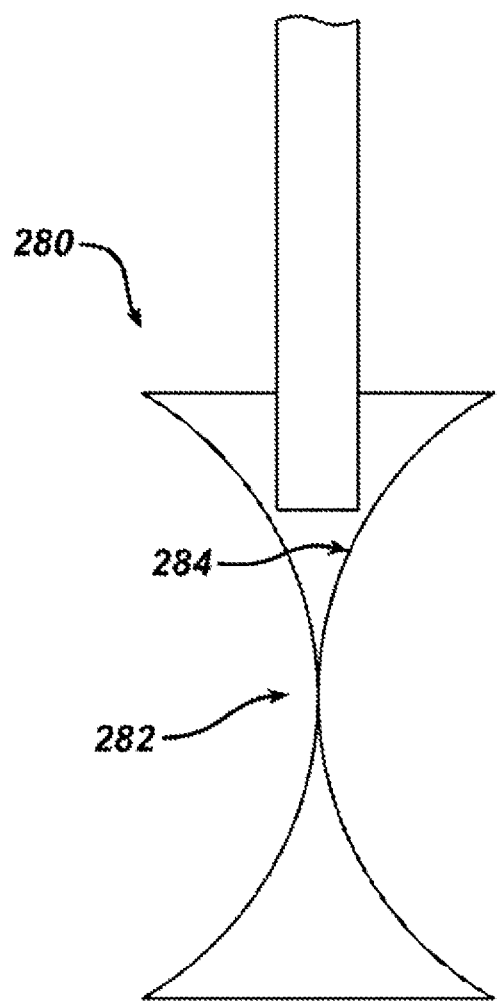
FIG. 23A is a side view of one embodiment of a seal having an hourglass configuration for scraping fluid off of a surgical instrument.
Figure 23B:
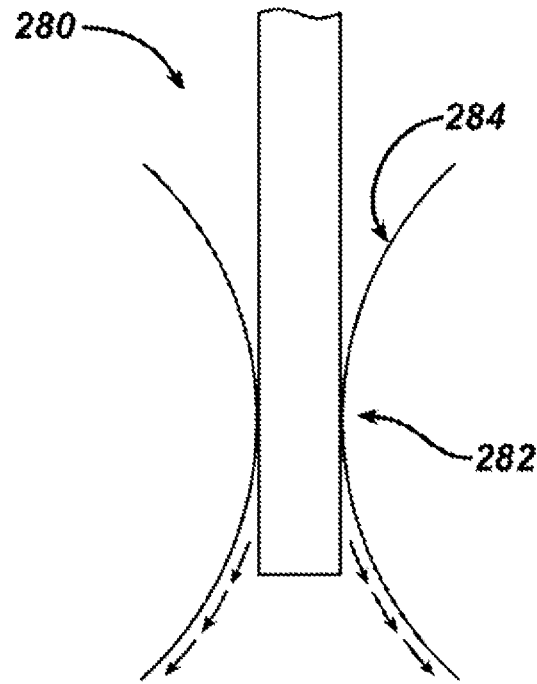
FIG. 23B is a side view of the seal of FIG. 23A showing an instrument passed therethrough.

FIGS. 23A-23B illustrate another embodiment of a seal 280 that is configured to remove fluid. In this embodiment, the seal 280 has an hourglass configuration such that the seal 280 is a combination trocar and instrument seal. In other words, the seal 280 is effective to both form a seal within the working channel of the trocar when no instrument is disposed therethrough and to form a seal around an instrument disposed therethrough. The hourglass shape of the seal 280 allows a central portion 282 of the seal 280, which in a natural state is in a closed configuration as shown in FIG. 23A, to open and engage an instrument passed therethrough, as shown in FIG. 23B, and thereby scrape any fluid off of the instrument. Due to the curvature in inner sidewalls 284 of the seal 280, the removed fluid will flow away from the central portion thus preventing the fluid from being redeposited onto an instrument reinserted therethrough. The hourglass configuration of the seal 280 is also advantageous in that it will accommodate instruments of various sizes. The central portion 282 can also move or float relative to the central axis of the working channel in the trocar, thus accommodating off-axis instruments.

FIGS. 24A-29 illustrate various other exemplary embodiments of fluid removers. While certain embodiments are described as being disposed or formed in the cannula, a person skilled in the art will appreciate that, as with previous embodiments, the embodiments of FIGS. 24A-29 can likewise be disposed at various locations within a trocar and that various combinations of fluid removers can be used.

Figure 24A:
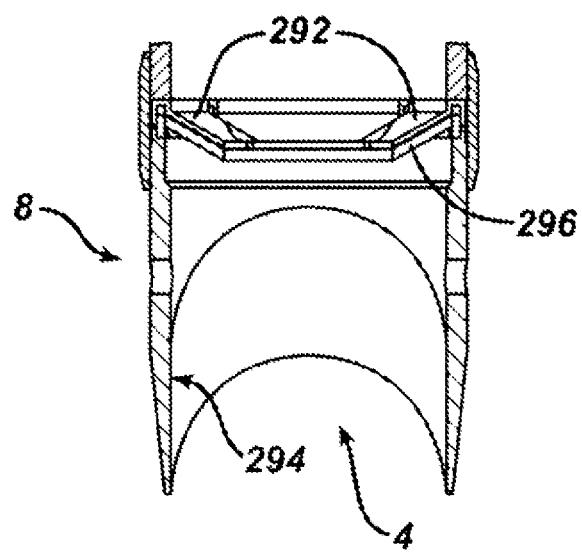
FIG. 24A is cross-sectional view of one embodiment of a trocar cannula having overlapping scrapers and a sorbent disposed therein.
Figure 24B:
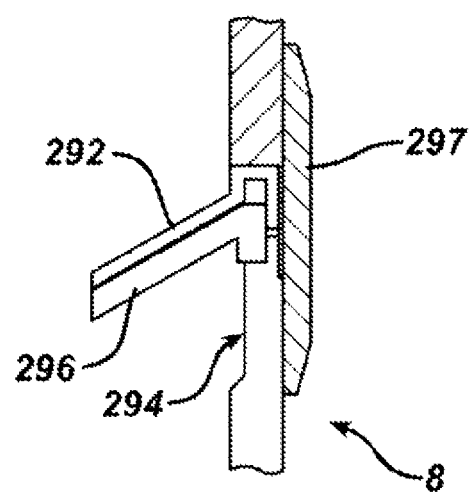
FIG. 24B is an enlarged view of one of the scrapers and sorbents of FIG. 24A.

In the embodiment shown in FIGS. 24A and 24B, the fluid remover is in the form of a plurality of scraper elements that extend at least partially across the working channel 4 of the cannula 8. The scraper elements can be relatively thin and can take the shape and form of wipers 292, as best shown in FIG. 24B, that will scrape or squeegee fluid off of a surgical instrument passed through the cannula 8. The wipers 292 can be fixedly or hingedly coupled to an inner sidewall 294 of the cannula 8, and they can be flexible to accommodate instruments of various sizes, and to allow both insertion and withdrawal of the instruments. The cannula 8 can also include any number of wipers 292, and the wipers 292 can be spaced apart from one another, or they can be in a stacked configuration. The wipers 292 can have a conical configuration such that each wiper 292 extends around the entire inner diameter of the cannula 8. Alternatively, the wipers 292 can be formed into individual segments that are positioned a distance apart from one another, e.g., approximately 90 degrees apart within the interior surface 294 of the cannula 8. The segments can be layered within the cannula 8 so that different parts of the surgical instrument come into contact with the wipers 292 at different heights as the instrument is being passed therethrough. The wipers 292 can also be in contact with a sorbent element 296, or include a sorbent portion, such that the collected fluid drips onto or is wicked into the sorbent material and away from possible contact with a reinserted instrument. As shown in FIGS. 24A-24B, the sorbent element 296 is located adjacent to the inner sidewall 294, and thus radially outward from the wiper body 292. The sorbent elements 296 can be formed into a wall of the cannula 8, so that the cannula 8 is partially formed from the sorbent elements 296. The sorbent elements 296 can also be formed within grooves in the cannula wall and/or can be adhered directly to the cannula wall by any attachment mechanism known in the art, for example an attachment ring 297. In use, as an instrument is passed through the cannula 8, the instrument will be scraped on all sides simultaneously by the plurality of wipers 292. The fluid will flow outward where it will be sorbed by the sorbent element 296.

Figure 25:
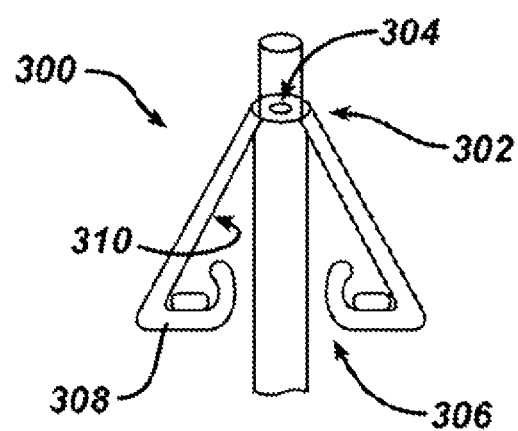
FIG. 25 is a perspective view of another embodiment of a scraper for scraping fluid off of a surgical instrument shown passed therethrough.

FIG. 25 illustrates another exemplary embodiment of a scraper 300. In this embodiment, the scraper 300 is substantially cone shaped increasing in diameter in a distal direction. A proximal end 302 of the scraper 300 includes an opening 304 formed therethrough, and a fluid collection member is formed at a distal end 306 thereof and extends inwardly. The fluid collection member can have a variety of configurations and can be generally configured to collect fluid scraped by the scraper 300. In one exemplary embodiment, as shown, the fluid collection member can be in the form of a substantially C-shaped lip 308 extending inwardly from the distal end 306 of the scraper 300. At least a portion of the fluid collection member can also optionally be sorbent thereby enabling the fluid collection member to both collect and sorb fluid scraped by the scraper. The scraper 300 can be formed from a pliable material such that it can radially expand to engage a surgical instrument extending therethrough. In use, the narrow proximal end of the scraper 300 can engage a surgical instrument passed therethrough to thereby scrape fluid away from the instrument. The fluid scraped away from the instrument will run down an inner surface 310 of the scraper 300 and be collected and/or sorbed by the fluid collection member disposed at the distal end 306 of the scraper 300. While the scraper 300 is generally indicated as being disposed in the cannula 8, the scraper 300 can likewise be disposed anywhere within the trocar 2, including in the proximal housing 6.

Figure 26:
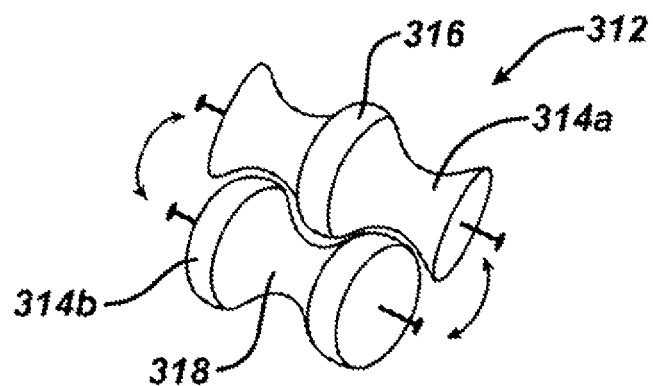
FIG. 26 is a perspective view of another embodiment of a device for scraping fluid away from a surgical instrument.

FIG. 26 illustrates another exemplary embodiment of a scraper 312. In this embodiment, the scraper 312 includes first and second rotatable members 314a, 314b that are configured to rotate and engage a surgical instrument as the instrument is passed therethrough. The first and second rotatable members 314a, 314b can have a variety of shapes and sizes. In the illustrated embodiment, the first and second rotatable members 314a, 314b are spool shaped. The spools can be configured such that the geometry of second member 314b complements that of the first member 314a. As shown, the first member 314a includes a substantially spherically shaped central portion 316 that corresponds with a concave cut-out 318 in the second member 314b. The geometry of the spools can have several shapes including, but not limited to, straight sided cylindrical, c-shaped, and indented cylindrical. The first and second rotatable members 314a, 314b can be positioned at a variety of locations in the cannula, or within the proximal housing of a trocar, and they can be formed from a variety of materials including, but not limited to, rigid, pliable, and sorbent materials. In use, the rotatable members 314a, 314b can rotate and engage a surgical instrument passed therethrough to thereby scrape and optionally sorb fluid away from the instrument.

Figure 27A:
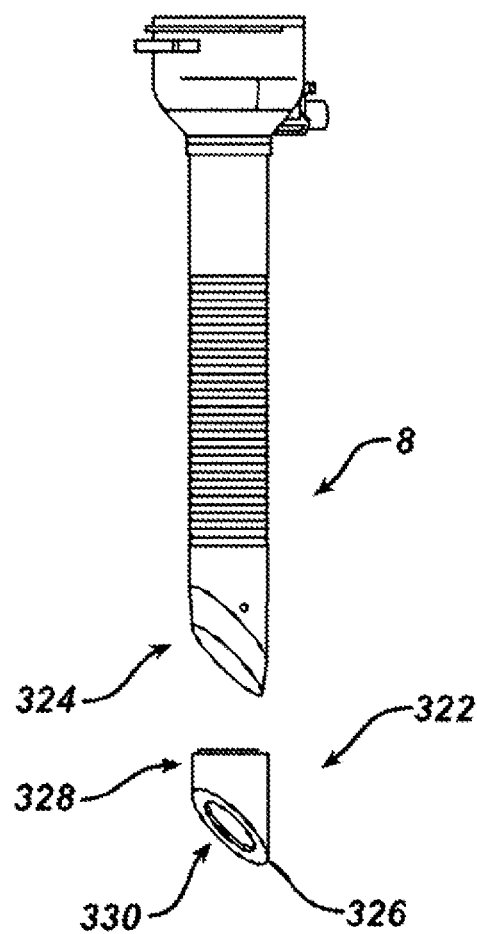
FIG. 27A is an exploded view of a trocar and removable tip for scraping fluid away from a surgical instrument.
Figure 27B:
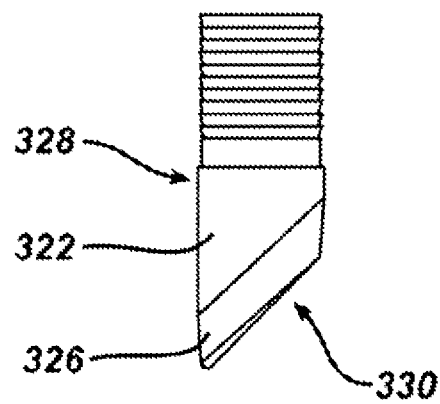
FIG. 27B is an assembled side view of a distal end of the trocar and removable tip of FIG. 27A.
Figure 27C:
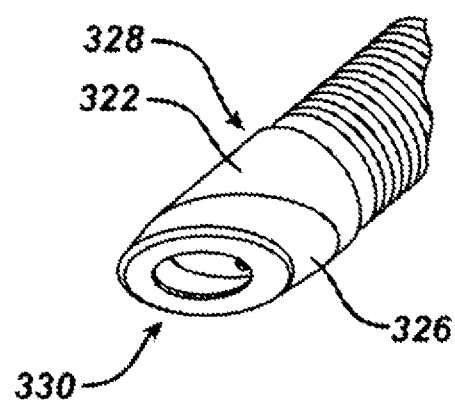
FIG. 27C is a perspective view of the removable tip and distal end of the trocar of FIG. 26B.

FIGS. 27A-27C illustrate another embodiment of a fluid remover in the form of a removable tip or sleeve 322 that can be removable coupled to a distal end 324 of the cannula 8. As shown, the sleeve 322 is in the form of a generally cylindrical housing with a tapered distal end 326, similar to the distal end 324 of the cannula 8. A proximal end 328 of the sleeve 322 can be sized to fit over and engage the distal end of the cannula 8, e.g., by interference fit, and the distal end of the housing can include an opening 330 formed therein and sized to receive a surgical instrument therethrough. The sleeve 322, or at least a portion of the sleeve 322 surrounding the opening 330 at the distal end 326, can be formed from a compliant or expandable material to allow the opening in the sleeve 322 to radially expand as an instrument is passed therethrough. Exemplary compliant materials include, but are not limited to, polyisoprene, pellathane, and silicone. In use, as a surgical instrument is passed through the opening 330 in the sleeve 322, the opening 330 will scrape fluid off of the instrument, thereby preventing the fluid from being dragged into the trocar and deposited on the seals.

Figure 28:
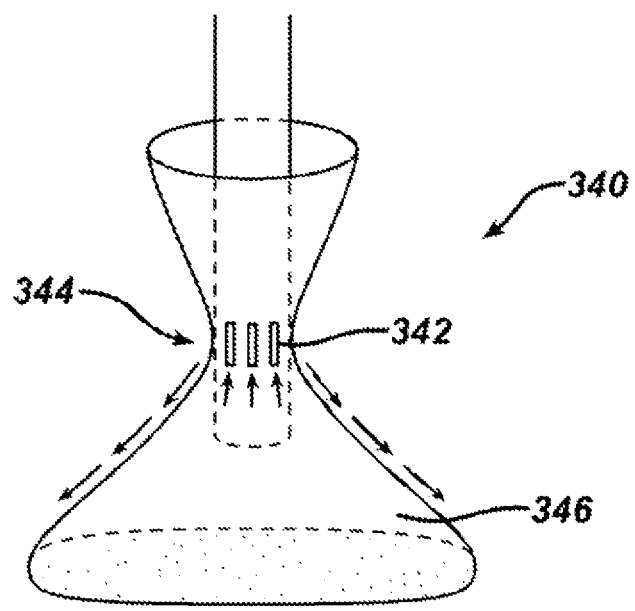
FIG. 28 is a partially-transparent side view of one embodiment of wicking element having an hourglass shape.

In another embodiment shown in FIG. 28, an hourglass shaped seal 340, similar to the seal 280 described with respect to FIGS. 23A-23B is provided, however the seal 340 includes a wicking element in the form of one or more cut-outs or slots 342 formed in the central, reduced-diameter portion 344. Similar to the seal 280 previously described with respect to FIGS. 23A and 23B, the hourglass shape will allow the central portion 344 to scrape or squeegee fluid from a surgical instrument passed therethrough. The cut-outs or slots 342 will allow the scraped fluid to be wicked through the slots 342 to an exterior surface 346 of the seal 340.

Figure 29:
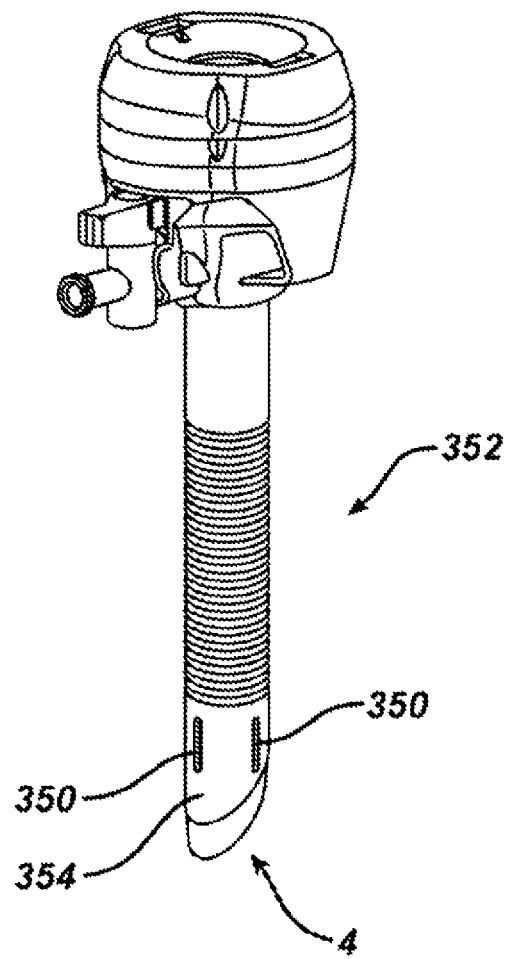
FIG. 29 is a perspective view of a trocar having a cannula with slots formed therein for wicking fluid out of the cannula.

In another embodiment shown in FIG. 29, the wicking element can take the form of a plurality of slots 350 formed in the working channel 4 of a cannula 352. The slots 350 can have any size and shape sufficient to transfer fluid disposed on an inner surface of the cannula 352 to an outside surface 354 of the cannula 352. Thus, as an instrument is passed through the cannula 352, any fluid that drips down the inner surface of the cannula 352 will be transferred to the external surface 354 of the cannula 352 through the slots 350.

Figure 30B:
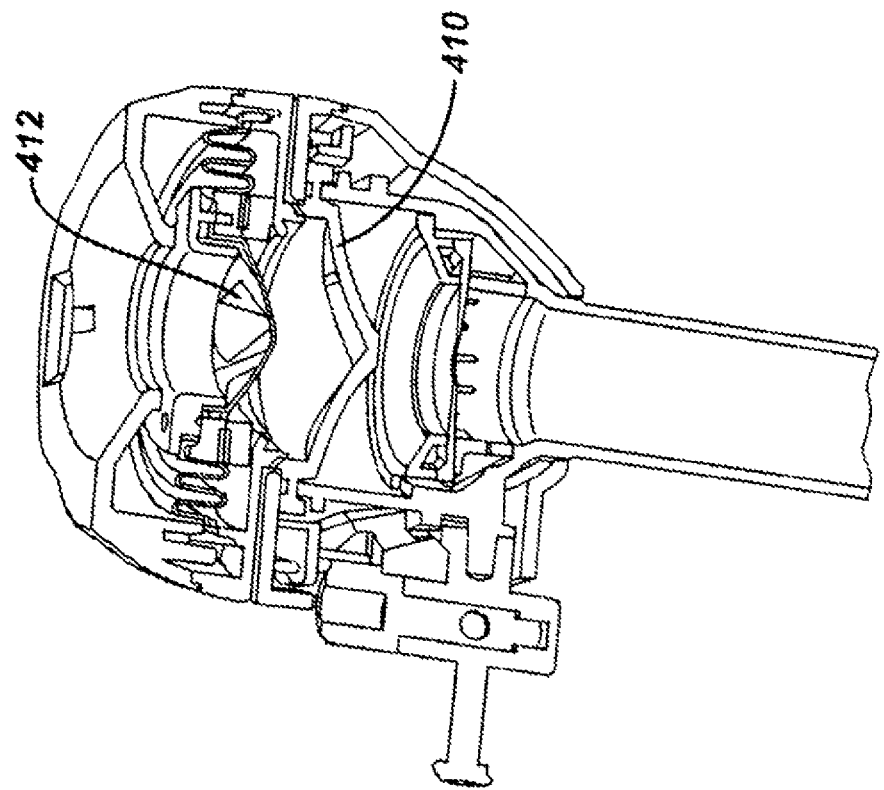
FIG. 30B is a cross-sectional side view of the trocar of FIG. 30A.
Figure 30A:
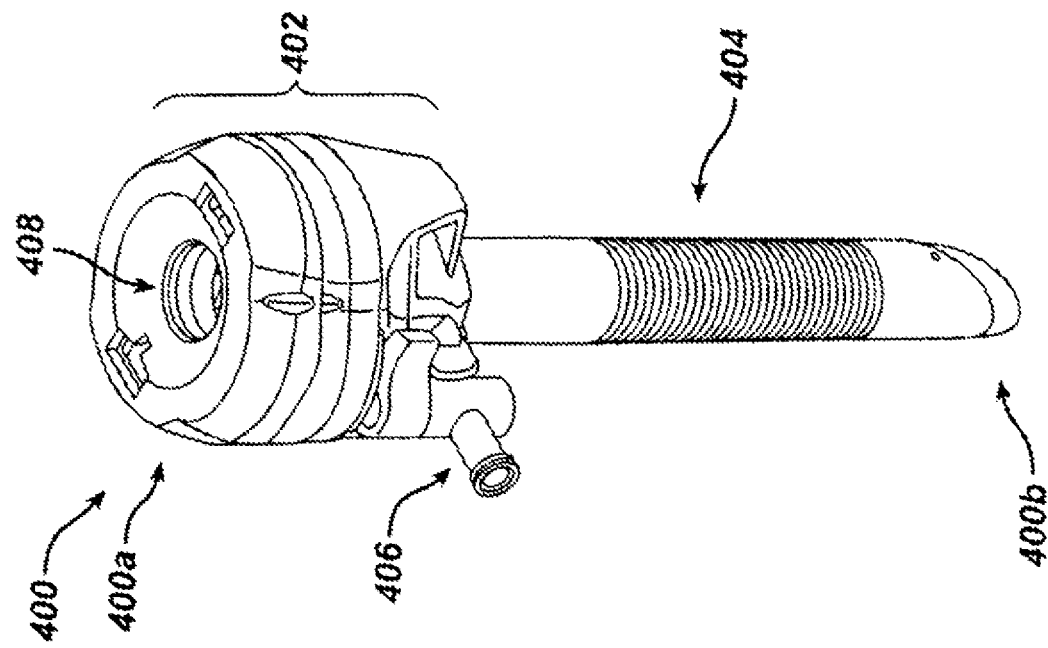
FIG. 30A is a perspective view of another embodiment of a trocar having a proximal housing and a distal cannula.
Figure 30C:
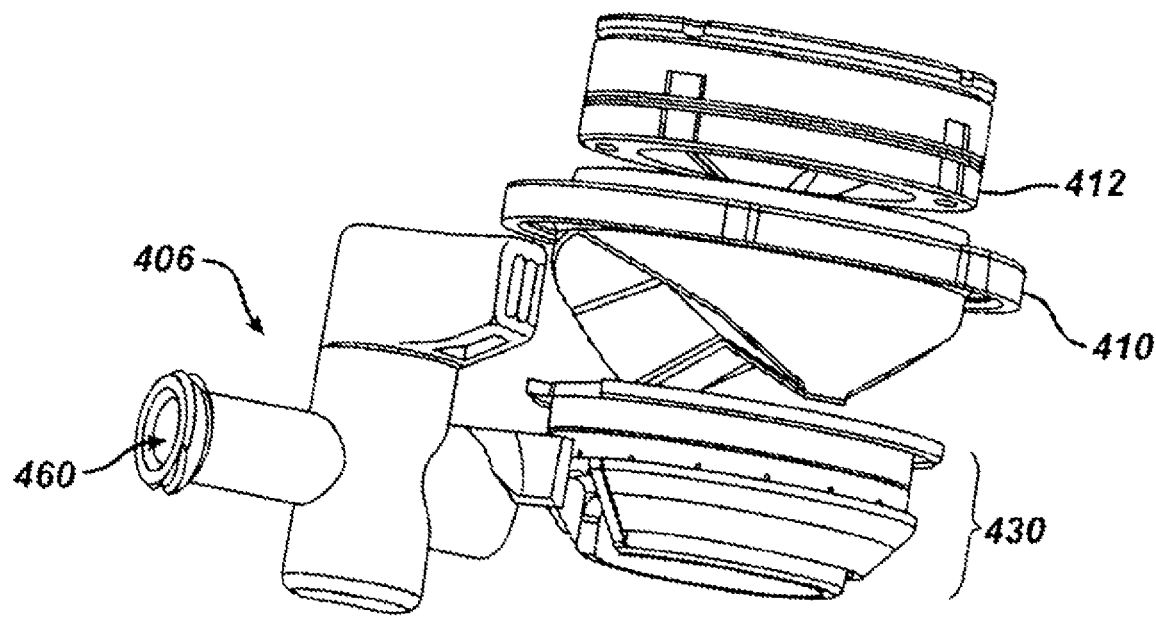
FIG. 30C is a perspective view of an instrument seal assembly, a channel seal, a fluid remover assembly, and an insufflation port of the trocar of FIG. 30A.
Figure 30D:
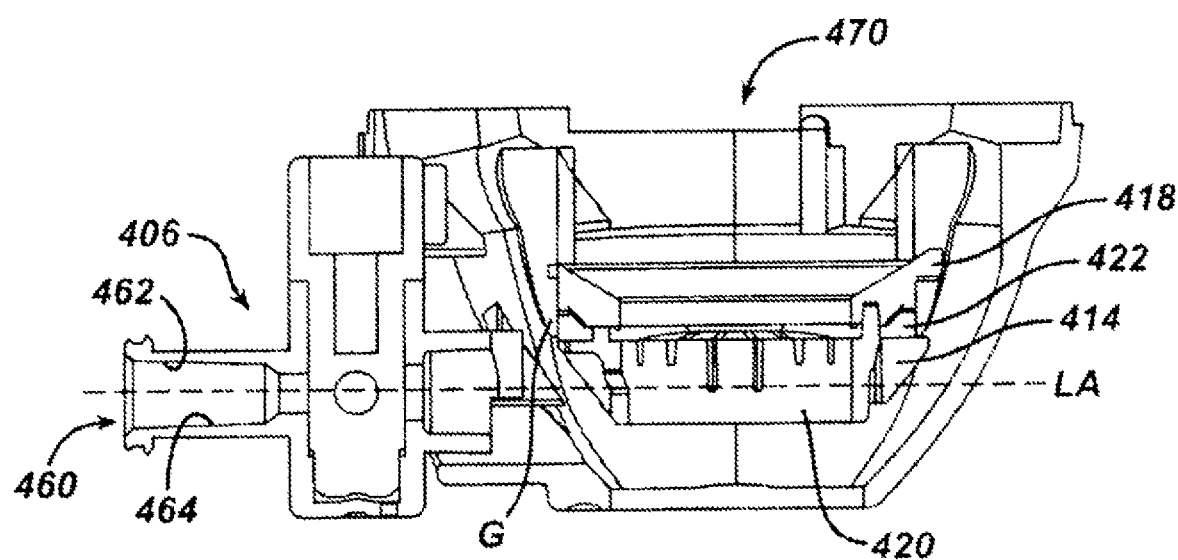
FIG. 30D is a cross-sectional side view of the fluid remover and insufflation port of FIG. 30C.
Figure 30E:
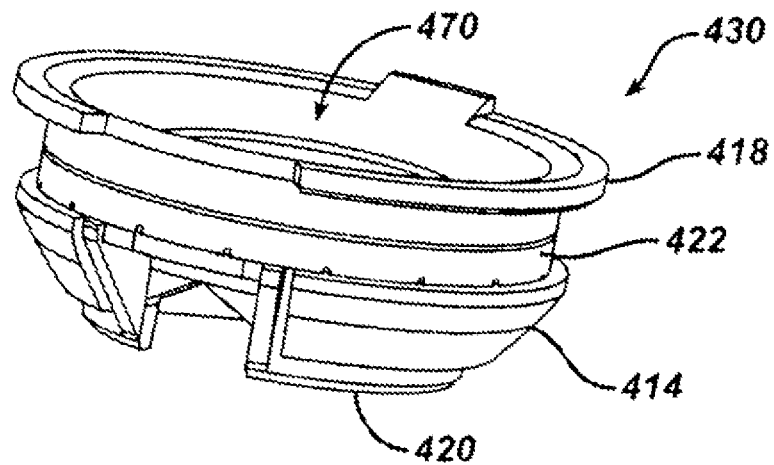
FIG. 30E is a perspective view of a fluid remover of FIG. 30C.
Figure 30F:
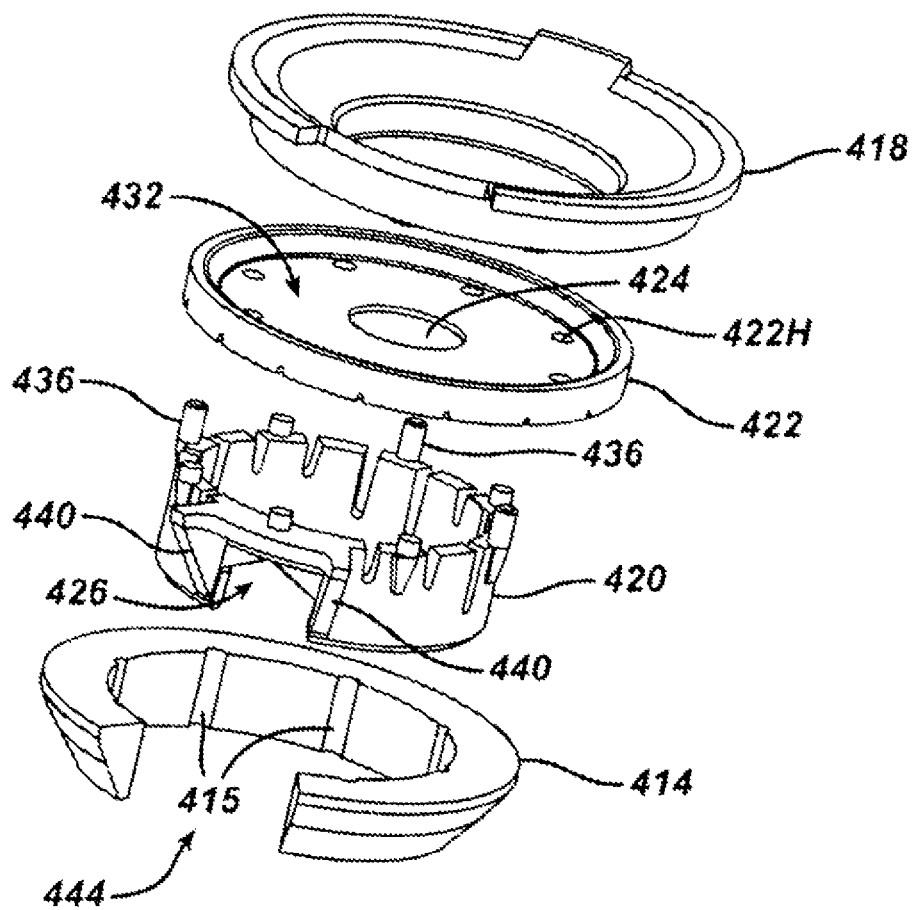
FIG. 30F is an exploded view of the fluid remover of FIG. 30E showing a lid, scraper, crown, and sorbent.

FIGS. 30A-30J illustrate another embodiment of a trocar 400 having a fluid remover 430 disposed therein. As shown, the trocar 400 has a proximal housing 402 and a distal cannula 404 with a working channel 408 formed through and extending between proximal and distal ends 400a, 400b thereof. The housing 402 can include one or more seals that are effective to seal the working channel 408, i.e., to prevent the escape of insufflation, when no instrument is disposed therethrough and/or when an instrument is disposed therethrough. As shown in FIGS. 30B and 30C, the housing 402 includes a proximal instrument seal, in the form of a multi-layer seal 412, that is effective to form a seal around an instrument inserted therethrough, and a distal channel seal, such as a duckbill seal 410, that is effective to seal the working channel when no instrument is inserted therethrough. One exemplary embodiment of a duckbill seal 410 that can be used with the present invention is disclosed in U.S. patent application Ser. No. 11/771,263 filed on Jun. 29, 2007 and entitled "Duckbill Seal With Fluid Drainage Feature," by Paul T. Franer and Thomas A. Gilker. Such a duckbill is particularly useful as it has a low profile and has fluid drainage features that can assist in further preventing fluid from being redeposited onto instruments inserted through the seals. A person skilled in the art will appreciate that any number, type, and configuration of channel and/or instrument seals can be positioned within the housing 402 at various locations. The housing can also include an insufflation port 406 is formed in the housing 402 for providing an insufflation gas to the working channel 408. Additionally, in some implementations, the distal cannula 404 can include an angled distal surface arranged at distal end 400b. The angled distal surface can have a distal-most point and a proximal-most point, and the distal-most point can be aligned with the insufflation port 406, as depicted in FIG. 30A.

As indicated above, the housing 402 can include a fluid remover 430 positioned therein and configured to remove fluid from a surgical instrument inserted therethrough. The fluid remover 430 can have an opening 470 formed through a center portion thereof, in axial alignment with the working channel 408, for receiving a surgical instrument. The opening 470 can be effective to remove fluid from a surgical instrument upon insertion and/or withdrawal therethrough. In an exemplary embodiment, the fluid remover 430 is preferably positioned distal to the seals 412, 410 so that fluid collected on the instrument when disposed in a body cavity can be removed from the surgical instrument before it is withdrawn through the seals 412, 410, thus preventing the fluid from being deposited on the seals and thereafter deposited onto an instrument inserted into the trocar. In order to position the fluid remover 430 distal to the seals 412, 410, the fluid remover 430 will positioned proximal to, distal to, or in the path of the insufflation port. Where the fluid remover 430 is positioned in the path of or distal to the insufflation port, it is preferably configured so that it does not block the path of an insufflation gas from the port through the distal cannula 404. During many surgical procedures using a trocar, insufflation is used to expand the body cavity into which the trocar extends. Trocars can thus have an insufflation port, such as the port 406 shown in FIGS. 30A-30C, that is positioned distal to the seals 412, 410 so that the seals are effective to prevent gas from flowing out of the proximal housing 402. In this way, a constant flow of gas is maintained through the distal cannula 404 and into the body cavity. Since the port 406 is positioned distal to the seals 412, 410, in an exemplary embodiment, in order to maintain a low profile housing and position the fluid remover 430 distal of the seals, the fluid remover 430 can be positioned adjacent to or distal to the port 406. As such, the fluid remover 430 is preferably configured to allow air to pass therethrough and/or therearound such that it does not block the flow of insufflation gas from the port 406 to the cannula 404 when an instrument is inserted through the opening 470 in the fluid remover 430. In other words, the fluid remover 430 can have a configuration that allows the passage of insufflation gas from the port 406 to the distal cannula 404 even when an instrument is disposed through the fluid remover 430. FIGS. 30A-30J illustrate one such embodiment of the fluid remover 430 that is in the pathway of the flow of gas from the port 406 to the cannula 404. In this embodiment, a cut-out or pathway is provided in a portion of the fluid remover 430 to allow the passage of gas therethrough from the port 406 to the cannula 404, as will be discussed in more detail below. The fluid remover 430 can also include other features to facilitate the passage of gas therethrough, as will be discussed in more detail below.

The fluid remover 430 can have various configurations and it can include any one or more of a wicking element, a sorbent, and a scraper. FIGS. 30C-30F illustrate one embodiment of the fluid remover 430 that is positioned distal to the seals 412, 410 and in proximity to the insufflation port 406. The fluid remover 430 generally includes a sorbent 414 disposed within the housing and disposed around a crown 420, a scraper 422 positioned on a proximal surface of the crown 420, and a lid 418 positioned against a proximal surface of the scraper 422.

Figure 30G:
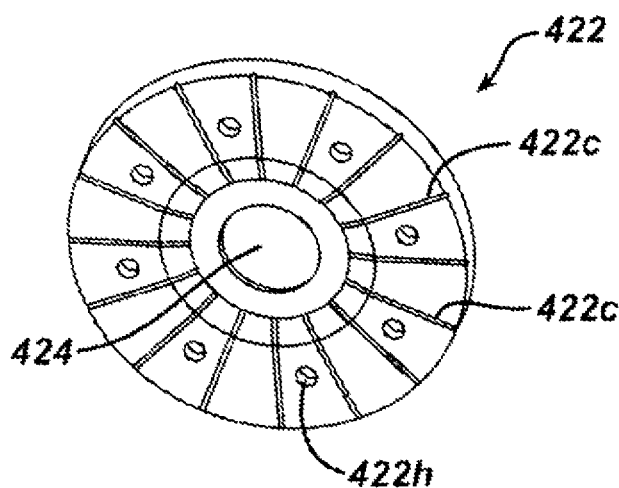
FIG. 30G is a bottom perspective view of a scraper of FIG. 30F showing channels formed therein.

As shown in more detail in FIGS. 30F and 30G, the scraper 422 of the fluid remover 430 can have many shapes and configurations, but in the illustrated embodiment the scraper 422 is disc shaped and has an opening 424 formed through a center portion thereof. The scraper 422 can be configured to remove fluid from a surgical instrument passing through the opening 424 by contacting the surgical instrument and scraping and/or squeegeeing its circumference. In an exemplary embodiment, the scraper 422 is formed from a flexible and resilient material to allow the opening 424 of the scraper 422 to expand around and engage an outer wall of an instrument passed therethrough.

The scraper 422 can also include features to direct fluid flow. For example, as shown in FIG. 30G, the scraper can include one or more channels 422c formed in a distal surface thereof and extending radially outward from the opening 424 such that fluid scraped off of an instrument being withdrawn through the opening 424 will flow through the channels and radially away from the opening 424. As further shown in FIGS. 30F and 30G, the scraper 422 can also include one or more holes 422h formed therethrough for receiving pins formed on the crown 420, as will be discussed in more detail below. The holes 422h allow the scraper 422 to rest on a proximal surface of the crown 420 and to be captured between the crown 420 and the lid 418. The holes 422h can also have a size that allows air to pass therethrough when the pins of the crown 420 are disposed therein. Such a configuration can assist in preventing the fluid remover 430 from functioning as a seal, as will be discussed in more detail below. In some embodiments, however, the scraper 422 can also be formed as an instrument seal and/or as a scraper for smaller diameter surgical instruments and a seal for larger diameter surgical instruments.

In certain exemplary embodiments, in order for the scraper 422 to effectively wick fluid radially outward from the opening and toward the sorbent, all or portions of the scraper can be formed from or can include a hydrophilic material. For example, the scraper can be formed from a hydrophilic material, such as a nylon, and/or the scraper can be spray coated, dip-coated, plasma etched, or otherwise coated using various known coating techniques, with a surfactant coating that renders the scraper or portions thereof hydrophilic. In an exemplary embodiment, where the scraper is formed from a hydrophobic material, such as a polyisoprene, a hydrophilic coating is applied to the scraper to render the scraper hydrophilic. The coating can be applied to any one or more of the surfaces of the scraper, and it can be applied at any stage during manufacturing. In one embodiment, the scraper can be soaked in a surfactant bath during manufacturing to render the entire scraper hydrophilic. Exemplary coating materials include, by way of non-limiting example, Dodecylbenzene sodium sulfonate (SDBS), and Sodium Dodecyl Sulfate (SDS). The coating is preferably one that remains stable during sterilization, such as gamma and thermal sterilization.

Figure 30H:
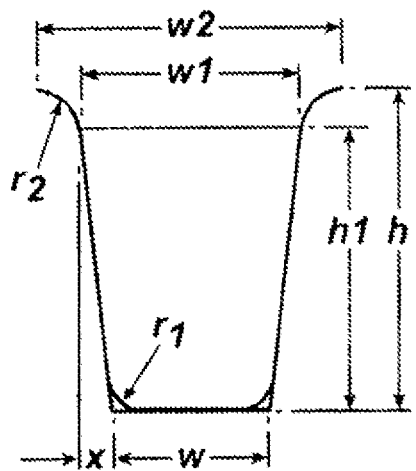
FIG. 30H is a cross-sectional view of one of the channels of the scraper of FIG. 30G.

A person skilled in the art will appreciate that various factors can be altered to facilitate the wicking action of the scraper. For example, the contact angle of a drop of fluid on a hydrophilic surface of the scraper can be optimized so that fluid will spread upon contact with the surface. In certain exemplary embodiments, the hydrophilic material can have a low contact angle, such as 90 degrees or less. Other factors that can affect the ability of the scraper to wick fluid away from the opening include the smoothness of the surface, the geometry of the wicking channels, and the surface tension of the fluid being applied. For example, the channel geometry can be designed so as to provide the capillary forces necessary to drive fluid to a minimum capillary height so that the fluid will extend just past the outer wall of the crown 420 to reach the sorbent 414. The channel geometry can be altered to achieve the desired capillary height. FIG. 30H illustrates one exemplary embodiment of a channel geometry that is optimized to facilitate the capillary action of the channel. As shown, the channel has a generally U-shaped cross-sectional shape, with the inner corners, located at the base of the channel, being rounded and having a radius of curvature $r_1$, and the outer corners, located at the opening of the channel, being rounded and have a radius of curvature $r_2$. The channel can also have a width w at the base, as measured between the opposed sidewalls of the channel, that differs from a width w1 at the opening, as measured between the outer rounded corners, and that also differs from a maximum width $w_2$ as measured from the outer-most ends of the channel at the opening. The difference between width w and width $w_1$ is indicated by reference x. The channel can further have a maximum height h, as measured from the base to the outer-most ends of the channel at the opening, that differs from a height $h_1$, as measured from the base to the outer rounded corners. The particular dimensions of the channel can vary. For example, the radius of curvature $r_1$ at the base of the channel can be less than the radius of curvature $r_2$ at the opening of the channel, and the width w at the base of the channel is less than the width w1 at the opening, which in turn is less than the maximum width $w_2$ such that the width of the channel gradually increases from the base to the opening. In an exemplary embodiment, however, the width w at the base of the channel is preferably equal to or greater than the width w1 at the opening. The dimensions and cross-sectional shape of the channel can also vary along the entire length of the channel. For example, the channel can have a height and/or width that increases or decreases radially outward, such that the height and/or width of the channel near the central opening in the scraper is either less than or greater than the height and width of the channel near the outer perimeter of the scraper. Each channel can also reach a maximum height and/or width at a certain distance from the central opening, and the height and/or width can then remain constant along the remainder of the channel extending radially outward from that location. A person skilled in the art will appreciate that the channel can be modified to obtain a desired capillary height so as to cause fluid to be driven from the scraper opening, past the crown, and to the sorbent.

As indicated above, other modifications can be made to achieve an optimum wicking effect. In another embodiment, the scraper and sorbent can both be configured to have a surface energy gradient, such that the surface energy increases as fluid travels from the opening in the scraper, along the channels, and into the sorbent.

The fluid remover 430 can also include a scraper crown 420, shown most clearly in FIG. 30F, that can extend distally from a distal surface of the scraper 422 and that can assist in mounting the scraper 422 and sorbent 414 within the housing. The scraper crown 420 can have various configurations, but in the illustrated embodiment it has a ring shaped body 434 with multiple pins 436 extending proximally therefrom. The pins 436 can extend through the corresponding holes 422*h* formed in the scraper 422 and into holes 418*h* formed in the lid 418, as shown in FIG. 30J. The crown 420 and lid 418 can be mated to one another using various techniques, such as a pressed fit or interference fit, adhesive or welding, etc. By engaging the scraper 422 between the lid 418 and the crown 420, the scraper 422 can have an outer diameter that is less than an inner diameter of the housing 402 such that a gap G is provided between the scraper 422 and the housing 402, as shown in FIG. 30D. The gap G will allow air to flow proximally past the scraper 422.

As further shown in FIG. 30F, the scraper crown 420 can also include a cut-out 426 formed in a sidewall thereof. One or more flange members 440 can extend radially outward from a sidewall of the scraper crown 420 on each side of the cut-out 426 formed through the crown 420 to define a pathway. The flange members 440 can be positioned to axially align with the a cut-out formed in the sorbent 414 and a cut-out formed in the lid 418, as will be discussed in more detail below, to form a complete pathway that allows the flow of insufflation gas from the insufflation port 406, through the cut-outs, and to the working channel 408 into the distal cannula 404. This allows insufflation to be delivered through the cannula while an instrument is passed through the fluid remover 430 and occludes the working channel. The flange portions 440 can be positioned on either side of an opening of the insufflation port 406, through which the insufflation gas flows. As a result, a pressure on each side of the fluid remover will be equalized.

Figure 30I:
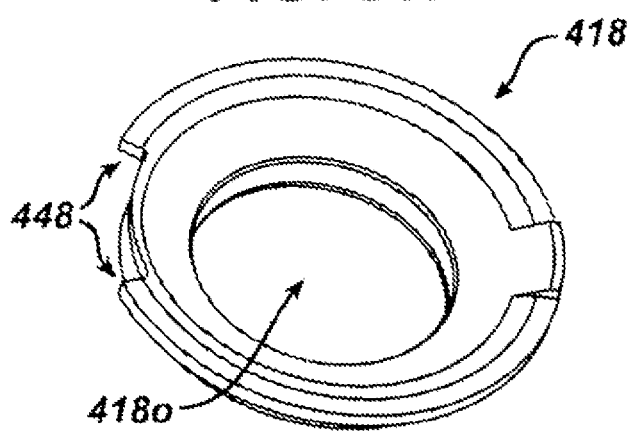
FIG. 30I is a top view of a lid of FIG. 30F.
Figure 30J:
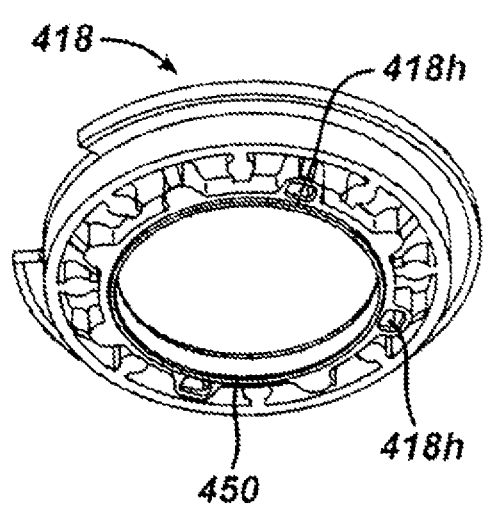
FIG. 30J is a bottom view of the lid of FIG. 33I.

The shaped scraper lid 418 is shown in more detail in FIGS. 30I and 30J, and it can have a generally circular or ring-shaped configuration that rests proximal to the scraper. In use, the lid 418 can serve to protect the proximal surface 432 of the scraper 422 from the insertion of sharp surgical instruments by acting as a guide or funnel for the surgical instrument into the opening 424 of the scraper 422. As indicated above, the scraper lid 418 can include one or more holes 418*h* formed in a distal surface thereof for receiving the pins 436 formed on the crown 420. The scraper lid 418 can also include an opening 418*o* through which a surgical instrument can extend that is in axial alignment with the opening 424 formed in the scraper 422, and a cut-out 448 formed in a sidewall or perimeter of the scraper lid 418 that aligns with the cut-out 446 formed in the scraper crown 420 and the sorbent 414.

As shown in FIG. 30J, in one embodiment the scraper lid 418 can further include a circular bead or compression ridge 450 protruding distally beyond a distal-most surface thereof such that the ridge extends toward and presses against the proximal surface of the scraper 422 to hold the scraper 422 in controlled compression between the compression ridge 450 on the lid 20 and the proximal surface of the crown 420. The compression ridge 450 can also function to seal off and prevent fluid from flowing back toward the opening of the scraper 422.

While there can be many configurations for the fluid remover 430, in the embodiment shown in FIGS. 30B-30E, the fluid remover 430 also includes a sorbent 414 positioned circumferentially around the scraper crown 420 and configured to sorb fluid scraped by the scraper 422. As shown in FIG. 30F, the sorbent 414 can be configured to be positioned around the scraper crown 420, and thus can have a cut-out 444 formed therein that aligns with the cut-out 426 formed in the crown 420. The terminal ends of the sorbent 414 will thus abut the flange 440 on the crown 420. As a result, the sorbent 414 will be substantially C-shape. The cut-out 444 in the sorbent 414 will also allow air to flow all the way around the outside of the scraper 422, due to the gap G between the outer perimeter of the scraper 422 and the housing. The cut-out in the sorbent 414 will thus continue to allow air to pass by and around the scraper 422 in the event the sorbent 414 becomes clogged. This is particularly advantageous, as air forced to flow through the sorbent 414 could potentially push fluid out of the sorbent 414. The sorbent 414 can be secured around the scraper crown 420 using any method known in the art including, for example, an adhesive or simply by an interference fit between an interior wall of the housing 402 and the scraper crown 420. As will be appreciated by those skilled in the art, the sorbent 414 can have a solid ring shape, or any other shape, and it can be composed of multiple individual portions as needed.

While the sorbent 414 preferably has a shape that corresponds to the shape of the crown 420, the sorbent 414 can be configured to be compressed between the crown 420, the scraper 422, and the housing 402. Thus, the sorbent 414 can have an initial cross-sectional shape that is more square and it can deform into a shape that is more triangular. The sorbent 414 can be formed from various materials that allow it to be compressed, while still allowing the sorbent 414 to sorb fluid. The sorbent 414 can also be permeable such that air can flow therethrough.

The particular size of the sorbent 414 can also vary, but in an exemplary embodiment the sorbent 414 has an inner diameter that is greater than a diameter of the opening 424 in the scraper, such that the sorbent 414 will only contact the scraper 422 at a location radially outward of the opening 424. This will allow fluid to flow from the opening, through the channels 422c, and then sorbed by the sorbent. In an exemplary embodiment, the sorbent is positioned radially outward of the holes 422h formed in the scraper, as this allows the sorbent 414 to be positioned around the crown 420.

As indicated above, when the fluid remover 430 is fully assembled, it can rest within a distal portion of the proximal housing 402. The sorbent 414 can be positioned in contact with an inner surface of the housing 402, the crown 420 can be disposed within the sorbent 414, the scraper 422 can rest on the crown 420 and be positioned in contact with the sorbent, and the lid can be positioned on the scraper 422 and be mated to the crown 420. The lid 418 can optionally be sonic welded or otherwise fixedly mated to the housing 402 to secure the fluid remover 430 therein. As shown in FIG. 30F, the sorbent 414 can include surface features, such as longitudinally extending grooves 415 formed on an inner surface thereof and configured to align with and receive the pins 436 on the scraper crown 420.

When disposed within the housing 402, the fluid remover 430 will be positioned in the path of insufflation. In particular, referring again to FIGS. 30C and 30D, the insufflation port 406 has a lumen 460 extending therethrough. The lumen 460 defines a longitudinal axis LA and has a cylindrical interior surface with a proximal-most interior surface 462 and a distal-most interior surface 464. The fluid remover 430 is generally positioned in the pathway of the lumen 460 and more particularly, it is positioned such that the proximal-most interior surface 462 of the lumen 460 is positioned distal to the scraper 422 and the longitudinal axis LA extends through a mid-portion of the sorbent 414. In other words, the sorbent 414 is positioned in the path of the flow of gas from the insufflation port 406 to the distal cannula. A person skilled in the art will appreciate that the various components of the fluid remover 430 can be positioned at various locations relative to the insufflation port 406. Since portions of the fluid remover 430 in the illustrated embodiment are positioned in the pathway of air flow from the insufflation port 406 to the distal cannula, the cut-outs 426 and 444 in the crown 420 and sorbent 414 will allow airflow to pass therethrough and into the distal cannula.

In use, a surgical instrument can be inserted through the seals 412, 410 and through the opening 470 in the fluid remover 430 as needed in a particular procedure. Using the insufflation port 406, insufflation gas can be introduced into the working channel 408 of the trocar 400 such that insufflation is achieved distal to the seals 412, 410 and to the fluid remover 430. The insufflation gas can travel along the pathway defined by the flange portions 440, through the cut-outs 426, 444 in the crown 420 and sorbent 414, respectively, and into the working channel 408 of the distal cannula 404. In this way, the fluid remover 430 can be distal to the seals 412, 410 to remove fluid from instruments being withdrawn while allowing the flow of insufflation gas into the distal cannula. As a surgical instrument is withdrawn from the working channel 408, fluid scraped from the surgical instrument by the scraper 422 flows radially outward and is sorbed by the sorbent 414, thus keeping the fluid away from any instrument that may be reinserted into the working channel 408. The fluid remover 430 thus allows for the removal of fluid from a surgical instrument at a position distal to the seals 412, 410 while also allowing the introduction of insufflation gas distal to both the seals 412, 410. A person skilled in the art will appreciate the variations possible for the positioning of seals and fluid removers to allow insufflation distal to both.

Figure 31:
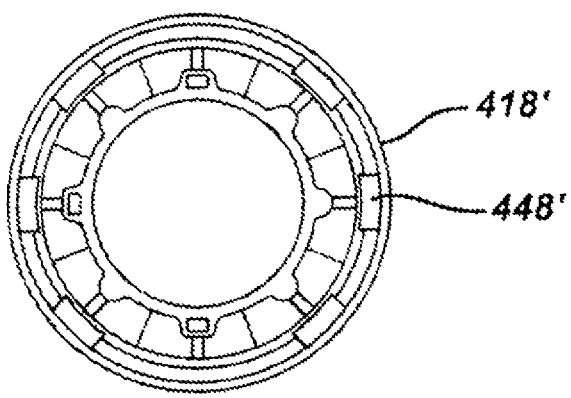
FIG. 31 is a bottom view of another embodiment of a lid for use with a fluid remover assembly.

FIG. 31 illustrates another embodiment of a lid 418' for use with a fluid remover. In this embodiment, rather than including a cut-out 448 formed in a sidewall of the lid 418 for allowing air to pass by the lid 418 in a proximal direction toward the seals, the lid 418' includes a plurality of holes or openings 448' formed therein and positioned radially around a perimeter of the lid 418'. The lid 418' can include any number of holes at any location and having any size. The holes 448' are merely configured to prevent the fluid remover from forming a seal, if not needed, as it may be desirable to maintain a zero pressure differential across the fluid remover in order to prevent air from forcing fluid out of the sorbent.

Figure 32A:
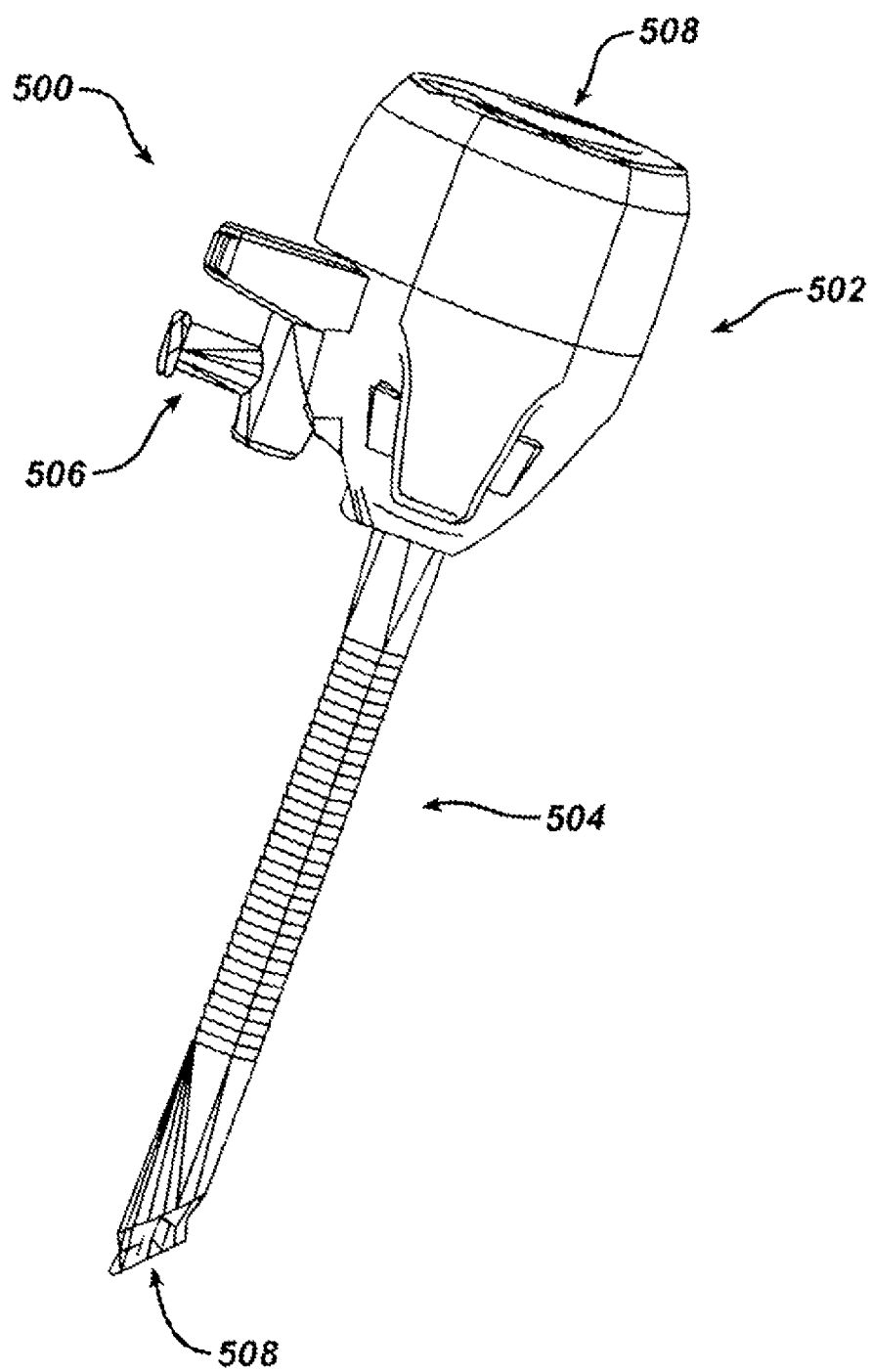
FIG. 32A is a perspective view of another embodiment of a trocar.
Figure 32B:
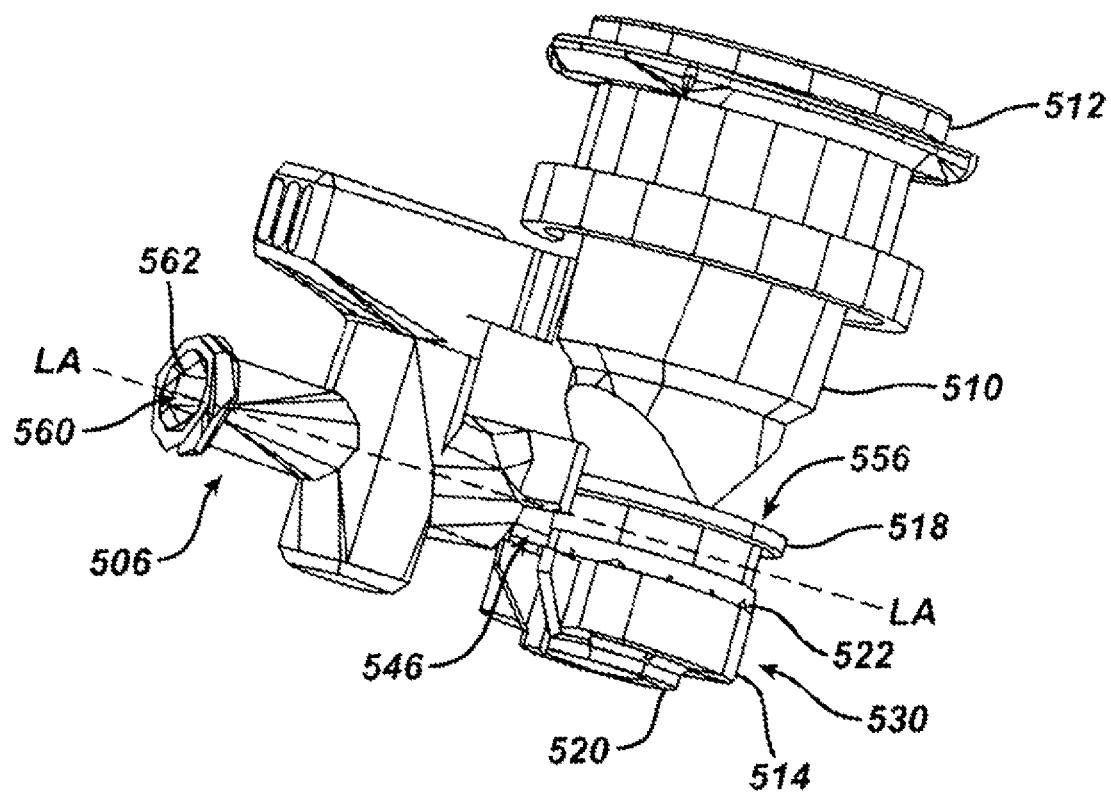
FIG. 32B is a side perspective view of an instrument seal, a channel seal, a fluid remover, and an insufflation port of the trocar of FIG. 32A.
Figure 32C:
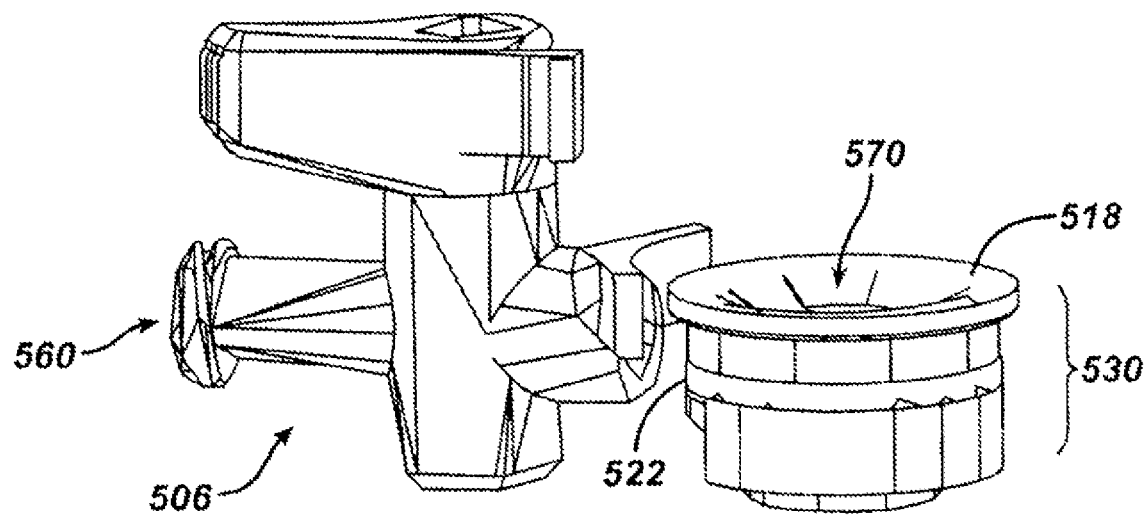
FIG. 32C is a side view of the fluid remover and insufflation port of FIG. 32B.

FIGS. 32A-32D illustrate yet another embodiment of a trocar 500 having a fluid remover 530 disposed therein. As shown, the trocar 500 has a proximal housing 502 and a distal cannula 504 with a working channel 508 formed through and extending between proximal and distal ends thereof. As shown in FIG. 32B, the housing 502 can include an instrument seal, such as a deep cone seal 512 (only a proximal rim is shown), positioned within a channel seal, such as a duckbill seal 510. A person skilled in the art will appreciate that any number, type, and configuration of channel and/or instrument seals can be positioned within the housing 502. The housing can also include an insufflation port 506 is formed in the housing 502 for providing an insufflation gas to the working channel 508.

In this embodiment, the fluid remover 530 differs from fluid remover 430 described above in that it is positioned more distal relative to the insufflation port. In general, the fluid remover 530 has an opening 570 formed through a center portion thereof, in axial alignment with the working channel 508, for receiving a surgical instrument. The opening 570 can be effective to remove fluid from a surgical instrument upon insertion and/or withdrawal therethrough. The fluid remover 530 is positioned distal to the seals 512, 510 so that fluid can be removed from the surgical instrument before it is withdrawn through the seals 512, 510 in order to prevent the deposit of fluid on the seals. As with fluid remover 430, fluid remover 530 can have a configuration that allows the passage of insufflation gas from the port 506 to the distal cannula 504 even when an instrument is disposed through the fluid remover 530. In particular, in this embodiment the fluid remover 530 is generally positioned in the pathway of the lumen 560 of the insufflation port 506 and more particularly, it is positioned such that the longitudinal axis LA of the lumen 560 extends through a substantially center portion of the scraper lid 518. The proximal-most interior surface 562 of the port is thus generally aligned with a top wall 556 of the scraper lid 518. As shown in FIG. 32B, the scraper 522 is thus positioned distal to the longitudinal axis LA of the lumen 560 and can generally be positioned in alignment with the distal-most interior surface 564 of the lumen 560. In other embodiments, the scraper 522 can be positioned entirely distal or proximal to the distal-most interior surface 564 of the lumen 460. A person skilled in the art will appreciate that the fluid remover 530 can be positioned in any number of ways relative to the lumen 560.

Figure 32D:
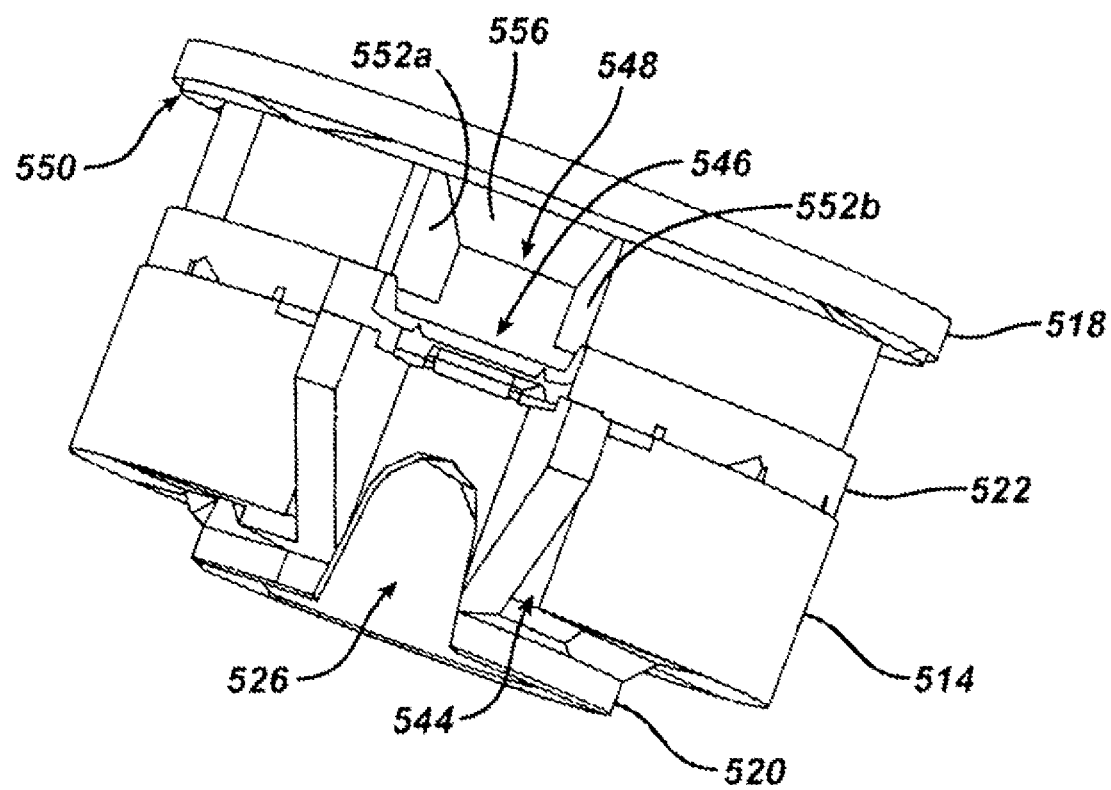
FIG. 32D is a side perspective view of the fluid remover of FIG. 32C.

Since portion of the lid 518 and the scraper 522 are positioned in the path of insufflation, the lid 518 and scraper 522 in this embodiment can each have a cut-out 548, 546 that is positioned within the pathway of the insufflation gas to allow the gas to flow into the working channel 508, as shown in FIG. 32D. The cut-outs 548, 546 can align with the corresponding cut-outs 526, 544 in the crown 520 and the sorbent 514, respectively, similar to the crown 420 and sorbent 414 discussed above. As further shown in FIG. 32D, the scraper lid 518 can also include a rim or flange 550 extending around a proximal portion thereof and located proximal to the cut-out 548 formed in the sidewall of the scraper lid 518. As a result, the notch 546 is not a complete cut-out, but is defined on three sides by two opposed notch side walls 552a, 552b, and a top wall 556 and thus the top wall 556 can optionally serve as a proximal, sealed boundary for the insufflation gas pathway that will be described below. In an exemplary embodiment, the top wall 556 can be positioned in alignment with the proximal-most interior surface 562 of the lumen 560 in the insufflation port.

Figure 33A:
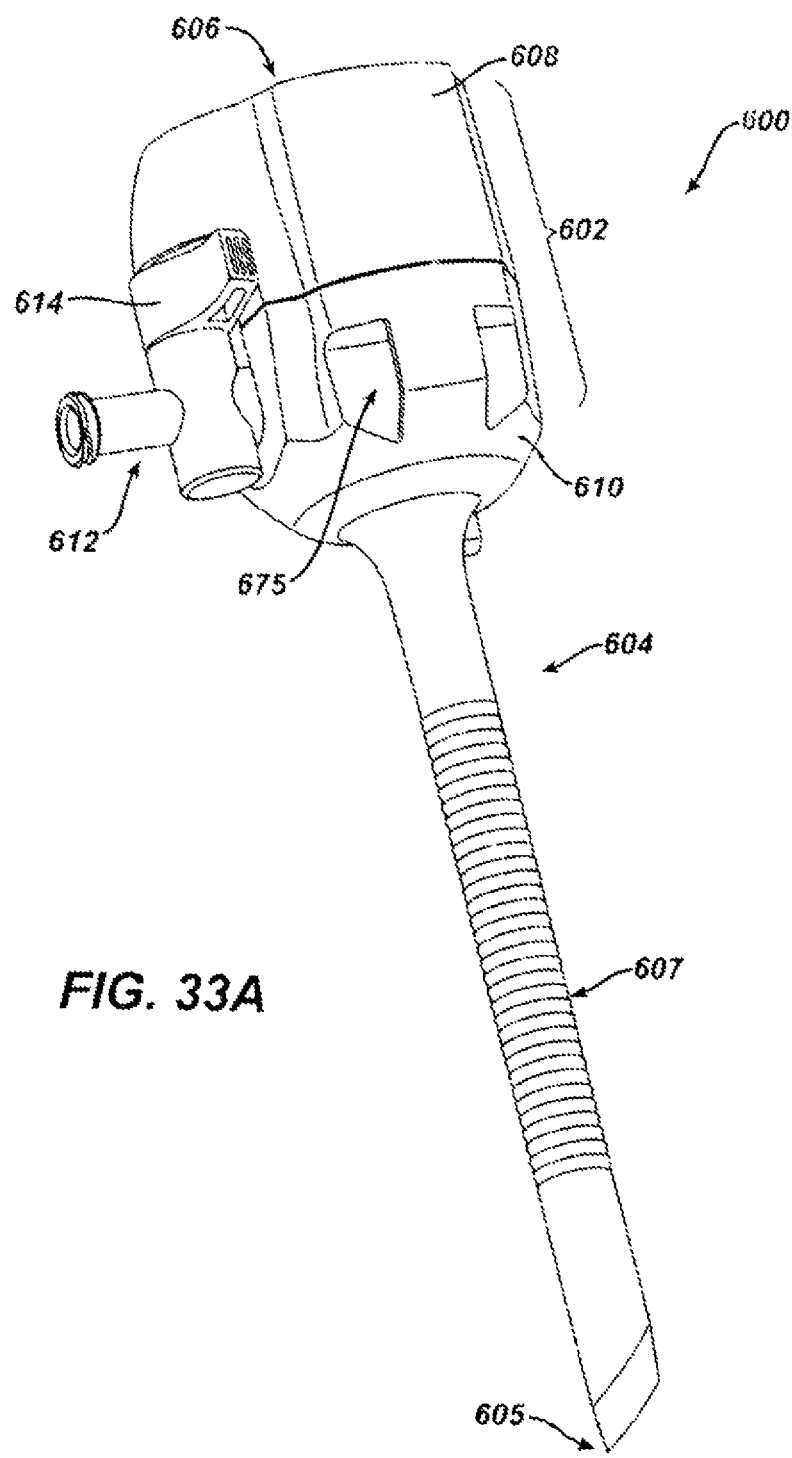
FIG. 33A is a perspective view of another embodiment of a trocar having a fluid removing system disposed therein.

Another exemplary embodiment of a trocar is illustrated in FIGS. 33A-39. As shown in FIG. 33A, a surgical access device or trocar 600 is provided. While the trocar 600 can have many configurations, it can generally include a housing 602 with a cannula 604 extending distally therefrom. The housing 602 and the cannula 604 can define a working channel 606 extending longitudinally through a center thereof for receiving a surgical instrument. An insufflation port 612 can be coupled to one side of the housing 602 for providing insufflation to the trocar 600. In some embodiments, a fluid removal system which can include a scraper, a wicking element, and/or a sorbent, can be disposed within the housing 602. While the insufflation port 612 can be disposed at many locations on the housing 602, in this particular embodiment, the insufflation port 612 is positioned proximal to the fluid removal system and offset from the working channel 606 such that insufflation gas introduced into the housing by the insufflation port 612 passes distally through the fluid removal system to insufflate the cannula 604 and the body cavity when a surgical instrument is disposed within the working channel. A seal system can also be disposed within the housing 602 to prevent the escape of insufflation gas.

Figure 33B:
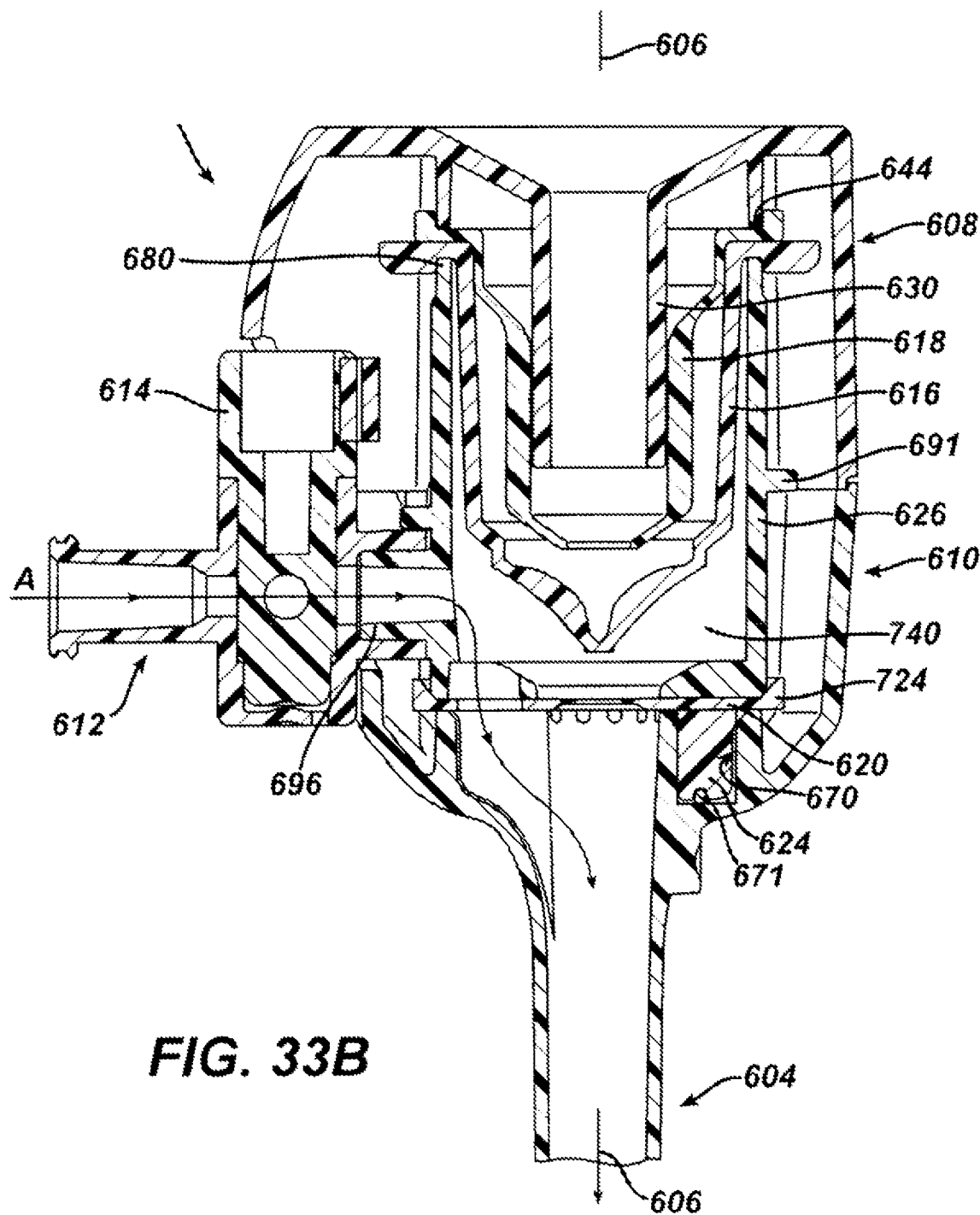
FIG. 33B is a cross-sectional view of the trocar of FIG. 33A showing an exemplary seal system and fluid removal system.

The trocar 600 is illustrated in more detail in FIG. 33B. In some embodiments the housing 602, and optionally the cannula 604, can be a single, integrally formed component, such as in some of the embodiments described above. In other embodiments, such as that illustrated in FIG. 33B, the housing 602 can include a proximal housing 608 and a separate distal housing 610 that couple together to form the housing 602. The proximal housing 608 and the distal housing 610 can enclose the various components of the trocar 600, such as the seal system and the fluid removal system. For example, the proximal and distal housings 608, 610 can enclose a seal system that can generally include a zero-closure seal and an instrument seal, for example, a duckbill seal 616 and a deep-cone seal 618, respectively. The seal system can further include an inner seal retainer 626 for holding and forming a seal with the various internal components, as will be described in more detail below.

The proximal and distal housings 608, 610 can also enclose the fluid removal system, which can be disposed distal to the insufflation port 612. As noted above, and as shown in FIGS. 33B and 38A, the fluid removal system can generally include a scraper 620 for scraping fluid from a surgical instrument inserted therethrough, a wicking element 622 disposed on the scraper (shown in FIG. 38A) for transferring scraped fluid away from the surgical instrument, and/or a sorbent 624 for retaining fluid away from the surgical instrument. Since the insufflation port 612 can be disposed within the housing 602 at a location proximal to the fluid removal system, in general, the fluid removal system can have an insufflation pathway formed therethrough, indicated by arrow A in FIG. 33B, to allow the passage of insufflation gas from a proximal portion of the trocar 600 to a distal portion thereof so that the area below the sealing system, including the cannula 604 and the body cavity, can be pressurized. The pathway can be offset from the working channel 606 so that insufflation gas can pass through the fluid removal system even when a surgical instrument is disposed within and occludes the working channel 606 of the trocar 600. These and other aspects will be described in detail below.

Figure 34A:
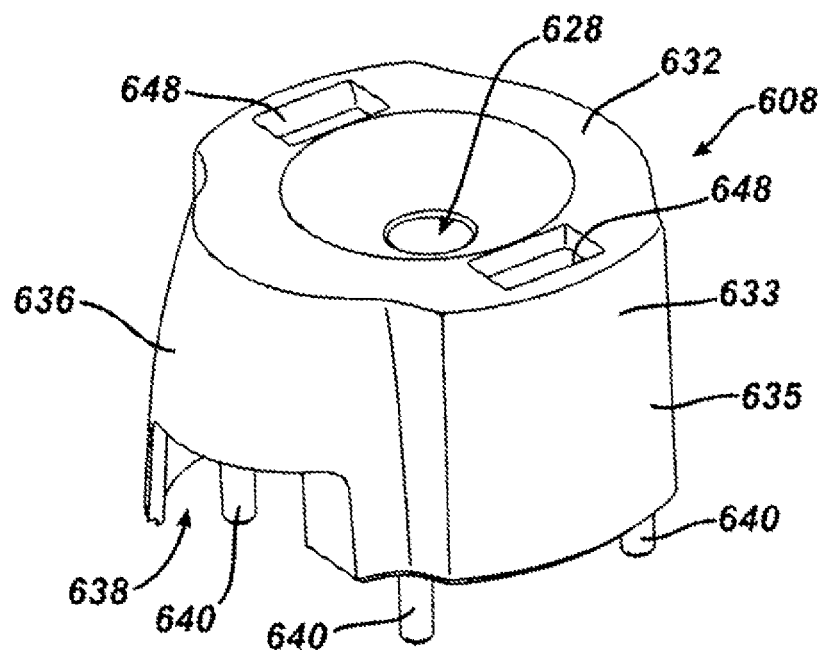
FIG. 34A is a perspective view of one embodiment of a proximal housing of the trocar of FIG. 33A.
Figure 34B:
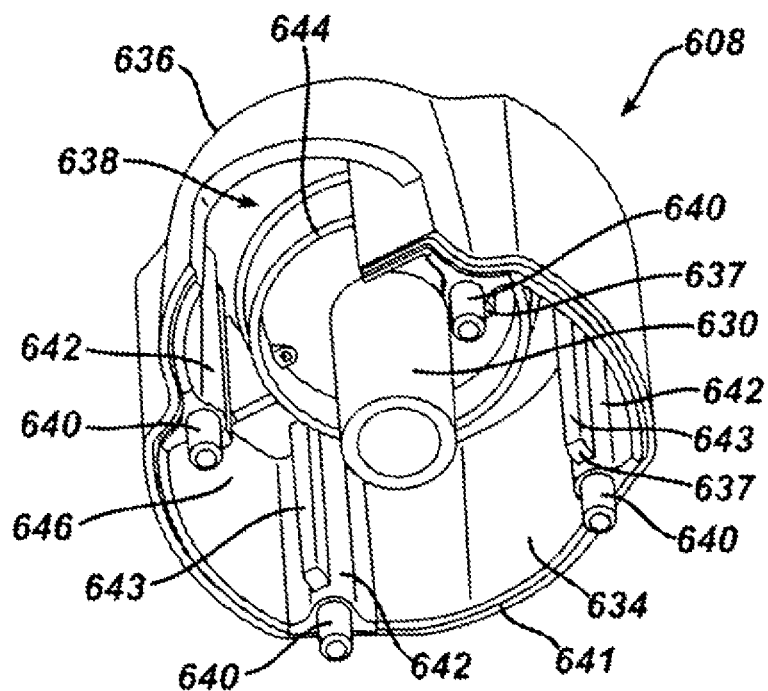
FIG. 34B is another perspective view of the proximal housing of FIG. 34A.

The components of the housing 602 are illustrated in more detail in FIGS. 34A-35, and the proximal housing 608 is shown in detail in FIGS. 34A and 34B. The proximal housing 608 can generally be a substantially rigid, hollow component designed to enclose and retain the seal system and to receive the insufflation port 612 and stopcock 614. The proximal housing 608 can have many configurations, but in the illustrated embodiment, it has a proximal endwall 632 with a sidewall 633 extending substantially orthogonally and distally therefrom. The proximal housing 608 can be generally open distally, without a distal endwall, to allow the distal end to mate to the distal housing. A cavity formed in the proximal housing can house the various inner components of the trocar 600 when the proximal housing 608 is combined with the distal housing 610.

In some embodiments, the proximal endwall 632 can include an opening 628 for receiving a surgical instrument therethrough and for defining the working channel 606 extending along a central longitudinal axis of the trocar 600. A substantially rigid, cylindrical central lumen 630 can extend from the opening 628 a distance into the proximal housing 608 to define the working channel 606. The central lumen 630 can also serve to guide a surgical instrument into the seal system. One or more mating elements 648 can be formed in the proximal endwall 632 of the proximal housing 608 for mating with an obturator for inserting the trocar 600 into tissue.

The proximal endwall 632 and the sidewall 633 of the proximal housing 608 can have an exterior surface 635 and an interior surface 634 that can have any shape as desired to provide the required interior space. The sidewall 633 can optionally include a bowed or distended portion 636 having an opening or cut-out 638 for receiving the insufflation port 612. The sidewall 633 can also include a distal rim 641 that is configured to mate with a corresponding proximal rim 664 (shown in FIG. 35A) of the distal housing 610. The proximal rim 664 and the distal rim 641 can be mated together using any technique known in the art, including but not limited to, interference fit, press fit, adhesive, fastener, etc. For example, the proximal housing 608 can include one or more coupling members 640 for mating to the distal housing 610. The illustrated embodiment includes four coupling members 640 each extending from a coupling lumen 642. The lumens 642 can be integrally formed with and/or rigidly coupled to the interior surface 634 of the sidewall 633, and the coupling members 640 can extend distally therefrom. The coupling members 640 can be substantially rigid, elongate pin-like components that are configured to be disposed within corresponding coupling lumens 666 (shown in FIG. 35A) of the distal housing 610. When the coupling members 640 are mated with the lumens 666, a secure coupling can be formed between the proximal and distal housings 608, 610 by way of, for example, an interference fit, a press fit, or an adhesive. A person having ordinary skill in the art will appreciate the variety of ways that the proximal and distal housings 608, 610 can be mated together.

In one embodiment, each coupling lumen 642 can have a protrusion or rib 643 extending radially outward therefrom, as shown in FIG. 34B. While the ribs 643 can have many configurations, in the illustrated embodiment, the ribs 643 are rectangular shaped protrusions that generally extend along a length of the coupling lumen 642. Two of the ribs 643 located on one side of the cut-out 638 can be orientated toward one another and the other two ribs 643 located on the opposite side of the cut-out 638 can be oriented toward one another, as shown in FIG. 34B. The ribs 643 can be configured to engage pads 693 formed on a flange 691 of the inner retainer 626 (shown in FIGS. 36 and 37A). The ribs 643 can prevent the inner retainer 626 from floating within the proximal and distal housing 608, 610 and can thereby ensure adequate compression of the seals 616, 618 and the scraper 620 to maintain a pneumo seal. In particular, the ribs 643 can ensure that the gap between a proximal sealing flange 644 of the proximal housing 608 and a proximal retainer rim 680 of the retainer 626 is of an appropriate height to provide the desired compression of the seals 616, 618 disposed within the gap. For example, when the proximal housing 608 is fully seated on and mated with the distal housing 610, a distal end 637 of each rib 643 abuts and engages a corresponding pad 693 on the flange 691 of the inner retainer 626. The distance between the distal end 637 of each rib 643 and the proximal sealing flange 644 of the proximal housing 608 can set the gap between the proximal sealing flange 644 and the proximal retainer rim 680 of the retainer 626 (described in more detail below). In this way, the amount of compression on the seals 616, 618 seated therebetween can be predicted. Similarly, the length of the ribs 643 can also set the gap between the inner retainer 626 and the distal housing 610, thus controlling the amount of compression of the scraper 620, also described in more detail below.

The proximal housing 608 can also include features for retaining and sealing against the seals 616, 618. For example, in some embodiments, the proximal housing 608 can include a proximal sealing flange 644 formed on an interior surface 646 of the proximal endwall 632, as shown in FIG. 34B. The proximal sealing flange 644 can be a substantially rigid cylindrical member having a diameter greater than a diameter of the central lumen 630, but less than a width of the proximal housing 608. In general, the proximal sealing flange 644 can act with the seal retainer 626 to retain and form a seal with the duckbill seal 616 and the deep-cone seal 618, as will be described in detail below.

Figure 35A:
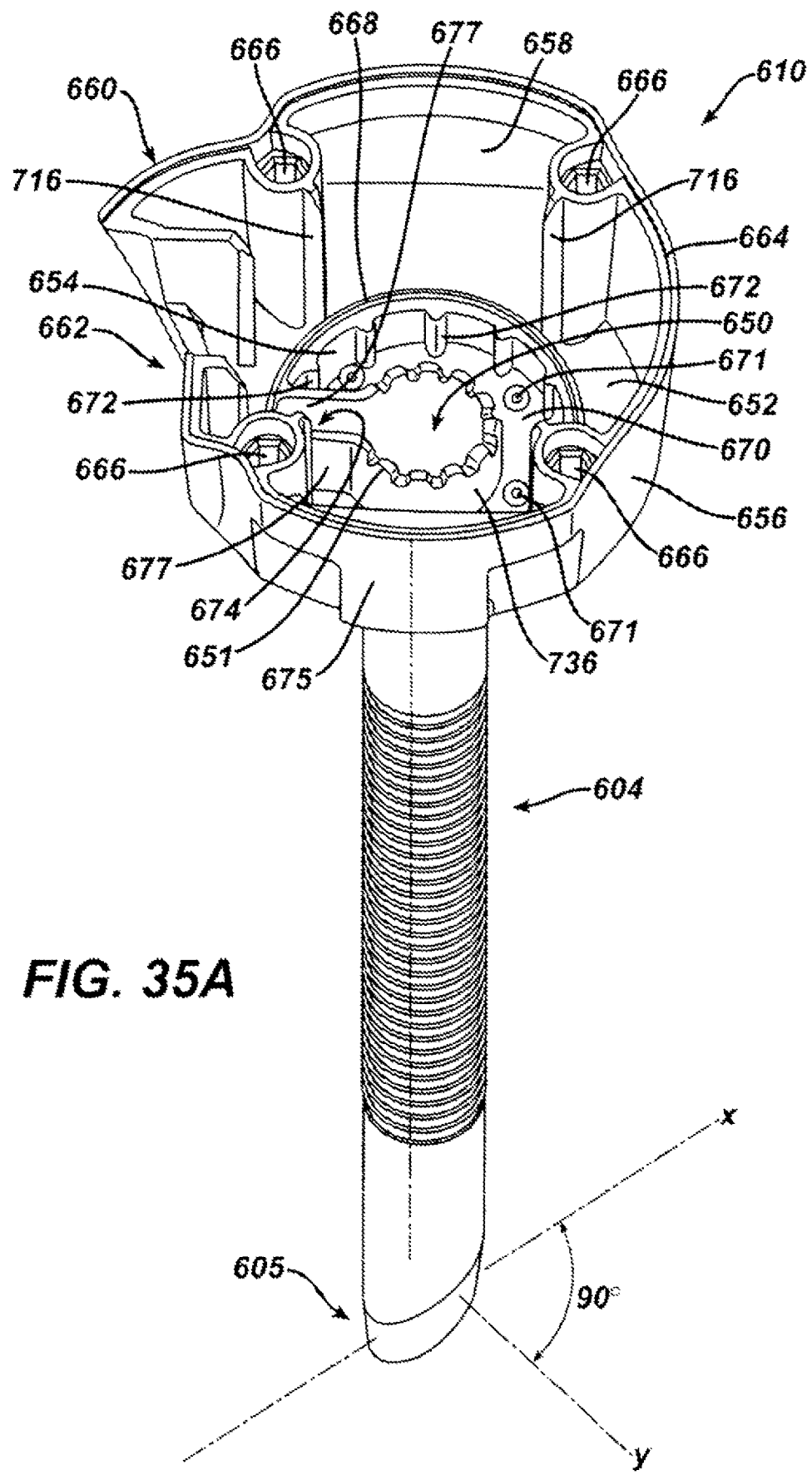
FIG. 35A is a perspective view of one embodiment of a distal housing of the trocar of FIG. 33A.
Figure 35B:
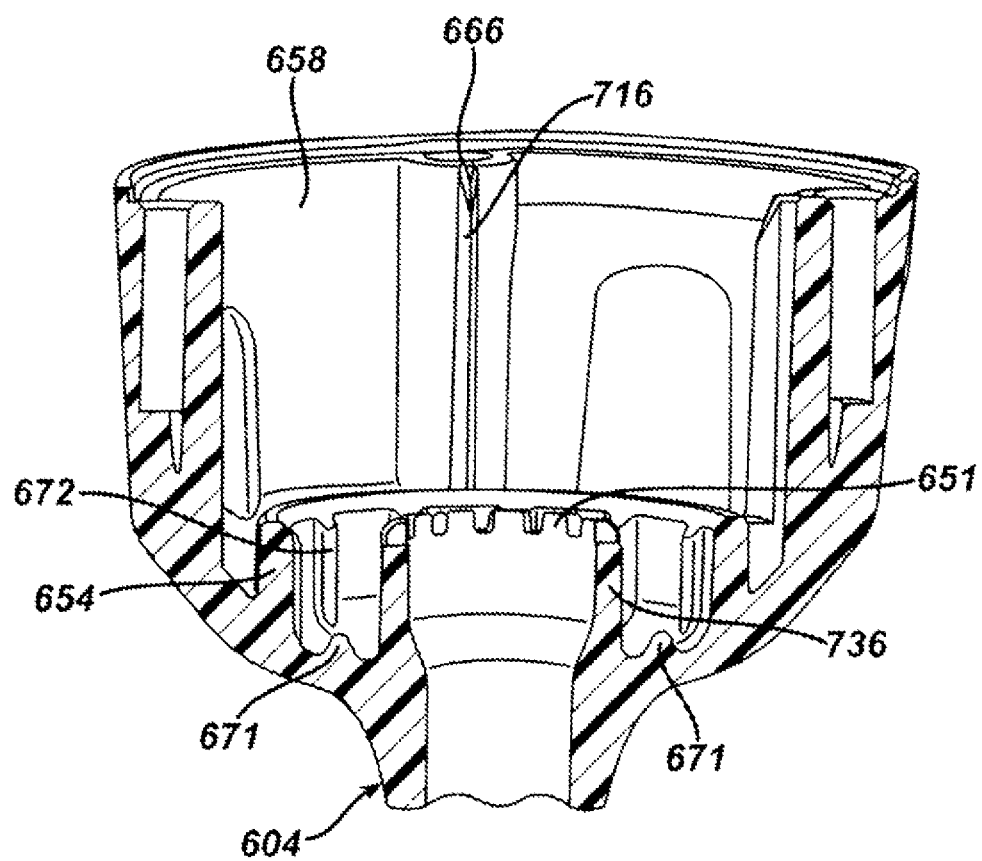
FIG. 35B is a perspective cross-sectional view of the distal housing of FIG. 35A.

The distal housing 610 can also have many configurations and one embodiment is shown in more detail in FIGS. 35A and 35B. Similar to the proximal housing 608, the distal housing 610 can generally be a substantially rigid, hollow component designed to enclose and retain the fluid removal system and to receive the insufflation port 612. The distal housing 610 can have many configurations, but in the illustrated embodiment it has a distal endwall 652 with a sidewall 654 extending substantially orthogonally and proximally therefrom. The distal housing 610 can be generally open proximally, without a proximal endwall, and the sidewall 654 can define a cavity made for housing the various inner components of the trocar 600 when the distal housing 610 is combined with the proximal housing 608.

The distal housing 610 can also generally be configured for receiving a surgical instrument therethrough and it can be configured to mate with the insufflation port 612 and the proximal housing 608. For example, the distal housing 610 can include an opening 650 formed in its distal endwall 652 for receiving a surgical instrument therethrough and for defining the working channel 606 extending into the cannula 604. In some embodiments, the distal endwall 652 and the sidewall 654 can have an exterior surface 656 and an interior surface 658 and can have any shape as desired that provides the required interior space. The sidewall 654 can optionally include a bowed or distended portion 660 that includes an opening or cut-out 662 for receiving the insufflation port 612. The sidewall 654 can also include a proximal rim 664 that is configured to mate with a corresponding distal rim 641 (shown in FIG. 34B) of the proximal housing 608. The proximal rim 664 and the distal rim 641 can be mated together using any technique known in the art, including but not limited to, interference fit, press fit, adhesive, fastener, etc. For example, the distal housing 610 can include one or more coupling lumens 666 for mating to the proximal housing 608. The illustrated embodiment includes four coupling lumens 666 each integrally formed with and/or rigidly coupled to the interior surface 658 of the sidewall 656. The coupling lumens 666 can be substantially rigid, hollow components that are configured to receive corresponding coupling members 640 (shown in FIG. 34B) of the proximal housing 608 to securely mate the proximal and distal housings 608, 610 together as described above.

The distal housing 610 can also include features for retaining and sealing against the scraper 620. For this purpose, the distal housing 610 can include a distal sealing flange 668 formed on the distal endwall 652. The distal sealing flange 668 can be a substantially rigid cylindrical member having a diameter greater than a diameter of the opening 650, but less than a width of the distal housing 610. In general, the distal sealing flange 668 can act with the seal retainer 626 to retain and form a seal with the fluid removal system, as will be described in detail below. In addition, the distal housing 610 can include a plurality of ridges 651 that are designed to seat and mate with the scraper 620 as will be described in detail below. The ridges 651 can be formed integrally with a proximal surface of a wall 736 extending from the floor of the distal housing 610, and can have high and low portions that define each ridge 651.

A cavity 670, shown in FIG. 35A, can be formed between the opening 650 and the distal sealing flange 668 for seating the sorbent 624. The cavity can have one or more ridges, for example, a plurality of ridges 672 formed around an interior surface of the distal sealing flange 668 for providing frictional engagement with the sorbent 624. The cavity 670 can also include a plurality of features, for example, four nubs 671 that extend proximally from the floor of the cavity 670 and that are designed to engage the sorbent 624 and press the sorbent 624 into engagement with the scraper 620 as will also be described in more detail below. As will be appreciated by those skilled in the art, any sort of feature sufficient to press the sorbent 624 into engagement with the scraper 620 can be used within the cavity 670. The nubs 671 can be formed integrally with the distal housing 610 or can be coupled thereto by an adhesive or other fixation mechanism.

The distal housing 610 can optionally be integrally formed with the cannula 604. The cannula 604 can extend distally from the distal housing 610 and can terminate distally in an angled portion that forms a distal piercing tip 605 that facilitates entry through tissue into a body cavity. In some embodiments, a longest point of the angled distal tip 605 of the cannula 604 can be oriented relative to the distal housing 610 such that it is aligned with the insufflation port 612, although it can have any orientation desired. The distal housing 610 can also have one or more suture loops or other suture tie down features 675 formed around an outer perimeter of an exterior surface 656 thereof. Each suture tie down feature 675 can define an opening or pathway formed therethrough for receiving suture to help better secure the trocar 600 when it is disposed in tissue. The suture tie down feature 675, shown in FIG. 33A, can have any angular orientation relative to the angled distal tip 605 of the cannula 604, but in one embodiment, at least one tie down feature 675 is offset by 90 degrees from the longest point of the angled distal piercing tip 605. In other embodiments, the suture tie down feature 675 can be positioned in line with the angled distal tip 605 of the cannula 604, or offset by 180 degrees therefrom.

Figure 36:
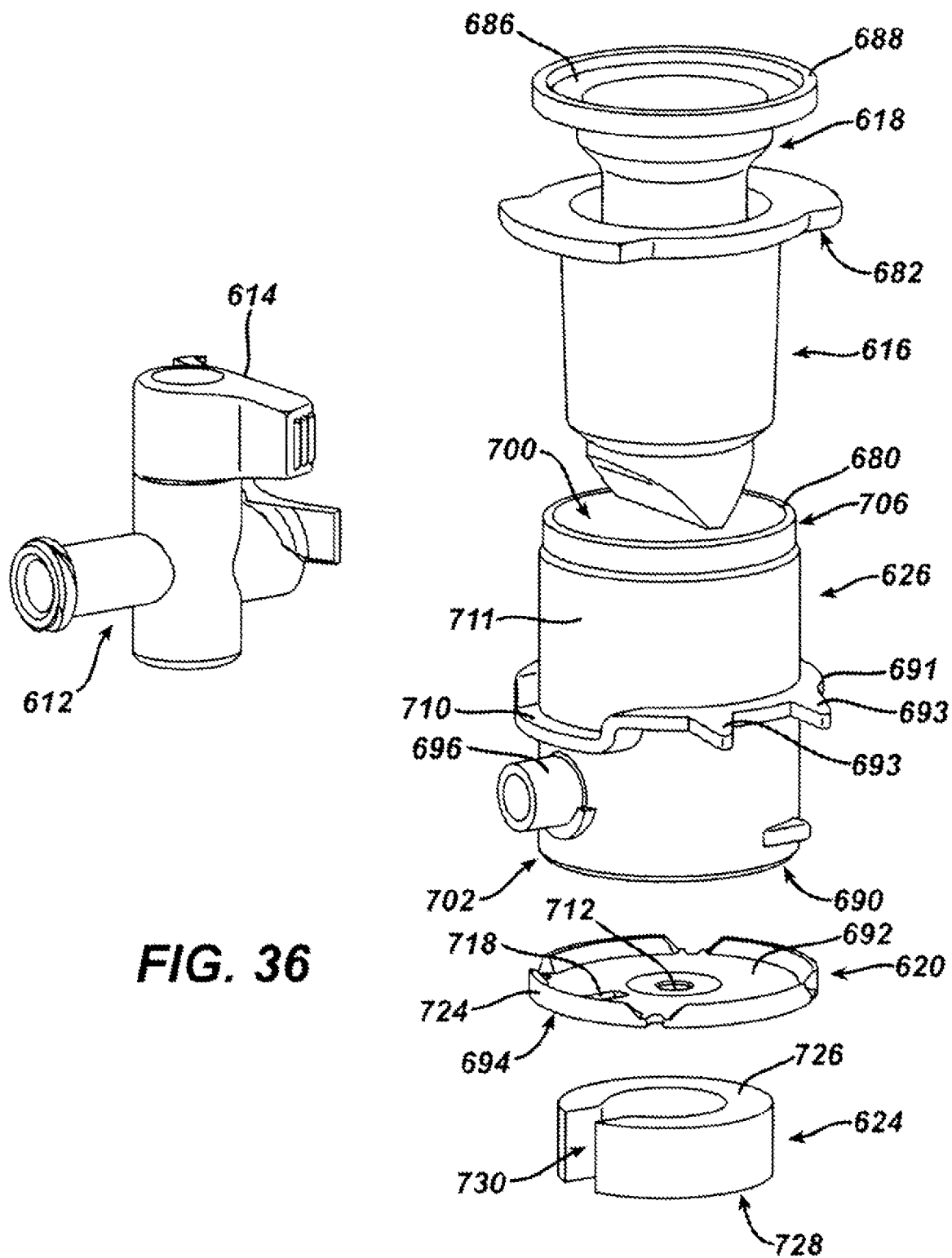
FIG. 36 is an exploded view of the seal system and fluid removal system of the trocar of FIG. 33A.

While the seal system and fluid removal system disposed within the housing 602 can have many different configurations, one exemplary embodiment of these systems is shown in more detail in FIG. 36. As noted above, the illustrated seal system includes a duckbill type channel seal 616, a deep-cone type instrument seal 618, and an inner seal retainer 626 for securing the sealing elements within the trocar 600. As will be appreciated by those having ordinary skill in the art, any suitable sealing combination can be utilized within the housing 602 that is effective to maintain insufflation of the cannula 604 and the body cavity during use. Thus, the sealing combination can generally include both a zero-closure seal and an instrument seal and/or a single seal that is capable of both zero-closure and sealing around an instrument. In the illustrated embodiment, the deep-cone seal 618 is disposed within the duckbill seal 616 such that an instrument inserted into the working channel 606 through the opening 628 in the proximal housing 608 will encounter the deep-cone seal 618 first. Since it is positioned proximal to the duckbill seal 616, the deep-cone seal 618 will form a seal around the surgical instrument before the surgical instrument encounters and opens the duckbill seal 616. In this way, insufflation can be maintained during insertion of the instrument into the trocar 600.

While there are various ways to retain the seals within the housing 602, in the illustrated embodiment, the seals 616, 618 are disposed within and coupled to the seal retainer 626. The seal retainer 626 and the proximal and distal housings 608, 610 can generally function together to seal the working channel 606 by pressing and sealing against a perimeter of the seals 616, 618. In particular, as shown in FIGS. 36-37B, the seal retainer 626 can be a substantially rigid cylindrical component that defines a portion of the working channel 606 and seals the working channel 606 from a region in the housing 602 outside of and/or surrounding the retainer 626. The seal retainer 626 fits within the housing 602 and that can have a proximal end 706 and a distal end 702. The proximal end 706 can have an opening 700 that is substantially the same diameter as an outer diameter of the retainer 626, although it can have any diameter as necessary to accommodate the seals 616, 618. The distal end 702 can include a distal endwall 708 with an opening 704 extending therethrough. The opening 704 can have any diameter as needed, for example, a diameter that is smaller than the outer diameter of the retainer 626, but at least large enough to receive a surgical instrument. The retainer 626 can have a sidewall 711 extending between its proximal and distal ends 706, 702. In some embodiments, the distal endwall 708 can include a plurality of ribs 707 extending radially from the opening 706, as shown in FIG. 37C. The ribs 707 can be configured for maintaining positive contact between the scraper 620 and the sorbent 624.

As noted above, in some embodiments the seals 616, 618 can be retained by and sealed between the seal retainer 626 and the sealing flange 644 of the proximal housing 608. In particular, the retainer 626 can have a proximal retainer rim 680 that can engage a distal surface 682 of a flange 684 formed on the duckbill seal 616. The proximal sealing flange 644 of the proximal housing 608 can engage the proximal surface 686 of the flange 688 on the deep-cone seal 618. As shown most clearly in FIG. 33B, when the trocar 600 is assembled, the proximal retainer rim 680 and the proximal sealing flange 644 compress together around the outer perimeter of the flanges 684, 688 and form a seal thereagainst such that the working channel 606 is sealed for the purposes of insufflation. As well, the proximal rim 680 and the sealing flange 644 can retain the seals 616, 618 within the housing 602. As noted above, the amount of spacing between the distal end 637 of the ribs 643 in the proximal housing 608 and the proximal sealing flange 644 of the proximal housing 608 can be used, at least in part, to predict and control the amount of compression of the seals 616, 618.

As also noted above, at least a portion of the fluid removal system can be retained by and sealed between the seal retainer 626 and the sealing flange 668 of the distal housing 610. In particular, the seal retainer 626 can include a distal retainer rim 690 that can engage a proximal surface 692 of the scraper 620. In addition, the distal sealing flange 668 in the distal housing 610 can engage a distal surface 694 of the scraper 620. When the trocar 600 is assembled, the distal retainer rim 690 and the distal sealing flange 668 compress together around the outer perimeter of the scraper 620 to form a seal thereagainst such that the working channel 606 is sealed for the purposes of insufflation. As well, the distal rim 690 and the sealing flange 668 can retain the scraper 620 within the housing 602.

Figure 37A:
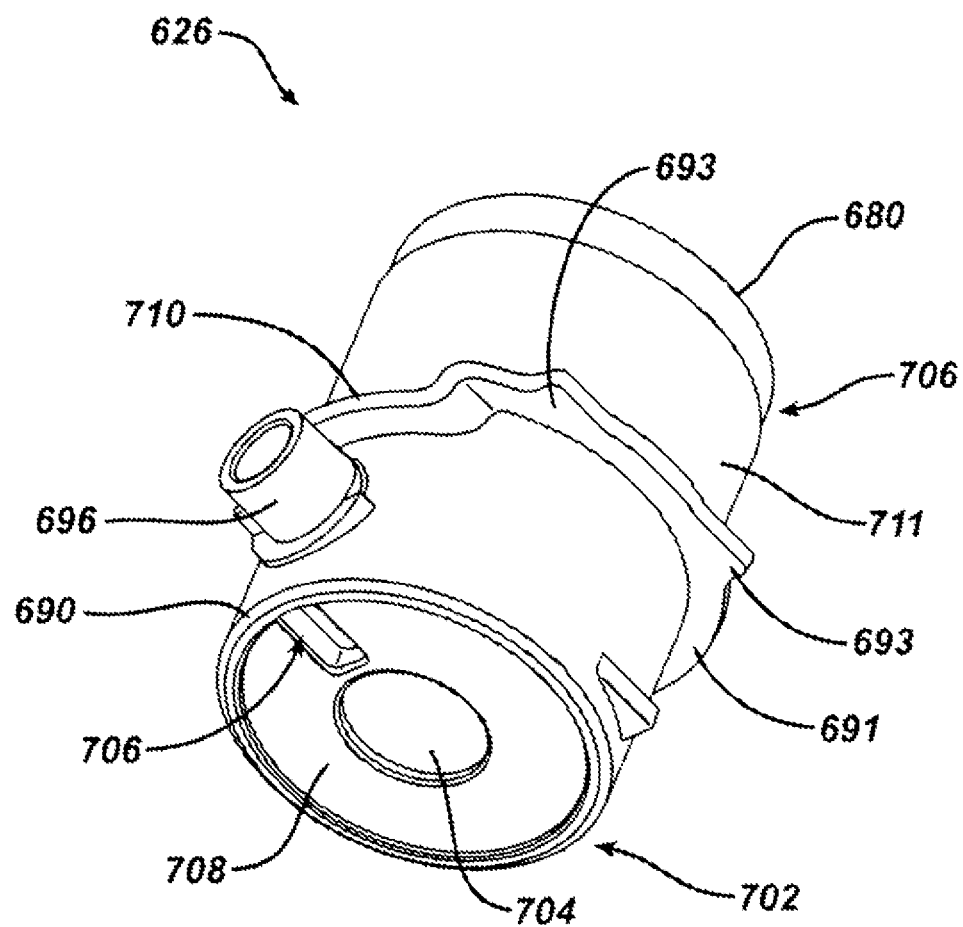
FIG. 37A is a perspective view of an exemplary seal retainer of the trocar of FIG. 33A.
Figure 37B:
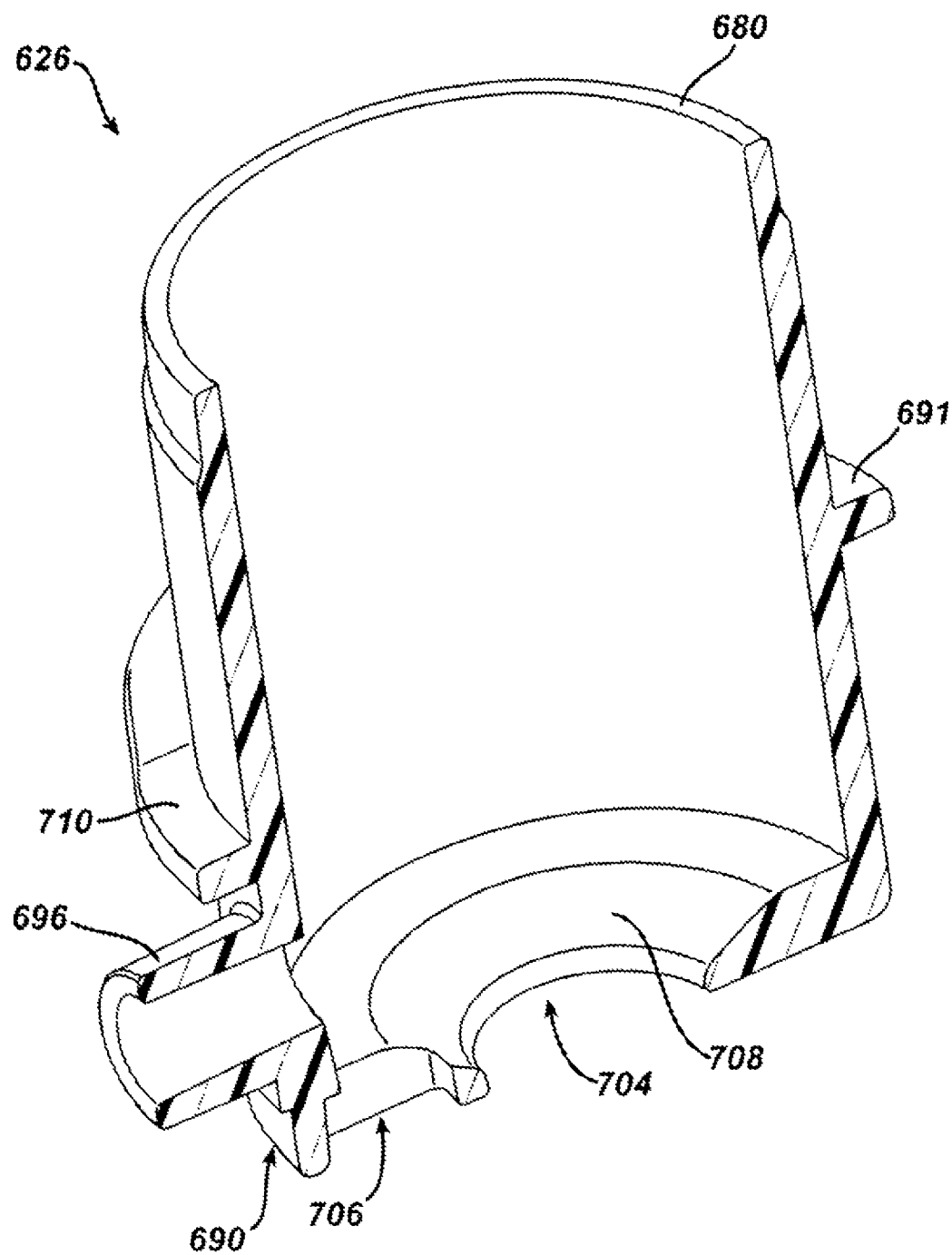
FIG. 37B is a cross-sectional view of the seal retainer of FIG. 37A.
Figure 37C:
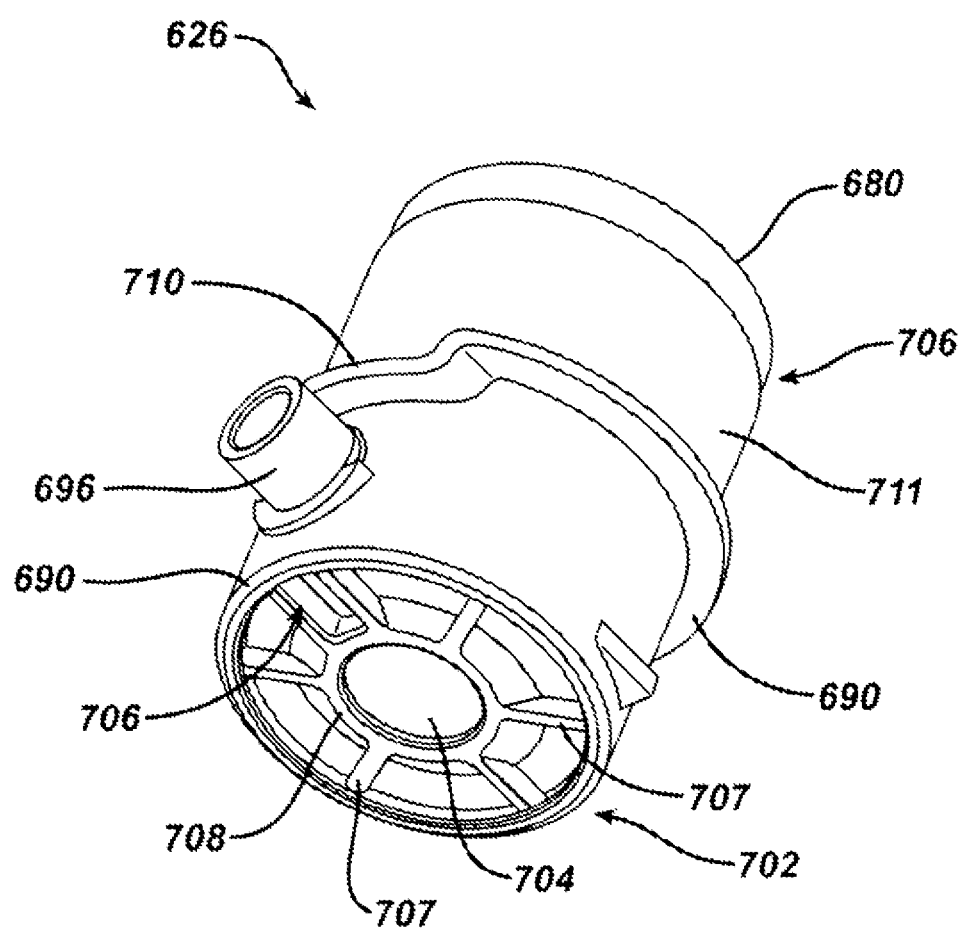
FIG. 37C is a perspective view of another exemplary seal retainer for use in the trocar of FIG. 33A.

As shown in FIGS. 33B, 36, and 37A the seal retainer 626 can further include a median flange 691 extending radially outward from the retainer 626 and disposed around an outer circumference thereof. The median flange 691 can generally be disposed anywhere along a length of the retainer 626, but in the illustrated embodiment it is disposed near a mid-portion of the retainer 626. The median flange 691 can be configured to engage an inner sidewall of the proximal and distal housings 608, 610 at a point where the proximal and distal housings 608, 610 mate together. In this way, the retainer 626 can be retained and secured within the housing 602. As noted above, the flange 691 can also include a plurality of pads 693 configured to engage ribs 643 in the proximal housing 608. The length of the ribs 643 can be used to predict and control the compression of the seals 616, 618 and the scraper 620. In some embodiments, the median flange 691 can have a portion 710 that curves or dips distally to accommodate the structure of the proximal and distal housings 608, 610 near the coupling point for the insufflation port 612.

In some embodiments, the seal retainer 626 can also include a port 696 for receiving the insufflation port 612. An opening 706 can be formed in a distal endwall 708 of the retainer 626 to allow insufflation gas to flow from the port 696 and through the distal endwall 708 to insufflate the cannula 604 and the body cavity.

As noted above, the trocar 600 can include a fluid removal system generally configured to remove fluid from a surgical instrument and transfer and store the fluid at a location away from the working channel 606 and any surgical instrument inserted therethrough. The fluid removal system can have many configurations, but as shown in FIG. 36, and as noted above, it can include the scraper 620 having the wicking element 622 formed thereon (shown in FIG. 38A) and the sorbent 624 positioned adjacent to the scraper 620 to sorb fluids wicked by the wicking element 622.

Figure 38A:
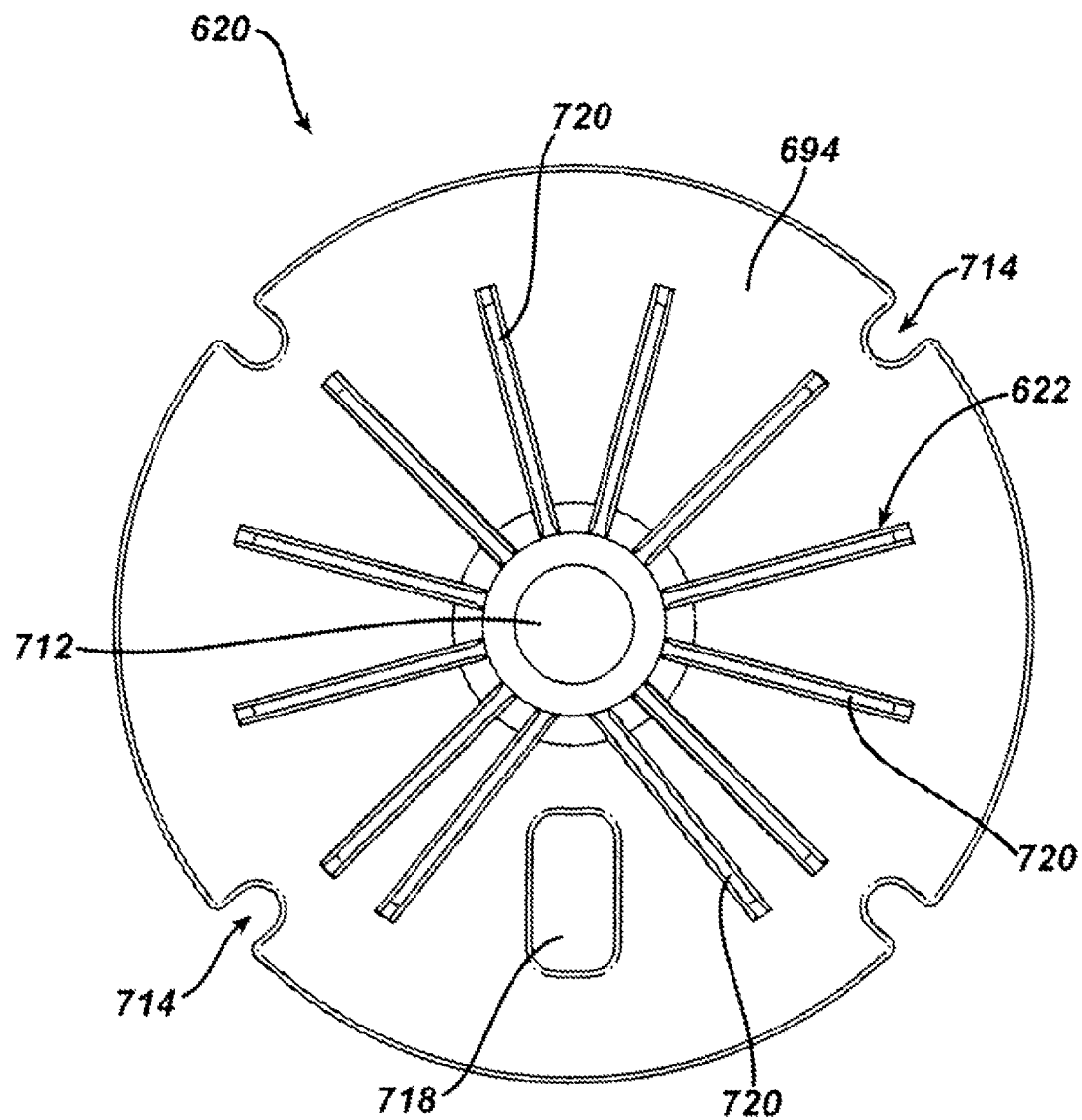
FIG. 38A is a bottom view of an exemplary scraper and wicking element for use in the trocar of FIG. 33A.
Figure 38B:
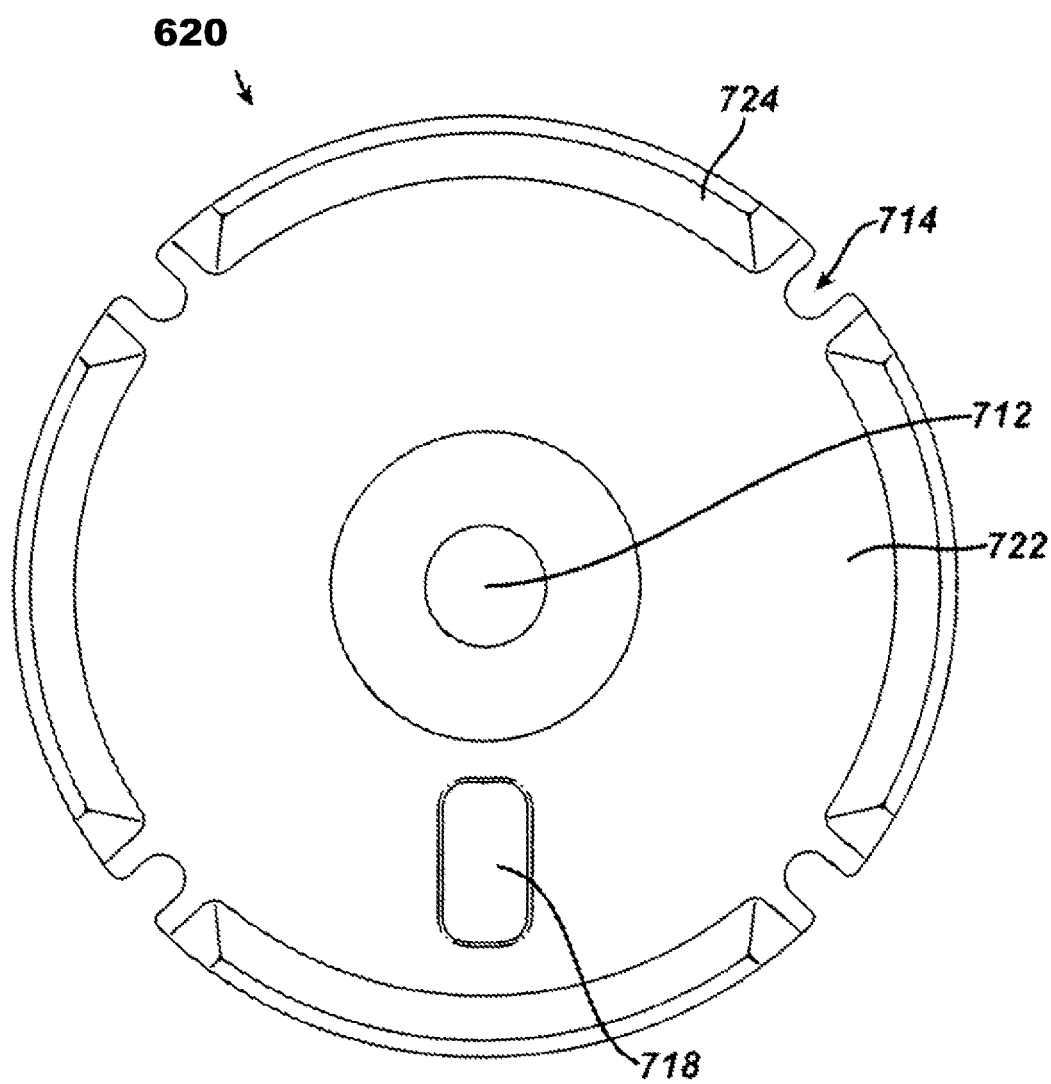
FIG. 38B is a top view of the scraper of FIG. 38A.
Figure 38C:
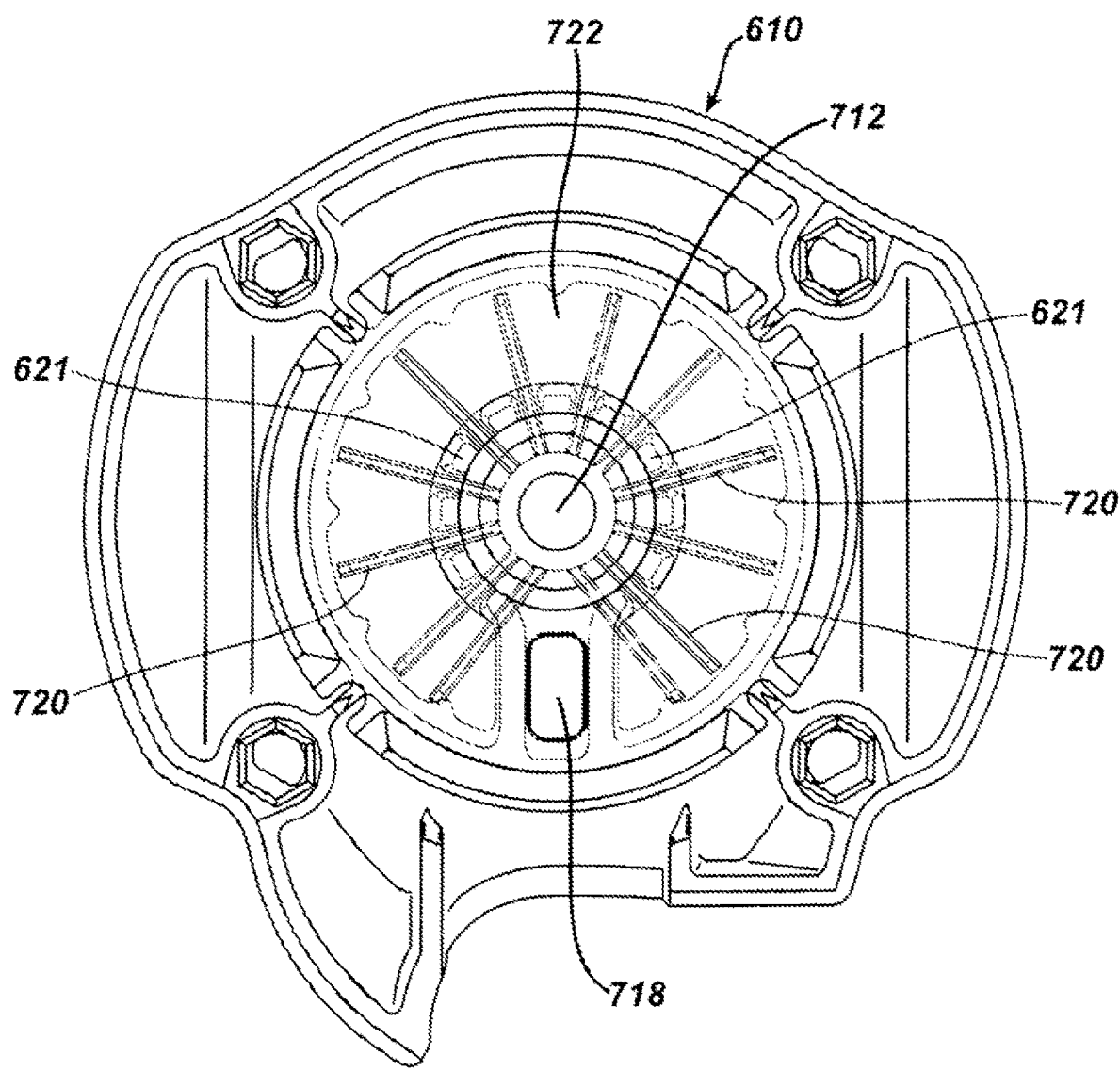
FIG. 38C is a top view of the scraper of FIG. 38A seated within an exemplary distal housing.
Figure 39:
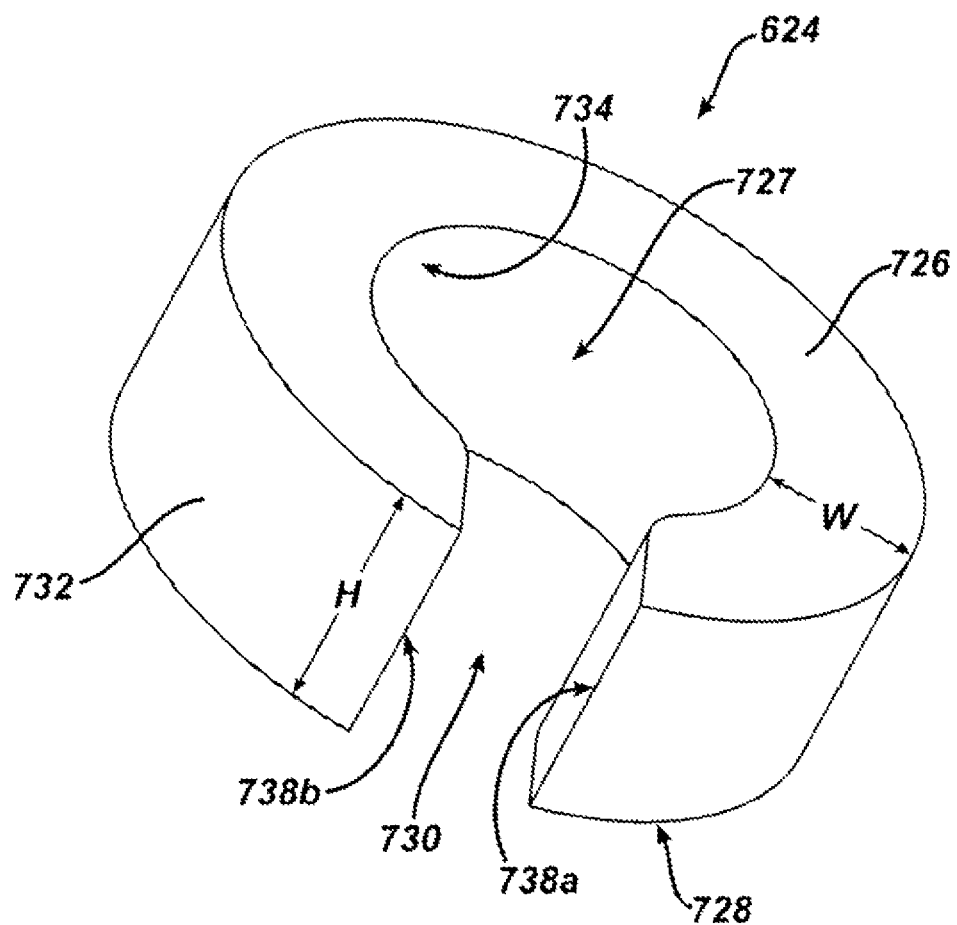
FIG. 39 is a perspective view of an exemplary sorbent for use in the trocar of FIG. 33A.

The scraper 620 is shown in more detail in FIGS. 38A-38C and can have any of the same or similar features and configurations previously described. The scraper 620 can be a substantially circular component having a proximal surface 722 and a distal surface 694. An opening 712 can be formed through a center of the scraper 620 for receiving a surgical instrument therethrough. The opening 712 can have a diameter substantially the same as, or slightly smaller than, a diameter of a surgical instrument inserted therethrough so that the opening 712 scrapes along the outside of a surgical instrument as it is passed therethrough to remove fluid therefrom. As noted in the previous embodiments, the scraper 620 can be formed of a flexible material and can therefore invert proximally as a surgical instrument is being withdrawn through and scraped by the opening 712.

There are many ways in which the scraper 620 can be retained within the housing 602. As noted above, in one embodiment the scraper 620 can be retained by and disposed between the distal retainer rim 690 of the retainer 626 and the distal sealing flange 668 of the distal housing 610. Because the scraper 620 can be formed of a flexible and/or compressible material, as the rim 690 and the flange 668 engage the outer perimeter of the scraper 620, the outer perimeter of the scraper 620 can be compressed therebetween and a seal can be formed between the scraper 620, the rim 690, and the flange 668. As noted above, the amount of spacing between the distal end 637 of the ribs 643 in the proximal housing 608 and distal retainer rim 690 can be used, at least in part, to predict and control the amount of compression of the scraper 620. The outer perimeter of the scraper can optionally include a lip 724 extending proximally from the proximal surface 722. The rim 690 and the flange 668 can compress the scraper 620 at a location radially inward of the lip 722, as can be seen in FIG. 33B.

In some embodiments, the scraper 620 can include features to assist in securing the scraper 620 within the housing 602. For example, the outer-most perimeter of the scraper 620 can include one or more indentations, for example, four indentations 714 for receiving protrusions 716 in the distal housing 610. The protrusions 716 are coupled to and/or integrally formed with the lumens 666 and serve to further stabilize the scraper 620 within the distal housing 610. The scraper 620 can also include an opening or hole 718 that can align with the opening 706 formed in the retainer 626 to allow insufflation gas to flow therethrough. The hole 718 can have any size or shape known in the art that is sufficient to allow the flow of insufflation gas therethrough. In the illustrated embodiment, the hole 718 is substantially rectangular and of a size to match the opening 706. The hole 718 can be offset from the opening 712 such that an axis extending through the center of the hole 718 that is parallel with the longitudinal axis of the trocar 600 is offset a distance away from the longitudinal axis of the trocar 600.

As noted above, the scraper 620 can also include features formed thereon, such as the wicking element 622, for wicking fluid away from the working channel 606. While the wicking element 622 can take any form suitable to wick fluid away from the opening 712, in the illustrated embodiment, the wicking element 622 can be one or more channels 720 formed in the distal surface 694. The channels 720 can extend partially into the distal surface 694 of the scraper 620 and can have a depth suitable to contain and transfer fluid away from the opening 712. The channels 720 can begin at the opening 712 and extend radially outward therefrom, or they can begin a radial distance away from the opening 712 and extend radially outward therefrom, as shown in FIGS. 38A and 38C. Similarly, the channels 720 can extend all the way to the outer-most circumference of the scraper 620, or they can stop a distance away from the outer-most circumference, as shown in FIG. 38A. A person skilled in the art will appreciate the variety of configuration possible for the channels 720.

There can also be any number of channels 720 formed in the scraper 620 as desired and they can be arranged around the scraper 620 with even spacing therebetween and/or with uneven spacing therebetween. In the illustrated embodiment, a plurality of channels 720 are formed in the scraper 620 and the majority thereof are generally spaced evenly around the scraper 620. However, channels 720 near the hole 718 can differ is spacing. For example, four of the channels 720 near the hole 718 are not spaced evenly with the other channels 720. Instead two channels 720 on one side of the hole 718 and two channels 720 on the other side of the hole 718 are spaced closer together to provide room for the hole 718 and to ensure that fluid is directed away from the hole 718. As noted above, the scraper 620 can be seated on the ridges 621 formed on the wall 736 of the distal housing 610.

In particular, the ridges 621 can engage a narrow circumference of the scraper 620 that is closer to the center opening 712 than to the outer-most circumference, for example about one-quarter to one-third of the way along a length of the channels 720, although any configuration is possible. This narrow circumference of engagement allows the scraper 620 to be seated within the distal housing 610 without causing the channels 720 to buckle or collapse, as would likely happen with a wider area of engagement. The channels 720 can be aligned with the ridges 621, as illustrated in FIG. 38C, such that each channel 720 is aligned with a low portion or valley of the ridges 621 to ensure fluid flow through the channel 720. Each high portion or peak of the ridges 621 extends proximally between the channels 720. The channels 720 can be adjacent to and in contact with the sorbent 624 to wick fluid to the sorbent 624.

The sorbent 624 can also have many shapes and configurations, as noted in detail above. In the embodiments illustrated in FIGS. 36 and 39, the sorbent 624 can be substantially c-shaped and/or substantially circular shaped with a cut-out 730 in one side. A center opening 727 of the sorbent 624 can have a diameter that is greater than a diameter of the working channel 606 of the cannula 604 and/or of the opening 712 formed in the scraper 620. The sorbet 624 can have a proximal surface 726 and a distal surface 728, as well as an outer surface 732 and an inner surface 734. The sorbent 624 can generally have a rectangular cross-section with a width W and a height H, and in some embodiments, the width W can be less than a height H. In other embodiments, the sorbent 624 can have a circular cross-section, a triangular cross-section, etc. The sorbent 624 can generally have a size suitable to be positioned within the cavity 670 formed within the distal housing 610. The cut-out 730 can have any width and configuration, and in the illustrated embodiment it has a width similar to but larger than the size of the hole 718 in the scraper 620 and the opening 706 in the retainer 626. For example, the cut-out 730 can have a width larger than parallel walls 677 within the distal housing 610 defining an insufflation pathway 674 through the distal housing 610. The hole 718 in the scraper 620 and the opening 706 in the retainer 626 can have a width substantially the same as the width of the walls 677 in the distal housing 610. The larger width of the cut-out 730 compared with the width of the hole 718 and the opening 706 is to ensure that the insufflation pathway remains clear of any fluid retained in the sorbent 624. In use, the cut-out 730 is preferably aligned with the hole 718 and the opening 706.

As noted above, the sorbent 624 can be seated within the cavity 670 and on top of the nubs 671. The nubs 671 can engage the distal surface 728 of the sorbent 624 and can elevate the sorbent 624 to bias the sorbent 624 into engagement with the scraper 620. In particular, the proximal surface 726 of the sorbent 624 can be pressed into engagement with the distal surface 694 of the scraper 620. In some embodiments there can be a compression force that results in an interference contact between the surfaces 726, 694 in the range of about 1/1000 to about 18/1000 inches to ensure sufficient contact between the two surfaces 726, 694 without blocking the channels 720 and preventing fluid transfer. The engagement between the two surfaces 726, 694 provided by the nubs 671 results in efficient transfer of fluid from the channels 720 of the wicking element 622 to the sorbent 624. Fluid scraped by the opening 712 can travel radially outward from the opening 712 through the channels 720, past the ridges 621, and into contact with the sorbent 624 to be sorbed thereby.

When the trocar is assembled, all of the holes, openings, and pathways through the various components of the fluid removal system can be aligned to form an insufflation pathway through the fluid removal system, as shown by arrow A in FIG. 33B. More particularly, the sorbent 624 can be positioned within the cavity 670 within the distal housing 610. Ridges 672 can engage the outer surface 732 of the sorbent 624, while the inner surface 734 engages a wall 736 defining the opening 650 that extends into the cannula 604. Opposed sides 738a, 738b of the cut-out 730 can be positioned on either side of the channel or pathway 674 extending from the opening 650 within the distal housing 610. The pathway 674 can be aligned with the port 696 of the retainer 626 to allow the insufflation gas to flow therethrough. The scraper 620 can be positioned on top of or proximal to the sorbent 624 such that the outer perimeter of the scraper 620 rests on the distal sealing flange 668 of the distal housing 610, and such that the wicking element 622 is adjacent to and in contact with the sorbent 624. In this way, fluid scraped by the scraper 620 will be wicked along the channels 720 and sorbed by the sorbent 624. The sorbent 624 will hold the fluid away from the working channel 606, and thus away from any instruments inserted through the working channel 606. The hole 718 in the scraper 620 can be aligned with the pathway 674 in the distal housing 610 and with the cut-out 730 in the sorbent 624 to allow the flow of insufflation gas therethrough.

Further, the seal retainer 626 can be positioned proximal to the scraper 620 such that the distal rim 690 is positioned on the proximal surface in contact with the outer perimeter of the scraper 620 and forms a seal thereagainst with the distal sealing flange 668. The opening 706 in the retainer 626 can also be aligned with the hole 718 in the scraper 620, the cut-out 730 in the sorbent 624, and the pathway 674 in the distal housing 610 to form the insufflation pathway to allow the flow of insufflation gas therethrough. In this way, insufflation gas from the port 696 passes from an area in the distal housing 610 that is proximal to the fluid removal system through the pathway created by the opening 706, the hole 718, the cut-out 730, and the pathway 674 and into an area distal to the fluid removal system. The insufflation gas can therefore pass into the cannula 604 and into the body cavity through the fluid removal system even when a surgical instrument occludes the opening 712 in the scraper 620.

In use, once the trocar 600 is inserted into a body cavity, the insufflation port 612 can be used to introduce insufflation gas into the housing 602 through the port 696 in the seal retainer 626. In other embodiments, insufflation gas can be introduced into the housing 602 before an instrument is inserted therethrough. The gas can flow into the channel 740 in the retainer 626 near the distal end of the duckbill seal 616 shown in FIG. 33B, and into the insufflation pathway created through the fluid removal system as described above, as well as through the working channel 606. When an instrument is disposed through the trocar 600, the deep-cone seal 618 forms a seal around the instrument to maintain insufflation distal of the seal 618. Further, the surgical instrument occludes the opening 712 in the scraper 620, preventing the flow of gas through the working channel 606. The insufflation pathway that extends through the fluid removal system is offset from the working channel 606, and thus insufflation gas can flow through the insufflation pathway in the direction of arrow A, shown in FIG. 33B, as described above.

As a surgical instrument is withdrawn from the trocar 600, it is pulled through the opening 712 in the scraper 620. The opening 712 can scrape fluid from the outside of the surgical instrument. The fluid can travel into the wicking channels 720 and be wicked away from the opening 712. The channels 720 can transfer the fluid to the sorbent 624, where it is held away from the opening 712 so that any subsequently inserted surgical instruments will not be contaminated by fluid. It will be appreciated by those having ordinary skill in the art that the order of use and/or method steps is not important and thus can be performed in any order.

In another embodiment, all of the above described fluid remover embodiments can be formed into a single "drop-in" unit as needed. The drop-in unit can include sorbent elements, scraper elements, wicking elements, and/or combinations thereof. These elements can be combined as needed into an externally configured unit that can be placed into an existing trocar system as needed. Thus, the drop-in unit will fit in and around any seals and components disposed within the proximal housing, including the removable cap, and/or within the cannula. For example, the drop-in unit can be configured to fit below or distal to one or more sealing elements and/or it can be configured to fit above or proximal to one or more sealing elements. Alternatively or in addition, the drop-in unit can be configured to have components that fit above, below, or in between sealing elements. The drop-in unit can also include the seals therein such that the entire unit can be placed into an empty housing of a trocar. The drop-in unit can also be removable as needed, and the unit, or portions thereof, can be reusable.

Methods for removing fluid from a surgical instrument are also generally provided. In an exemplary embodiment, a surgical instrument can be passed through an access device and a fluid remover in the access device can remove any fluid on the instrument, or fluid deposited on a seal within the access device by the instrument. In one exemplary embodiment, a fluid remover can engage a surgical instrument passed through an access device, such as a trocar, upon removal of the instrument to thereby remove fluid from the instrument, thus preventing the fluid from accumulating on the seal(s) and/or from being redeposited on instruments passing therethrough. As indicated above, the fluid remover can be formed from any combination of one or more sorbing, scraping, and wicking elements. A person skilled in the art will appreciate that virtually any combination of sorbing, scraping, and wicking elements can form the fluid remover resulting in a variety of methods for removing fluid that can include any combination of sorbing, scraping, and wicking fluid away from a surgical instrument and/or from a seal or other portion of a trocar or other access device.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. By way of non-limiting example, the scraper and/or sorbent can be removed, cleaned, re-coated with a hydrophilic material, sterilized, and reused. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
a housing defining a working channel sized and configured to receive a surgical instrument;
an insufflation port formed in the housing and configured to deliver an insufflation gas to the working channel;
a seal disposed within the housing and positioned proximal to the insufflation port, the seal being configured to receive the surgical instrument passed through the working channel; and
a fluid remover assembly disposed within the housing and positioned distal to the insufflation port, and having an outer perimeter mounted within the housing and a central opening configured to receive the surgical instrument therethrough, the fluid remover assembly being configured to allow insufflation gas to pass therethrough when the surgical instrument occludes the central opening, the fluid remover assembly including;
a wicking element spaced a distance away from the seal, the wicking, element being configured to wick away fluid collected near the central opening when the surgical instrument is passed through the central opening, to prevent fluid from being deposited on the seal; and
a sorbent disposed distal to the wicking element and configured to receive fluid removed by the fluid remover assembly.

2. The surgical access device of claim 1, wherein the fluid remover assembly further includes a scraper configured to scrape fluid away from the surgical instrument inserted through the central opening.

3. The surgical access device of claim 2, wherein the wicking element is formed on the scraper and is configured to wick fluid away from the central opening.

4. The surgical access device of claim 3, wherein the wicking element comprises a plurality of channels formed in a distal surface of the scraper and extending radially outward from the central opening such that fluid scraped off of the surgical instrument can flow into the plurality of channels.

5. The surgical access device of claim 1, wherein the fluid remover assembly includes a hole formed therein and positioned a distance away from the central opening and the outer perimeter, the hole being configured to allow insufflation gas to pass therethrough.

6. The surgical access device of claim 1, wherein the housing comprises a proximal housing portion and a distal housing portion having a cannula extending distally therefrom, the proximal and distal housing portions being disposed around an inner retainer, the working channel extending through the inner retainer and the cannula, the outer perimeter of the fluid remover assembly being in sealing engagement with the inner retainer and the distal housing portion.

7. The surgical access device of claim 6, wherein the seal is captured between the inner retainer and the proximal housing portion.

8. The surgical access device of claim 6, wherein the distal cannula includes an angled distal surface having a distal-most point and a proximal-most point, the distal-most point being aligned with the insufflation port.

9. The surgical access device of claim 1, further comprising at least one opening formed on an outside wall of the housing and configured for receiving suture.

10. A surgical access device, comprising:
a housing and a cannula extending distally from the housing, the housing and the cannula having a working channel extending therethrough between a proximal opening formed in a proximal end of the housing and a distal end of the cannula, the working channel being sized and configured to receive a surgical instrument;
an insufflation port coupled to the housing and configured to receive and deliver an insufflation gas to the working channel;
a seal disposed within the housing and configured to substantially prevent passage of an insufflation gas from the insufflation port to the proximal opening when no surgical instrument is disposed therethrough; and
a fluid remover assembly disposed within the housing and positioned distal to the insufflation port, and having an outer perimeter mounted within the housing, a central opening formed therethrough and positioned to receive the surgical instrument passed through the working channel, and a hole formed therein between the central opening and the outer perimeter, the hole being configured to allow insufflation gas to pass from the insufflation port to the cannula when the surgical instrument is disposed through and occludes the central opening, the fluid remover assembly including:
a wicking element spaced a distance away from the seal, the wicking element being configured to wick away fluid collected near the central opening when the surgical instrument is passed through the central opening to prevent fluid from being deposited on the seal: and
a sorbent disposed distal to the wicking element and configured to sorb fluid removed by the fluid remover assembly.

11. The surgical access device of claim 10, wherein the fluid remover assembly further includes a scraper configured to scrape fluid off of the surgical instrument passed through the central opening.

12. The surgical access device of claim 11, further comprising a plurality of nubs disposed within the housing and configured to push the sorbent into contact with the scraper.

13. The surgical access device of claim 11, wherein the wicking element is formed on the scraper and is configured to wick fluid away from the central opening.

14. The surgical access device of claim 10, wherein the sorbent has a central opening formed therethrough and axially aligned with the central opening in the scraper, the central opening in the sorbent having a diameter greater than a diameter of the central opening in the scraper.

15. The surgical access device of claim 10, wherein the housing comprises a proximal housing portion and a distal housing portion disposed around an inner retainer, the working channel extending through the inner retainer, the outer perimeter of the fluid remover assembly being in sealing engagement with the inner retainer, and the proximal opening being formed in the proximal housing.

16. The surgical access device of claim 15, wherein the inner retainer is captured between the proximal and distal housing portions.

17. A fluid remover for use with a surgical access device that includes a housing defining a working channel sized to receive a surgical instrument, an insufflation port disposed in the housing, and a seal disposed proximal to the insufflation port, the fluid remover comprising:
a fluid removing member having an outer perimeter and a central opening formed therein for receiving and sealing around the surgical instrument, the fluid removing member having a hole disposed radially outward from the central opening and radially inward from the outer perimeter and being configured to allow insufflation gas to pass therethrough, the fluid removing member including:
a wicking element spaced a distance away from the seal, the wicking element being configured to wick away fluid collected near the central opening when the surgical instrument is passed through the central opening to prevent fluid from being deposited on the seal, and
a sorbent disposed distal to the wicking element and configured to sorb fluid removed by the fluid removing member.

* * * * *